(12) United States Patent
Martin et al.

(10) Patent No.: US 9,861,371 B2
(45) Date of Patent: Jan. 9, 2018

(54) SURGICAL TOOL

(71) Applicants: Keith Edward Martin, Dayton, OH (US); Michael J. Banchieri, Discovery Bay, CA (US); Haskell Simpkins, Cincinnati, OH (US); Benjamin Krupp, Wyoming, OH (US); David Parrott, Cincinnati, OH (US)

(72) Inventors: Keith Edward Martin, Dayton, OH (US); Michael J. Banchieri, Discovery Bay, CA (US); Haskell Simpkins, Cincinnati, OH (US); Benjamin Krupp, Wyoming, OH (US); David Parrott, Cincinnati, OH (US)

(73) Assignee: AtriCure, Inc., Mason, OH (US)

( * ) Notice: Subject to any disclaimer, the term of this patent is extended or adjusted under 35 U.S.C. 154(b) by 0 days.

(21) Appl. No.: 14/934,865

(22) Filed: Nov. 6, 2015

(65) Prior Publication Data

US 2017/0014137 A1    Jan. 19, 2017

Related U.S. Application Data

(63) Continuation of application No. 14/799,576, filed on Jul. 15, 2015.

(51) Int. Cl.
*A61B 17/128* (2006.01)
*A61B 17/122* (2006.01)
(Continued)

(52) U.S. Cl.
CPC ........ *A61B 17/1285* (2013.01); *A61B 17/122* (2013.01); *A61B 17/1227* (2013.01);
(Continued)

(58) Field of Classification Search
CPC ........ A61B 17/1285; A61B 2017/2919; A61B 2017/2939; A61B 17/282; A61B 17/2833; A61B 2018/145
See application file for complete search history.

(56) References Cited

U.S. PATENT DOCUMENTS 6,394,998 B1    5/2002 Wallace et al.
6,582,451 B1 *  6/2003 Marucci ................. A61B 17/29
                                                            606/207
(Continued)

FOREIGN PATENT DOCUMENTS

EP    2 772 206      9/2014
EP    3 117 781     11/2016
(Continued)

*Primary Examiner* — Katherine Rodjom
(74) *Attorney, Agent, or Firm* — Willis IP; Ryan Willis

(57) ABSTRACT

A medical instrument comprising: (a) a first joint comprising a first member and a second member, the first member configured to be repositionable with respect to the second member in a first degree of freedom; (b) a second joint operatively coupled to the first joint, the second joint comprising a third member and a fourth member, the third member configured to be repositionable with respect to the fourth member in a second degree of freedom; (c) a pair of repositionable jaws operatively coupled to the first joint and the second joint; (d) an occlusion clip detachably mounted to the pair of repositionable jaws; and, (e) a controller operatively coupled to the first joint, the second joint, and the pair of repositionable jaws, the controller including a first control configured to direct repositioning of at least one of the first member and the second member, and a second control configured to direct repositioning of at least one of the third member and the fourth member, and a third control configured to direct repositioning of the pair of repositionable jaws.

22 Claims, 37 Drawing Sheets

(51) Int. Cl.
　　　*A61B 17/00*　　　(2006.01)
　　　*A61B 17/29*　　　(2006.01)

(52) U.S. Cl.
　　　CPC . *A61B 17/00234* (2013.01); *A61B 2017/0069* (2013.01); *A61B 2017/00243* (2013.01); *A61B 2017/00314* (2013.01); *A61B 2017/00318* (2013.01); *A61B 2017/2927* (2013.01); *A61B 2017/2937* (2013.01); *A61B 2017/2939* (2013.01)

(56) References Cited

U.S. PATENT DOCUMENTS

| | | |
|---|---|---|
| 2005/0177182 A1 | 8/2005 | van der Burg et al. |
| 2005/0273129 A1 | 12/2005 | Michels et al. |
| 2006/0020271 A1* | 1/2006 | Stewart .............. A61B 17/0057 606/139 |
| 2013/0131649 A1 | 5/2013 | Hughett, Sr. et al. |
| 2013/0190777 A1 | 7/2013 | Hughett, Sr. et al. |
| 2013/0331646 A1 | 12/2013 | Pell et al. |
| 2014/0188159 A1 | 7/2014 | Steege |
| 2014/0194899 A1 | 7/2014 | Madhani et al. |

FOREIGN PATENT DOCUMENTS

| | | |
|---|---|---|
| EP | 3 117 781 | 1/2017 |
| WO | 2009/091497 | 7/2009 |
| WO | 2013/025841 | 2/2013 |
| WO | 2017/011041 | 8/2016 |
| WO | 2017/011041 | 1/2017 |

\* cited by examiner

SURGICAL TOOL

CROSS REFERENCE TO RELATED APPLICATIONS

The present application is a continuation of U.S. Nonprovisional patent application Ser. No. 14/799,576, titled "SURGICAL TOOL," filed Jul. 15, 2015, the disclosure of which is incorporated herein by reference.

INTRODUCTION TO THE INVENTION

The present disclosure is directed to medical instruments and, more specifically, to an applier that may be used to apply a left atrial appendage occlusion clip.

It is a first aspect of the present invention to provide a medical instrument comprising: (a) a first joint comprising a first member and a second member, the first member configured to be repositionable with respect to the second member in a first degree of freedom; (b) a second joint operatively coupled to the first joint, the second joint comprising a third member and a fourth member, the third member configured to be repositionable with respect to the fourth member in a second degree of freedom; (c) a pair of repositionable jaws operatively coupled to the first joint and the second joint; (d) an occlusion clip detachably mounted to the pair of repositionable jaws; and, (e) a controller operatively coupled to the first joint, the second joint, and the pair of repositionable jaws, the controller including a first control configured to direct repositioning of at least one of the first member and the second member, and a second control configured to direct repositioning of at least one of the third member and the fourth member, and a third control configured to direct repositioning of the pair of repositionable jaws.

In a more detailed embodiment of the first aspect, the first control comprises a first active control configured to be repositionable among an infinite number of positions, where each of the infinite number of positions orients the first member with respect to the second member within the first degree of freedom, and the second control comprises a second active control configured to be repositionable among an infinite number of positions, where each of the infinite number of positions orients the third member with respect to the fourth member within the second degree of freedom. In yet another more detailed embodiment, the first active control includes a first wheel around which is partially wound a first wire operatively coupled to at least one of the first member and the second member so that rotation of the first wheel translates into movement of at least one of the first member and the second member, and the second active control includes a second wheel around which is partially wound a second wire operatively coupled to at least one of the third member and the fourth member so that rotation of the second wheel translates into movement of at least one of the third member and the fourth member. In a further detailed embodiment, the medical instrument further includes a repositionable lock in selective communication with at least one of the first control and the second control to retard movement in at least one of the first degree of freedom and the second degree of freedom. In still a further detailed embodiment, the repositionable lock is in selective communication with both the first control and the second control to retard movement of the first joint in the first degree of freedom and the second joint in the second degree of freedom. In a more detailed embodiment, the first control includes a plurality of first teeth, the second control includes a plurality of second teeth, and the repositionable lock includes a catch that concurrently engages at least one of the plurality of first teeth and at least one of the plurality of second teeth. In a more detailed embodiment, the controller is operatively coupled to a hand-held housing, and the repositionable lock is repositionably mounted to the hand-held housing. In another more detailed embodiment, the first control is operatively coupled to a hand-held housing and includes at least one of a pivoting, a sliding, and a rotating first projection extending from the hand-held housing, the second control is operatively coupled to the hand-held housing and includes at least one of a pivoting, a sliding, and a rotating second projection extending from the hand-held housing, and the repositionable lock is operatively coupled to the hand-held housing and includes at least one of a pivoting, a sliding, and a rotating third projection extending from the hand-held housing. In yet another more detailed embodiment, the first control includes a rotating first projection that comprises a first wheel, the second control includes a rotating second projection that comprises a second wheel, the repositionable lock includes a sliding third projection. In still another more detailed embodiment, the medical instrument further includes a longitudinal conduit extending between the controller and the first joint.

In yet another more detailed embodiment of the first aspect, the first member comprises a clevis, and the second member comprises a universal. In yet another more detailed embodiment, the universal includes at least one of a first cavity and a first projection, as well as at least one of a second cavity and a second projection, the clevis includes the other of at least one of the first cavity and the first projection, as well as the other of the second cavity and the second projection, the first projection is configured to be repositionable within the first cavity, and the second projection is configured to be repositionable within the second cavity, in order to allow repositioning of the clevis with respect to the universal within the first degree of freedom. In a further detailed embodiment, the third member comprises the universal, and the fourth member comprises a linkage housing. In still a further detailed embodiment, the universal includes at least one of a third cavity and a third projection, as well as at least one of a fourth cavity and a fourth projection, the linkage housing includes the other of at least one of the first cavity and the first projection, as well as the other of the second cavity and the second projection, the third projection is configured to be repositionable within the second cavity, and the fourth projection is configured to be repositionable within the third cavity, in order to allow repositioning of the universal with respect to the linkage housing within the second degree of freedom. In a more detailed embodiment, the medical instrument further includes a first connection extending along the longitudinal conduit connecting the first control to at least one of the first member and the second member, and a second connection extending along the longitudinal conduit connecting the second control to at least one of the third member and the fourth member. In a more detailed embodiment, the medical instrument further includes a third connection extending along the longitudinal conduit connecting the first control to at least one of the first member and the second member, and a fourth connection extending along the longitudinal conduit connecting the second control to at least one of the third member and the fourth member. In another more detailed embodiment, the first connection, the second connection, the third connection, and the fourth connection each comprise a wire. In yet another more detailed embodiment, the controller further includes a fourth control configured to detachably mount the occlusion clip to the pair of repositionable jaws. In still another more detailed embodiment, the fourth control includes a wire concurrently mounted to the occlusion clip and the pair of repositionable jaws.

In a more detailed embodiment of the first aspect, the wire comprises at least a first wire and a second wire, the first wire is concurrently mounted to the occlusion clip and a first of the pair of repositionable jaws, the second wire is concurrently mounted to the occlusion clip and a second of the pair of repositionable jaws, the fourth control is repositionable to selectively dismount the first wire from at least one of the occlusion clip and the first of the pair of repositionable jaws, and is repositionable to selectively dismount the second from at least one of the occlusion clip and the second of the pair of repositionable jaws. In yet another more detailed embodiment, the fourth control includes a tab mounted to the first wire and the second wire, and the tab is selectively detachable from a hand-held housing. In a further detailed embodiment, the tab is rotationally repositionable with respect to the hand-held housing. In still a further detailed embodiment, the medical instrument further includes a first connection extending along the longitudinal conduit and operatively coupling the third control to the pair of repositionable jaws. In a more detailed embodiment, the medical instrument further includes a folding support that is concurrently mounted to the pair of repositionable jaws and the fourth member of the second joint, the folding support repositionable between a folded position and an unfolded position, where the folded position has the pair of repositionable jaws in closer proximity to one another than in the unfolded position. In a more detailed embodiment, the folding support is operatively coupled to a pulley and the first link. In another more detailed embodiment, the folding support includes: (a) a first link concurrently repositionably and operatively coupled to a first of the pair of repositionable jaws; (b) a second link concurrently repositionably and operatively coupled to a second of the pair of repositionable jaws; (c) a third link concurrently repositionably and operatively coupled to the first of the pair of repositionable jaws and the second link; and, (d) a fourth link concurrently repositionably and operatively coupled to the second of the pair of repositionable jaws and the first link, where the third link is repositionably and operatively coupled to the fourth link.

In a more detailed embodiment of the first aspect, the folding support includes a fifth link concurrently repositionably and operatively coupled to a sixth link and to the first link, wherein the sixth link is concurrently repositionably and operatively coupled to the fifth link and to the second link. In yet another more detailed embodiment, the fifth and sixth links are both mounted to and repositionable with respect to a pulley. In a further detailed embodiment, the second joint includes a first camming surface to facilitate repositioning of the fifth link, and the second joint includes a second camming surface to facilitate repositioning of the sixth link. In still a further detailed embodiment, the first connection is operatively coupled to the fifth and sixth links. In a more detailed embodiment, the first connection includes a pulley operatively coupled to the fifth and sixth links. In a more detailed embodiment, the third control comprises a repositionable handle operatively coupled to a hand-held housing of the controller. In another more detailed embodiment, the third control includes a slide arm concurrently mounted to the repositionable handle and the first connection. In yet another more detailed embodiment, the third control includes a spring to bias at least one of the slide arm and the handle, and the third control includes a trigger to selectively unlock the orientation of the handle with respect to the slide arm. In still another more detailed embodiment, the first wire comprises a first pair of wires partially wound around the first wheel, where the first pair of wires is mounted to the second member, and the second wire comprises a second pair of wires partially wound around the second wheel, where the second pair of wires is mounted to the third member.

In yet another more detailed embodiment of the first aspect, the first wheel around which the first pair of wires are partially wound around has a first diameter, the second wheel around which the second pair of wires are partially wound around has a second diameter, where the first diameter is larger than the second diameter. In yet another more detailed embodiment, the folding support comprises a folding pantograph support.

It is a second aspect of the present invention to provide a method of controlling an end effector of a medical instrument, the medical instrument including a hand-held device operatively coupled to the end effector, comprising: (a) providing a first control of the hand-held device configured to direct repositioning of at least one of a first member and a second member of a first joint of the end effector, the first member and second member being repositionable with respect to one another in a first degree of freedom; (b) providing a second control of the hand-held device configured to direct repositioning of at least one of a third member and a fourth member of a second joint of the end effector, the third member and fourth member being repositionable with respect to one another in a second degree of freedom different from the first degree of freedom; and, (c) providing a third control of the hand-held device configured to direct repositioning of a folding support between a compact position and an expanded position, the folding support connecting the first and second joints.

In a more detailed embodiment of the second aspect, the method further includes providing a fourth control of the hand-held device configured to selectively disengage an occlusion clip operatively coupled to the folding support. In yet another more detailed embodiment, the first control includes a first wheel having a first wire partially wound therearound, where the first wire is also operatively coupled to at least one of the first member and the second member of the first joint of the end effector, and the second control includes a second wheel having a second wire partially wound therearound, where the second wire is also operatively coupled to at least one of the third member and the fourth member of the second joint of the end effector. In a further detailed embodiment, the third control includes a repositionable handle operatively coupled to the hand-held device, the repositionable handle operatively coupled to a wire that is operatively coupled to the folding support to allow repositioning of the folding support between the compact position and the expanded position.

It is a third aspect of the present invention to provide a medical instrument end effector comprising: (a) a first joint comprising a first member and a second member, the first member configured to be repositionable with respect to the second member in a first degree of freedom; (b) a second joint operatively coupled to the first joint, the second joint comprising a third member and a fourth member, the third member configured to be repositionable with respect to the fourth member in a second degree of freedom; and, (c) a pair of repositionable jaws operatively coupled to the first joint and the second joint by a folding support.

In a more detailed embodiment of the third aspect, the end effector further includes an occlusion clip detachably mounted to the pair of repositionable jaws. In yet another more detailed embodiment, the end effector further includes a controller including a first control configured to direct repositioning of the first joint, a second control configured to direct repositioning of the second joint, and a third control configured to direct repositioning of the pair of repositionable jaws, and a longitudinal conduit extending between the controller and the first joint. In a further detailed embodiment, the first member comprises a clevis, and the second member comprises a universal. In still a further detailed embodiment, the universal includes at least one of a first cavity and a first projection, as well as at least one of a second cavity and a second projection, the clevis includes the other of at least one of the first cavity and the first projection, as well as the other of the second cavity and the second projection, and the first projection is configured to be repositionable within the first cavity, and the second projection is configured to be repositionable within the second cavity, in order to allow repositioning of the clevis with respect to the universal within the first degree of freedom. In a more detailed embodiment, the third member comprises the universal, and the fourth member comprises a linkage housing. In a more detailed embodiment, the universal includes at least one of a third cavity and a third projection, as well as at least one of a fourth cavity and a fourth projection, the linkage housing includes the other of at least one of the first cavity and the first projection, as well as the other of the second cavity and the second projection, the third projection is configured to be repositionable within the second cavity, and the fourth projection is configured to be repositionable within the fourth cavity, in order to allow repositioning of the universal with respect to the linkage housing within the second degree of freedom. In another more detailed embodiment, a wire concurrently mounts the occlusion clip to the pair of repositionable jaws. In yet another more detailed embodiment, the folding support is concurrently mounted to the pair of repositionable jaws and the fourth member of the second joint, the folding support repositionable between a folded position and an unfolded position, where the folded position has the pair of repositionable jaws in closer proximity to one another than in the unfolded position. In still another more detailed embodiment, the folding support is operatively coupled to a pulley and the first link.

In yet another more detailed embodiment of the third aspect, the folding support includes: (a) a first link concurrently repositionably and operatively coupled to a first of the pair of repositionable jaws; (b) a second link concurrently repositionably and operatively coupled to a second of the pair of repositionable jaws; (c) a third link concurrently repositionably and operatively coupled to the first of the pair of repositionable jaws and the second link; and, (d) a fourth link concurrently repositionably and operatively coupled to the second of the pair of repositionable jaws and the first link, where the third link is repositionably and operatively coupled to the fourth link. In yet another more detailed embodiment, the folding support includes a fifth link concurrently repositionably and operatively coupled to a sixth link and to the first link, wherein the sixth link is concurrently repositionably and operatively coupled to the fifth link and to the second link. In a further detailed embodiment, the fifth and sixth links are both mounted to and repositionable with respect to a pulley. In still a further detailed embodiment, the second joint includes a first camming surface to facilitate repositioning of the fifth link, and the second joint includes a second camming surface to facilitate repositioning of the sixth link. In a more detailed embodiment, a first connection is operatively coupled to the fifth and sixth links. In a more detailed embodiment, the first connection includes a pulley operatively coupled to the fifth and sixth links. In another more detailed embodiment, the folding support comprises a folding pantograph support.

It is a fourth aspect of the present invention to provide a method of deploying an occlusion clip comprising: (a) inserting an occlusion clip removably mounted to an end effector deployment device having repositionable jaws through at least one of an incision and a trocar, the occlusion clip and the end effector deployment device mounted to one another when inserted into and through at least one of the incision and the trocar; (b) repositioning the end effector deployment device to reposition the occlusion clip so the occlusion clip is interposed by a portion of a left atrial appendage interposing a base and a tip of the left atrial appendage by passing the tip of the left atrial appendage between opposing clamping surfaces of the occlusion clip and; (c) clamping the left atrial appendage with the occlusion clip to occlude the left atrial appendage without piercing the left atrial appendage between the occlusion clip; (d) disengaging the occlusion clip from the end effector deployment device; and, (e) withdrawing the end effector deployment device through at least one of the incision and the trocar.

In a more detailed embodiment of the fourth aspect, the inserting step occurs during at least one of an open sternotomy, a left thoracotomy, a right thoracotomy, a left port procedure, a right port procedure, a subxiphoid approach, and a transdiaphragmatic approach. In yet another more detailed embodiment, the method further includes insufflating a thoracic space prior to the inserting step. In a further detailed embodiment, the method further includes making an incision as part of a procedure comprising at least one of an open sternotomy, a left thoracotomy, a right thoracotomy, a left port procedure, a right port procedure, a subxiphoid approach, and a transdiaphragmatic approach, and introducing a trocar through the incision. In still a further detailed embodiment, the end effector deployment device is mounted to a longitudinal conduit, which is mounted to a hand-held device, and repositioning the end effector deployment device step includes actuating at least one of a first control and a second control associated with the hand-held device to actively reposition the end effector within at least one of an X-Y plane and a Y-Z plane with respect to the hand-held device. In a more detailed embodiment, the end effector deployment device is mounted to a longitudinal conduit, which is mounted to a hand-held device, the method further comprising repositioning the occlusion clip from a compressed position to an expanded position prior to interposing a portion of the left atrial appendage between the opposing clamping surfaces. In a more detailed embodiment, the method further includes actuating a handle associated with the hand-held device to direct repositioning of the occlusion clip between the compressed position and the expanded position. In another more detailed embodiment, actuating the handle causes a pair of jaws associated with the end effector to reposition with respect to one another, and the pair of jaws is mounted to the occlusion clip. In yet another more detailed embodiment, the end effector deployment device is mounted to a longitudinal conduit, which is mounted to a hand-held device, the method further comprising rotationally repositioning the occlusion clip with respect to the left atrial appendage by rotating the hand-held device. In still another more detailed embodiment, the method further includes grasping the left atrial appendage concurrent with repositioning the end effector deployment device to reposition the occlusion clip so the open end of the occlusion clip is interposed by the portion of the left atrial appendage.

In yet another more detailed embodiment of the fourth aspect, the method further includes repeating the repositioning and clamping steps prior to the disengaging step. In yet another more detailed embodiment, the method further includes confirming a clamping position of the occlusion clip is operative to occlude the left atrial appendage using at least one of visualization and a transesophageal echocardiogram. In a further detailed embodiment, the end effector deployment device is mounted to a longitudinal conduit, which is mounted to a hand-held device, and disengaging the occlusion clip from the end effector deployment device includes actuating a control associated with the hand-held device. In still a further detailed embodiment, the control comprises a repositionable tab operatively coupled to a wire, which is operatively coupled the end effector and the occlusion clip, and removing the repositionable tab from the hand-held device repositions the wire with respect to at least one loop encompassing at least one of the occlusion clip and the end effector deployment device in order to disengage the occlusion clip from the end effector deployment device. In a more detailed embodiment, the inserting step includes inserting the occlusion clip and the end effector deployment device through the trocar, the withdrawing step includes withdrawing the end effector deployment device through the trocar, and the trocar comprises a twelve millimeter or less diameter orifice. In a more detailed embodiment, the end effector deployment device is mounted to a longitudinal conduit, which is mounted to a hand-held device, and the step of repositioning the end effector deployment device to reposition the occlusion clip includes locking a position of the end effect deployment device in at least one of an X-Y plane and a Y-Z plane with respect to the hand-held device.

It is a fifth aspect of the present invention to provide a method of deploying an occlusion clip comprising: (a) inserting an occlusion clip removably mounted to an end effector deployment device having repositionable jaws through at least one of an incision and a trocar, the occlusion clip and the end effector deployment device mounted to one another when inserted into and through the trocar; (b) repositioning the end effector deployment device to reposition the occlusion clip so the occlusion clip is interposed by a portion of a left atrial appendage interposing a base and a tip of the left atrial appendage by passing the tip of the left atrial appendage between opposing clamping surfaces of the occlusion clip; (c) clamping the left atrial appendage with the occlusion clip in an initial position without piercing the left atrial appendage between the occlusion clip; (d) assessing the operability of the occlusion clip in the initial position to occlude the left atrial appendage; and, (e) repositioning the end effector deployment device to reposition the occlusion clip to a subsequent position, different from the initial position, to clamp the left atrial appendage, where repositioning the occlusion clip from the initial position to the subsequent position is repeatable without affecting the structural integrity of the left atrial appendage.

It is an sixth aspect of the present invention to provide a method of deploying an occlusion clip comprising: (a) inserting an occlusion clip removably mounted to an end effector deployment device, having repositionable jaws, through at least one of an incision and a trocar, the occlusion clip biased to a clamping position; (b) repositioning the end effector deployment device to counteract a bias of the occlusion clip and reposition the occlusion clip to a tissue insertion position where the full bias of the occlusion clip is not applied to a left atrial appendage tissue; (c) repositioning the end effector deployment device to reposition the occlusion clip in the tissue insertion position so a portion of a left atrial appendage between a base and a tip of the left atrial appendage interposes the occlusion clip by having the tip of the left atrial appendage pass between opposing beams of the occlusion clip; (d) repositioning the occlusion clip to apply the full bias to the left atrial appendage; and, (e) removing the end effector deployment device from around the left atrial appendage without passing the tip of the left atrial appendage between the repositionable jaws.

In a more detailed embodiment of the sixth aspect, the method further includes disengaging the occlusion clip from the end effector deployment device, and withdrawing the end effector deployment device through at least one of the incision and the trocar. In yet another more detailed embodiment, the inserting step occurs during at least one of an open sternotomy, a left thoracotomy, a right thoracotomy, a left port procedure, a right port procedure, a subxiphoid approach, and a transdiaphragmatic approach. In a further detailed embodiment, the method includes insufflating a thoracic space prior to the inserting step. In still a further detailed embodiment, the method further includes making an incision as part of a procedure comprising at least one of an open sternotomy, a left thoracotomy, a right thoracotomy, a left port procedure, a right port procedure, a subxiphoid approach, and a transdiaphragmatic approach, and introducing a trocar through the incision. In a more detailed embodiment, the end effector deployment device is mounted to a longitudinal conduit, which is mounted to a hand-held device, and repositioning the end effector deployment device step includes actuating at least one of a first control and a second control associated with the hand-held device to actively reposition the end effector within at least one of an X-Y plane and a Y-Z plane with respect to the hand-held device. In a more detailed embodiment, the end effector deployment device is mounted to a longitudinal conduit, which is mounted to a hand-held device, the method further comprising repositioning the occlusion clip from a compressed position to an expanded position prior to interposing a portion of the left atrial appendage between the opposing clamping surfaces. In another more detailed embodiment, the method further includes actuating a handle associated with the hand-held device to direct repositioning of the occlusion clip between the compressed position and the expanded position. In yet another more detailed embodiment, actuating the handle causes a pair of jaws associated with the end effector to reposition with respect to one another, and the pair of jaws is mounted to the occlusion clip. In still another more detailed embodiment, the end effector deployment device is mounted to a longitudinal conduit, which is mounted to a hand-held device, the method further comprising rotationally repositioning the occlusion clip with respect to the left atrial appendage by rotating the hand-held device.

In yet another more detailed embodiment of the sixth aspect, the method further includes grasping the left atrial appendage concurrent with repositioning the end effector deployment device to reposition the occlusion clip so the open end of the occlusion clip is interposed by the portion of the left atrial appendage. In yet another more detailed embodiment, the method further includes confirming application of the full bias of the occlusion clip is operative to occlude the left atrial appendage using at least one of visualization and a transesophageal echocardiogram. In a further detailed embodiment, the method further includes disengaging the occlusion clip from the end effector deployment device, where the end effector deployment device is mounted to a longitudinal conduit, which is mounted to a hand-held device, and disengaging the occlusion clip from the end effector deployment device includes actuating a control associated with the hand-held device. In still a further detailed embodiment, the control comprises a repositionable tab operatively coupled to a wire, which is operatively coupled to the end effector and the occlusion clip, and removing the repositionable tab from the hand-held device repositions the wire with respect to at least one loop encompassing at least one of the occlusion clip and the end effector deployment device in order to disengage the occlusion clip from the end effector deployment device. In a more detailed embodiment, the inserting step includes inserting the occlusion clip and the end effector deployment device through the trocar, and the trocar comprises a twelve millimeter or less diameter orifice. In a more detailed embodiment, the end effector deployment device is mounted to a longitudinal conduit, which is mounted to a hand-held device, and the step of repositioning the end effector deployment device to reposition the occlusion clip includes locking a position of the end effect deployment device in at least one of an X-Y plane and a Y-Z plane with respect to the hand-held device.

It is a seventh aspect of the present invention to provide a method of facilitating repositioning of an end effector and an occlusion clip mounted thereto, the method comprising: (a) providing an occlusion clip removably mounted to an end effector; (b) providing a first attachment operatively coupled to the end effector and the occlusion clip, the first attachment operatively coupled to a first user control configured to selectively disengage the end effector from the occlusion clip; (c) providing a first joint as part of the end effector to allow repositioning of a first portion of the end effector with respect to a second portion of the end effector, the first portion mounted to the occlusion clip, while the second portion is operatively coupled to the occlusion clip via the first portion.

In a more detailed embodiment of the seventh aspect, the first attachment comprises loop and a wire, the loop at least partially circumscribing the occlusion clip and the wire when the occlusion clip is mounted to the end effector and no longer circumscribing the wire when the occlusion clip is removed from the end effector. In yet another more detailed embodiment, the method further includes providing a second joint as part of the end effector to allow repositioning of the second portion of the end effector with respect to a third portion of the end effector, the first joint allowing motion between the first portion and the second portion in a first degree of freedom, the second joint allowing motion between the second portion and the third portion in a second degree of freedom, different from the first degree of freedom. In a further detailed embodiment, the method further includes providing a second user control to direct repositioning of the first portion with respect to the second portion, providing a third user control to direct repositioning of the second portion with respect to the third portion, where the second user control and the third user control comprise a handheld control. In still a further detailed embodiment, the method further includes providing a second user control to direct repositioning of the first portion with respect to the second portion, wherein the first user control and the second user control comprise a handheld control. In a more detailed embodiment, the method further includes providing a second joint as part of the end effector to allow repositioning of the second portion of the end effector with respect to a third portion of the end effector, the first joint allowing motion between the first portion and the second portion in a first degree of freedom, the second joint allowing motion between the second portion and the third portion in a second degree of freedom, different from the first degree of freedom.

In yet another more detailed embodiment of the seventh aspect, the method further includes providing a third user control to direct repositioning of the second portion with respect to the third portion, wherein the third user control comprises a portion of the handheld control. In yet another more detailed embodiment, the method further includes providing parallel opening jaws that are removably mounted to the occlusion clip and comprise a portion of the end effector. In a further detailed embodiment, the parallel opening jaws comprise a first jaw and a second jaw, the first jaw is pivotally mounted to a first drive link and a first parallel link, the second jaw is pivotally mounted to a second drive link and a second parallel link, and at least two of the first drive link, the second drive link, the first parallel link, and the second parallel link are pivotally mounted to a pulley.

DETAILED DESCRIPTION

The exemplary embodiments of the present disclosure are described and illustrated below to encompass devices, methods, and techniques relating to surgical procedures. Of course, it will be apparent to those of ordinary skill in the art that the embodiments discussed below are exemplary in nature and may be reconfigured without departing from the scope and spirit of the present disclosure. It is also to be understood that variations of the exemplary embodiments contemplated by one of ordinary skill in the art shall concurrently comprise part of the instant disclosure. However, for clarity and precision, the exemplary embodiments as discussed below may include optional steps, methods, and features that one of ordinary skill should recognize as not being a requisite to fall within the scope of the present disclosure.

Figure 1:
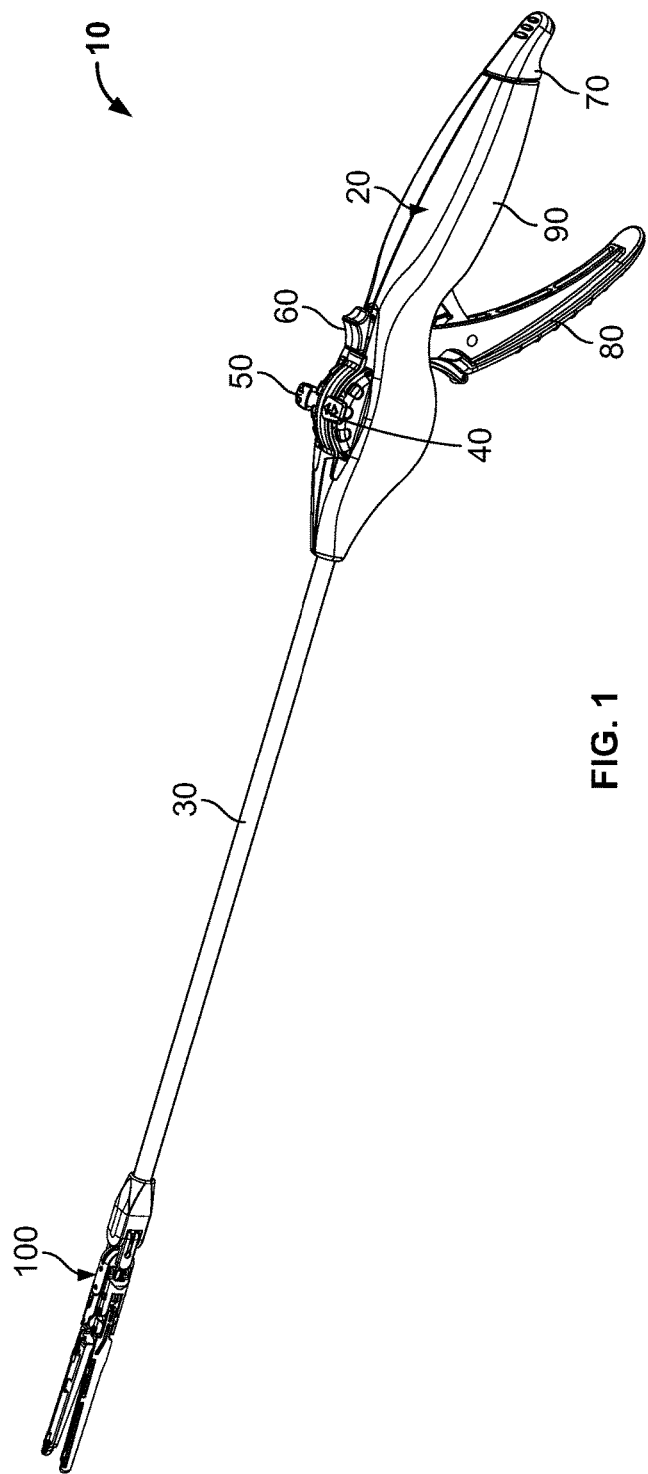
FIG. 1 is an elevated perspective view of an exemplary surgical tool in accordance with the instant disclosure.

Referencing FIG. 1, an exemplary surgical tool 10 includes a user control 20 mounted to a shaft assembly 30, which is mounted to an exemplary minimally invasive surgical end effector 100. The user control 20 includes a first wheel control 40 to vary the yaw of the end effector 100, while the user control 20 further includes a second wheel control 50 to vary the pitch of the end effector. A user of the control 20 may manipulate the roll of the end effector 100 simply by rolling the user control. In order to selectively inhibit manipulation of the wheel controls 40, 50, a repositionable lock 60 is also provided. A proximal end of the user control 20 further includes a repositionable tab 70 that may be utilized to, in exemplary form, disengage a left atrial appendage (LAA) occlusion clip from the end effector 100. In addition, the user control 20 includes a lever control 80 that is operative to control repositioning of the jaws of the end effector 100 with respect to one another. Several of the components of the lever control 80, the wheel controls 40, 50, and the repositionable lock 60 at least partially reside within a grip housing 90. A more detailed discussion of the exemplary components of the surgical tool 10 will be discussed successively.

Referring to FIGS. 1-3 and 51-56, the exemplary end effector 100 may be used in minimally invasive surgical procedures to allow deployment of an LAA occlusion clip 102 with respect to a left atrial appendage (not shown). United States Patent Application Publication number 2012/0059400, which describes an exemplary LAA occlusion clip 102, is incorporated herein by reference. As will be apparent to those skilled in the art after reviewing the instant disclosure, the end effector 100 and surgical tool 10 may be utilized in capacities other than LAA occlusion clip deployment, each of which is within the scope of this disclosure.

The end effector 100 comprises a clevis 110 that is mounted proximally to the shaft assembly 30 and distally to a proximal portion of a universal 120, which is rotatably repositionable within an X-Y plane with respect to the clevis. A distal portion of the universal 120 is mounted to a proximal portion of a linkage housing 130 that is rotatably repositionable within a Y-Z plane with respect to the universal. A medial portion of the linkage housing 130 has mounted to it a first pin 160 that extends through a first drive link 140 and a second drive link 150. In this fashion, the first drive link 140 and the second drive link 150 are rotatably repositionable with respect to the linkage housing 130 and with respect to one another along a common axis longitudinally aligned with the first pin 160. A distal portion of the linkage housing 130 has mounted to it a second pin 170 and a third pin 230 that extends through proximal ends of a first parallel link 180 and a second parallel link 190. In this fashion, the first parallel link 180 and the second parallel link 190 are rotatably repositionable with respect to the linkage housing 130 and with respect to one another along a common axis longitudinally aligned with the second and third pins 170, 230.

Interposing the proximal ends of the first and second parallel links 180, 190 are a first toggle 200, a second toggle 210, and a pulley 220. The pulley 220 includes a pair of cylindrical projections extending in opposite directions along a rotational axis of the pulley, where the first toggle 200 is mounted to a first of the cylindrical projections and the second toggle 210 is mounted to a second of the cylindrical projections. A distal end of the first drive link 140 is mounted to a proximal end of a first jaw 240, whereas a distal end of the second drive link 150 is mounted to a proximal end of a second jaw 250. In this fashion, the first drive link 140 is rotatably repositionable with respect to the first jaw 240 along a common axis longitudinally aligned with a fifth pin 260 that concurrently extends through the first drive link and the first jaw. Similarly, the second drive link 150 is rotatably repositionable with respect to the second jaw 250 along a common axis longitudinally aligned with a sixth pin 270 that concurrently extends through the second drive link and the second jaw.

Near the proximal end of the first jaw 240, inset distally from the location where the first drive link 140 is mounted, the distal end of the first parallel link 180 is mounted to the first jaw. In this fashion, the first parallel link 180 is rotatably repositionable with respect to the first jaw 240 along a common axis longitudinally aligned with a seventh pin 290 that concurrently extends through the first parallel link and the first jaw. In corresponding fashion, the proximal end of the second jaw 250, inset distally from the location where the second drive link 150, is mounted to the distal end of the second parallel link 190. Similarly, the second parallel link 190 is rotatably repositionable with respect to the second jaw 250 along a common axis longitudinally aligned with an eighth pin 300 that concurrently extends through the second parallel link and the second jaw.

In this exemplary end effector 100, the jaws 240, 250 are repositioned toward and away from one another while maintaining a parallel orientation. In order to reposition the first and second jaws 240, 250 with respect to one another, the first and second drive links 140, 150 as well as the first and second parallel links 180, 190 are rotated with respect to the linkage housing 130. To facilitate this repositioning of the jaws 240, 250 with respect to one another, the distal ends of the first and second toggles 200, 210 are mounted to medial portions of respective drive links 140, 150. In particular, the distal end of the first toggle 200 is mounted to a medial portion of the first drive link 140 via a ninth pin 310. Accordingly, the first toggle 200 is rotatably repositionable with respect to the first drive link 140 along a common axis longitudinally aligned with the ninth pin 310. In addition, the distal end of the second toggle 210 is mounted to a medial portion of the second drive link 150 via a tenth pin 320. Consequently, the second toggle 210 is rotatably repositionable with respect to the second drive link 150 along a common axis longitudinally aligned with the tenth pin 320. A more detailed discussion of the component parts of the end effector 100 follows.

Figure 57:
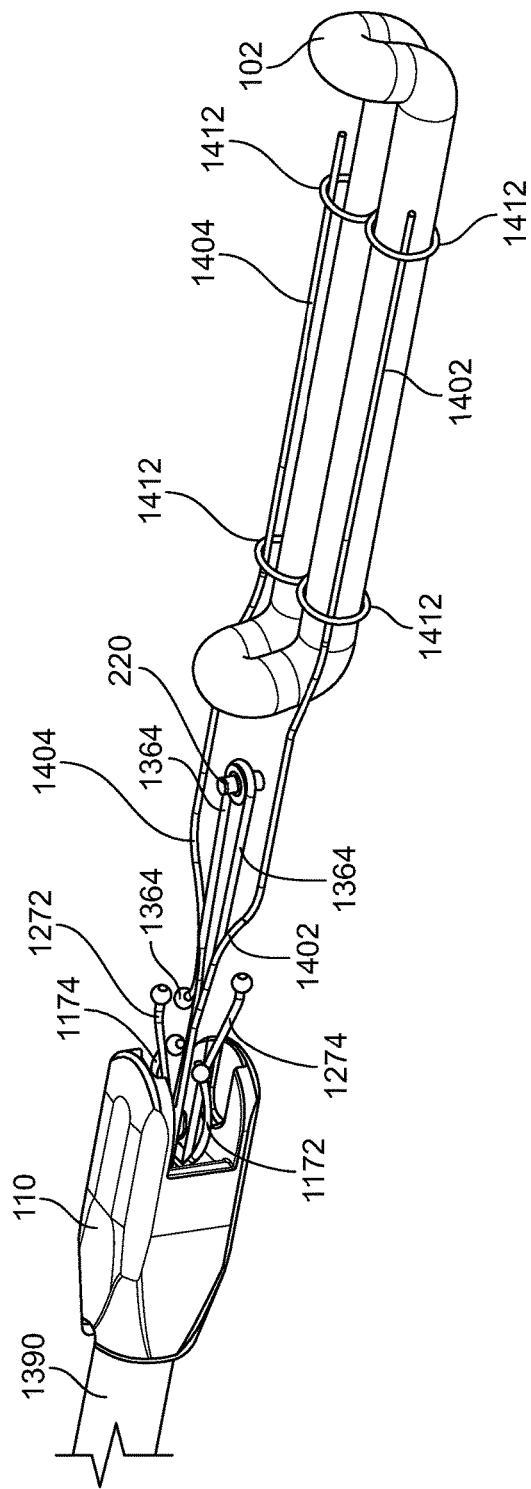
FIG. 57 is an elevated perspective view of the exemplary end effector and occlusion clip of FIG. 52 shown without repositionable jaws, first and second drive links, first and second parallel links, first and second toggles, linkage housing, and universal.

As shown in FIGS. 4-7, the clevis 110 includes an outer shell 400 that defines a longitudinal passage 402 extending therethrough. A proximal end 404 of the shell 400 includes an inner, cylindrical surface 406 that circumscribes an elongated shaft 1390 of the shaft assembly 30 (see FIG. 53) and retains the shaft therein via a compression fit. This inner, cylindrical surface 406 abuts a dam 408 that inhibits further distal repositioning of the shaft 1390. Extending through the dam 408 are a pair of cylindrical through holes 410 interposed by an elongated through hole 412. In exemplary form, separate control wires control wires 1272, 1274 (see FIG. 56) extend through each cylindrical hole 410 and are coupled to the universal 120 and to the first wheel control 40 so that manipulation of the first wheel control is operative to reposition the universal with respect to the clevis 110. In addition, another group of wires 1172, 1174, 1364, 1402, 1404 (see FIG. 57) extend through the elongated hole 412. A more detailed discussion of the wires and the structures to which each is mounted will be discussed hereafter.

On a distal side of the holes 410, 412, an overhang 416 and corresponding underhang 418, along with corresponding interior walls 422, partially define a distal opening. In particular, the overhang 416 and underhang 418 are mirror images of one another and include an arcuate profile that curves away from the dam 408 until terminating at opposing planar upper and lower walls 424. Inset within each of the interior walls 422 is a C-shaped depression 426, where the open end of the C-shape faces distally. As will be discussed in more detail hereafter, a peripheral surface 430 partially delineating the C-shaped depression 426 bridges between the interior wall 422 and a step wall 432, and provides a camming surface against which the universal 120 rotates. In this exemplary embodiment, the interior walls 422 are planar and parallel to one another, as are the step walls 432, in addition to the interior walls being parallel to the step walls. Interposing the upper and lower walls 424 are convex side surfaces 436, where the convex side surfaces abut distal curved surfaces 438 that partially delineate the C-shaped depression 426 and likewise extend between the upper and lower walls. Extending proximally, the upper and lower walls 424 and the convex side surfaces 436 transition from a generally rectangular exterior cross-section to a circular cross-section at a proximal end 440 via a series of tapered walls 442. Extending distally from the clevis 110 is the universal 120.

Referring to FIGS. 8-11, the universal 120 comprises a pair of projections 450 extending outward from opposing right and left side surfaces 452. In this exemplary embodiment, the projections 450 include a plateau surface 454 that is generally planar and parallel with the planar surface of the nearest side surface 452. A peripheral shape of each projection 450 is rounded on a proximal end and comes to a point on a distal end 451 that is generally centered with a midline extending through the universal 120. In particular, the peripheral surface 456 of each projection 450 is intended to contact and ride against the peripheral surface 430 of the clevis 110 (see FIG. 4) in order to allow pivotal motion between the clevis and universal 120. But the pointed shape of each projection 450, as embodied by two linear segments of the peripheral surface 456, is operative to provide opposing stops that prevent complete rotation of the universal 120 with respect to the clevis 110. By way of example, the linear segments of the peripheral surface 456 are angled approximately ninety degrees with respect to one another so that the universal 120 can rotate±forty-five degrees with respect to a longitudinal axis extending through the clevis 110 in the proximal-distal direction. Each projection 450 is generally centered between opposing top and bottom surfaces 460 and distally inset from a proximal end 462.

The proximal end 462 of the universal 120 is semicircular in profile to ride against the overhang 416 and underhang 418 of the clevis 110 (see FIG. 4) when the universal is rotated with respect to the clevis. In particular, the proximal end 462 includes a central U-shaped channel 466 that terminates at corresponding key-shaped through openings 468 extending through the top and bottom surfaces 460 and into an interior of the universal 120. The key-shaped opening 468 includes a cylindrical, enlarged opening 469 that is configured to accept an enlarged end of a control wire 1172, 1174 (see FIGS. 56 and 57). Once passing through the cylindrical opening 469, the enlarged end of the control wire 1172, 1174 is retained within a capture, which is partially delineated via a depression 464, which inhibits throughput of the enlarged end of the control wire through the smaller height aspect of the key-shaped through openings 468. A height of the U-shaped channel 466 extending along the top and bottom surfaces 460 is sufficient to accommodate the width of a control wire 1172, 1174, but not so high as to allow throughput of the enlarged end of the control wire, with the exception of through the enlarged cylindrical opening. Corresponding interior surfaces 470 delineating a portion of the U-shaped channel 466 are convex and arcuate in shape. Extending co-planar with the U-shaped channel 466 is a through opening 474 is sized to accommodate throughput of further control wires. The base of the U-shaped channel and the through opening 474 interpose opposing left and right side channels 476, 478.

A proximal end of each of the channels 476, 478 is delineated by spaced apart, arcuately shaped complementary walls 482, 484. As mentioned previously, a peripheral surface of these walls 482, 484 ride against the overhang 416 and underhang 418 of the clevis 110. Each of the channels 476, 478 tapers from proximal to distal and creates a dedicated through opening that extends through the universal 120 and into an internal region partially bounded by opposing distal extensions 490.

Inset within each interior wall 492 of the distal extensions 490 is a C-shaped depression 496, where the open end of the C-shape faces distally. As will be discussed in more detail hereafter, a peripheral surface 498 partially delineating the C-shaped depression 496 bridges between the interior wall 492 and a step wall 502, and provides a camming surface against which the linkage housing 130 rotates. In this exemplary embodiment, the interior walls 492 are planar and parallel to one another, as are the step walls 502, in addition to the interior walls being parallel to the step walls. The step walls 502 and the top and bottom surfaces 460 converge at respective distal ends of the distal extensions 490 to form a semicircular edge 504, which is interposed by the linkage housing 130.

As shown in FIGS. 12-15, the linkage housing includes a pair of projections 510 extending outward from opposing top and bottom exterior surfaces 512. In this exemplary embodiment, the projections 510 include a plateau surface 514 that is generally planar and parallel with the planar surface of the nearest top/bottom surface 512. A peripheral shape of each projection 510 is rounded on a proximal end and comes to a point on a distal end 511 that is generally centered with a midline extending through the linkage housing 130. In particular, the peripheral surface 516 of each projection 510 is intended to contact and ride against the peripheral surface 498 of the universal 120 in order to allow pivotal motion between the linkage housing 130 and universal 120. But the pointed shape of each projection 510, as embodied by two linear segments of the peripheral surface 516, is operative to provide opposing stops that prevent complete rotation of the linkage housing 130 with respect to the universal 120. By way of example, the linear segments of the peripheral surface 516 are angled approximately ninety degrees with respect to one another so that the linkage housing 130 can rotate±forty-five degrees with respect to a longitudinal axis extending through the universal 120 in the proximal-distal direction. Each projection 510 is generally centered between opposing right and left sides 520 and distally inset from a proximal end 522.

The proximal end 522 of the linkage housing 130 is semicircular in profile. In particular, the proximal end 522 includes a miniature U-shaped channel 526 that terminates at corresponding openings 528 extending through the left and right side surfaces 520 and into an interior of the linkage housing 130. Each opening 528 is configured to allow throughput of a separate control wire, but prohibit an enlarged end of that control wire 1272, 1274 from passing therethrough (see FIGS. 14 and 57). And a height of the U-shaped channel 526 extending along the left and right side surfaces 520 is sufficient to accommodate the width of a control wire, but not so high as to allow throughput of the enlarged end of the control wire. In exemplary form, each control wire is inserted through one of the openings 528 (smaller diameter end first) so that the remainder of the control wire extends proximally and a distal, enlarged end of the control wire eventually interposes respective outer retention arms 530, 532 and inner arms 534, 536 when the wire is tensioned. Tensioning of both control wires 1272, 1274 is operative to seat the enlarged end of each control wire within a depression 540 formed into the linkage housing 130.

Interposing the miniature U-shaped channel 526 and extending from the base of the U-shaped channel is a central through channel 546 that extends distally and terminates in between the inner arms 534, 536. The central through channel 546 is sized to accommodate a control wire 1364 coupled to the pulley 220 (see FIG. 55). As will be discussed in more detail hereafter, repositioning of the pulley 220 with respect to the linkage housing 130 results in component motion operative to increase or decrease the distance between the opposing jaws 240, 250 responsive to components being pivotally connected to the outer retention arms 530, 532 and inner arms 534, 536.

In exemplary form, the outer retention arms 530, 532 each include a C-shaped depression 556, where the open end of the C-shape faces distally, which is formed into a respective interior wall surface 552. As will be discussed in more detail hereafter, a peripheral surface 558 partially delineating the C-shaped depression 556 bridges between the interior wall surface 552 and a step wall surface 562, and provides a camming surface against which the parallel links 180, 190 rotate. In this exemplary embodiment, the interior wall surfaces 552 are planar and parallel to one another, as are the step wall surfaces 562, in addition to the interior wall surfaces being parallel to the step wall surfaces. The step wall surfaces 562 and the left and right side surfaces 520 converge at respective distal ends of the outer retention arms 530, 532 to form a semicircular edge 564. A distal orifice 568 extends through the step wall surface and through the entire outer retention arm 530, 532. The distal orifice 568 is sized to accommodate one of the second pin 170 and the third pin 230 in order to allow pivotal motion between the linkage housing 130 and the parallel links 180, 190. By way of example, the distal orifices 568 of the outer retention arms 530, 532 are cylindrical and have axial centers that lie along a common axis. In addition to the distal orifice, each outer retention arm 530, 532 also includes a proximal orifice 570 that extends entirely through the outer retention arm. The proximal orifice 570 is sized to accommodate the first pin 160 in order to allow pivotal motion between the linkage housing 130 and the drive links 140, 150. By way of example, the proximal orifices 570 of the outer retention arms 530, 532 are cylindrical and have axial centers that lie along a common axis.

The inner arms 534, 536 extend distally and are generally parallel with the outer retention arms 530, 532, with spacing between each set of adjacent arms. In exemplary form, the inner arms 534, 536 each include a single hole 580 that extends laterally through the arm and is cylindrical in shape. A central axis extending through each hole 580 is coaxial with the counterpart central axis of the other hole. Likewise, the central axis of the holes 580 is coaxial with the common axis of the proximal orifices 570 so that the holes and orifices are sized to accommodate the first pin 160 in order to allow pivotal motion between the linkage housing 130 and the drive links 140, 150 (see FIG. 2). The spacing between the arms 534, 536 allows for proximal-to-distal motion of the pulley 220 therebetween, while prohibiting motion of the toggles 200, 210 therebetween. Rather, the first arm 534 includes a triangular projection extending distally, the hypotenuse of which comprises a first surface 582 that is angled to generally face the top surface 512. Similarly, the second arm 536 includes a triangular projection extending distally, the hypotenuse of which comprises a second surface 584 that is angled to generally face the bottom surface 512. In this exemplary embodiment, the surfaces 582, 584 are perpendicular to one another and, as will be discussed in more detail hereafter, the toggles 200, 210 contact these surfaces in order to limit repositioning of the toggles as the pulley 220 is repositioned.

Referencing FIGS. 2 and 16-18, the first and second drive links 140, 150 as well as the first and second parallel links 180, 190 are rotationally repositionable and mounted to the linkage housing 130. In exemplary form, the first and second drive links 140, 150 are structurally identical, but differ only in operation based upon the components mounted thereto. Consequently, the following discussion of the structure of a drive link is applicable to both the first and second drive links 140, 150.

Each drive link 140, 150 comprises a unitary structure including a pair of spaced apart, tilted uprights 590, 592 that are angled approximately forty-five degrees with respect to corresponding longitudinal extensions 594, 596. The base of the uprights 590, 592 are joined to one another via a bridge 598. In exemplary form, each upright 590, 592 includes a rounded proximal end 600 that interposes opposing planar surfaces 604, 606. Extending completely through each upright 590, 592 is a hole 610 partially bounded by the opposing planar surfaces 604, 606 and having a cylindrical shape that is sized to accommodate throughput of the first pin 160 and allow rotational repositioning of each upright around the first pin. Each upright 590, 592 also includes a step 612 recessed distally beyond the proximal end 600 and the hole 610. The step 612, as will be discussed in more detail hereafter, is inset to approximately half of the thickness of the widest portion of the upright 590, 592. Extending distally from the step 612, each upright 590, 592 seamlessly transitions into a respective longitudinal extension 594, 596. The bridge 598 is positioned approximate the transition region between the uprights 590, 592 and the longitudinal extensions 594, 596 and recessed with respect to bottom planar surfaces 614 of the longitudinal extensions. On the top side 616 of each drive link 140, 150, the bridge 598 seamlessly transitions into the longitudinal extensions 594, 596 an embodies an arcuate, convex longitudinal profile so that the top of each longitudinal extension includes a longitudinal ridge 618 extending from the bridge 598 distally toward a distal rounded end 620 of each longitudinal extension. Along the longitudinal length of each longitudinal extension 594, 596 is a pair of openings 622, 624 extending completely through the longitudinal extensions between opposing lateral inner and exterior sides 628, 630. Each opening 622, 624 has a cylindrical shape and is configured to receive at least one of the fifth, sixth, ninth, and tenth pins 260, 270, 310, 320. In this fashion, the first and second toggles 200, 210 as well as the first and second jaws 240, 250 may be rotationally repositionable with respect to one of the drive links 140, 150.

Referring to FIGS. 2 and 25-27, the first and second toggles 200, 210 as well as the first and second jaws 240, 250 are rotationally repositionable and mounted to the drive links 140, 150. In exemplary form, the first and second toggles 200, 210 are structurally identical, but differ only in operation based upon the components mounted thereto. Consequently, the following discussion of the structure of a toggle is applicable to both the first and second toggles 200, 210.

Each toggle 200, 210 comprises a unitary structure including toggle connector portion 640 and a drive link connector portion 642. In exemplary form, the toggle connector portion includes a rounded end 644 with a substantially constant width that is approximately half of the width of the drive link connector portion 642. Along the longitudinal length of the toggle connector portion 640, an arcuate profile exists. This toggle connector portion 640 includes a through opening 646 having a cylindrical shape and configured to receive a cylindrical projection of the pulley 220 so that the toggle 200, 210 is rotationally repositionable about the pulley 220.

Opposite the toggle connector portion 640, the drive link connector portion 642 includes an offset 648 extending widthwise beyond the width of the toggle connector. An opening 650 extends through the drive link connector portion 642 and the offset 648 having a cylindrical shape and configured to receive one of the ninth and tenth pins 310, 320 so that the toggle 200, 210 is rotationally repositionable about a drive link 140, 150. A partial circumferential groove 652 exists on the rounded end 654 of the drive link connector portion 642. This groove 652 is configured to receive a portion of a deployment wire 1402, 1404 (see FIG. 54) in order to allow the deployment wire to contact and be unimpeded by motion of the toggle 200, 210 when the toggle is repositioned and/or when the deployment wire is repositioned with respect to the jaws 240, 250 in order to detach, for example, a left atrial occlusion clip 102 temporarily mounted to the jaws.

Figure 19:
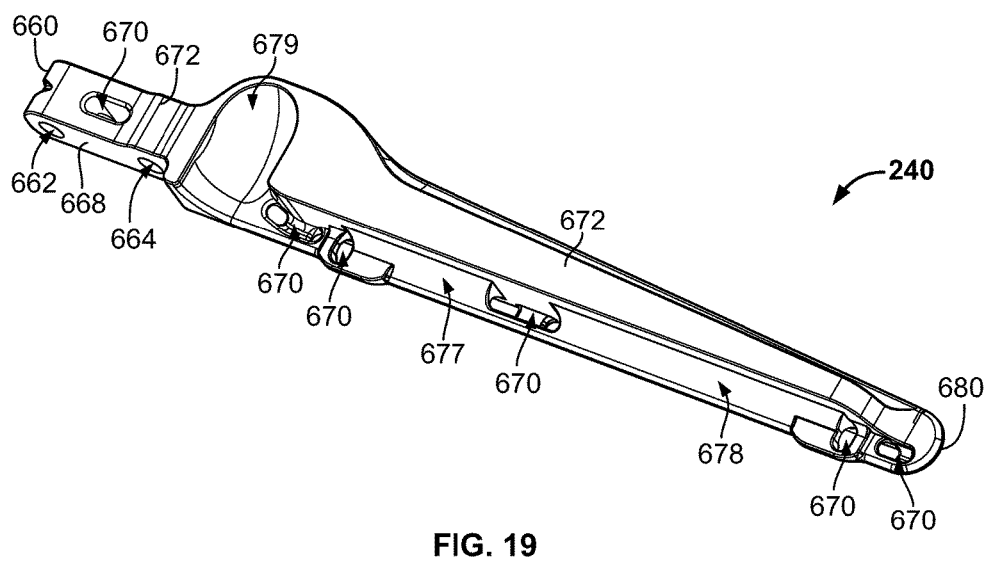
FIG. 19 is an elevated perspective view from a distal end of a first jaw in accordance with the instant invention.
Figure 20:
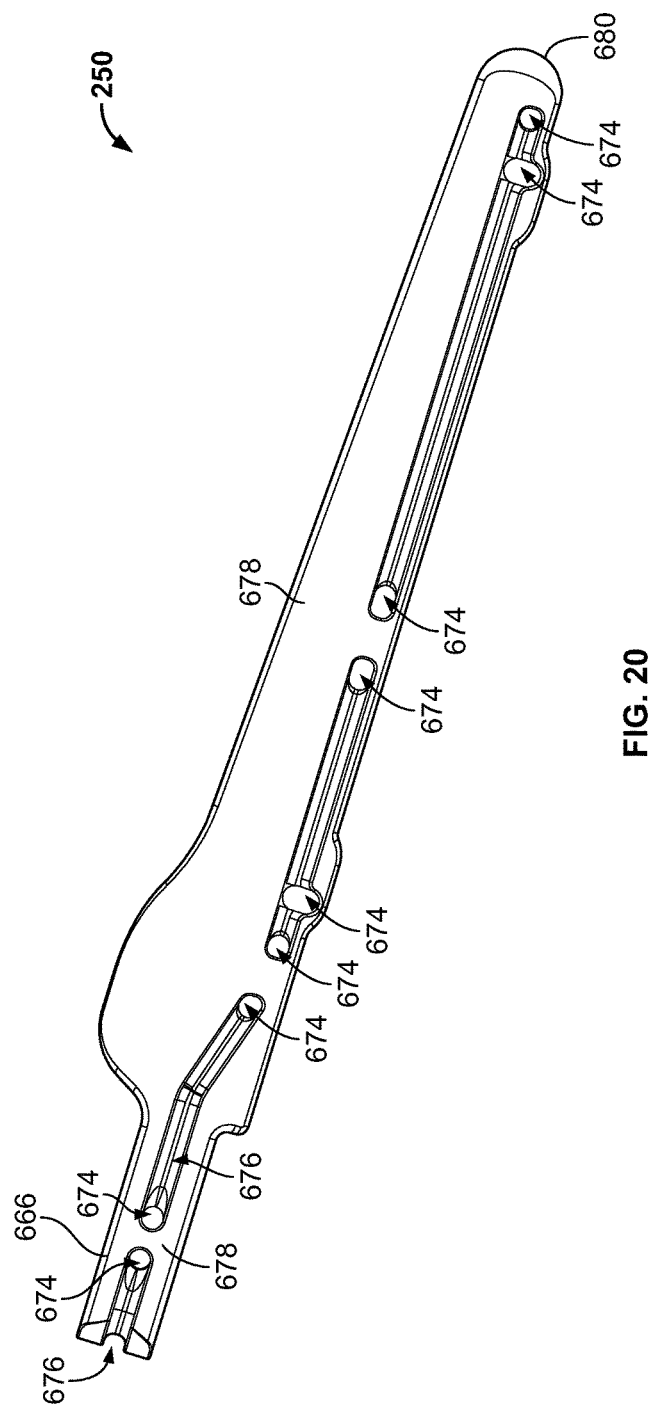
FIG. 20 is profile view of a second jaw in accordance with the instant invention.
Figure 21:
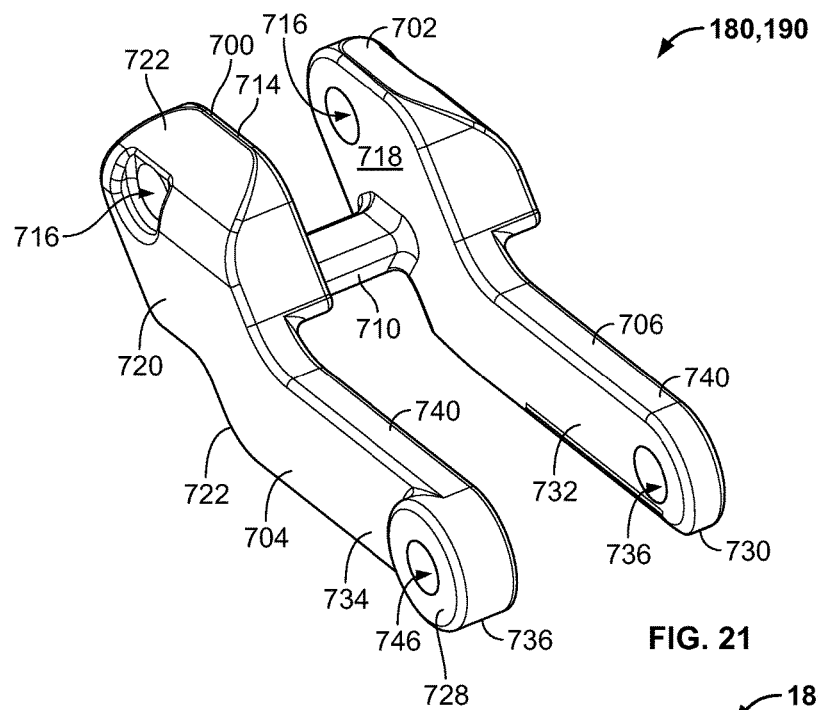
FIG. 21 is an elevated perspective view from a proximal end of an exemplary parallel link in accordance with the instant disclosure.
Figure 22:
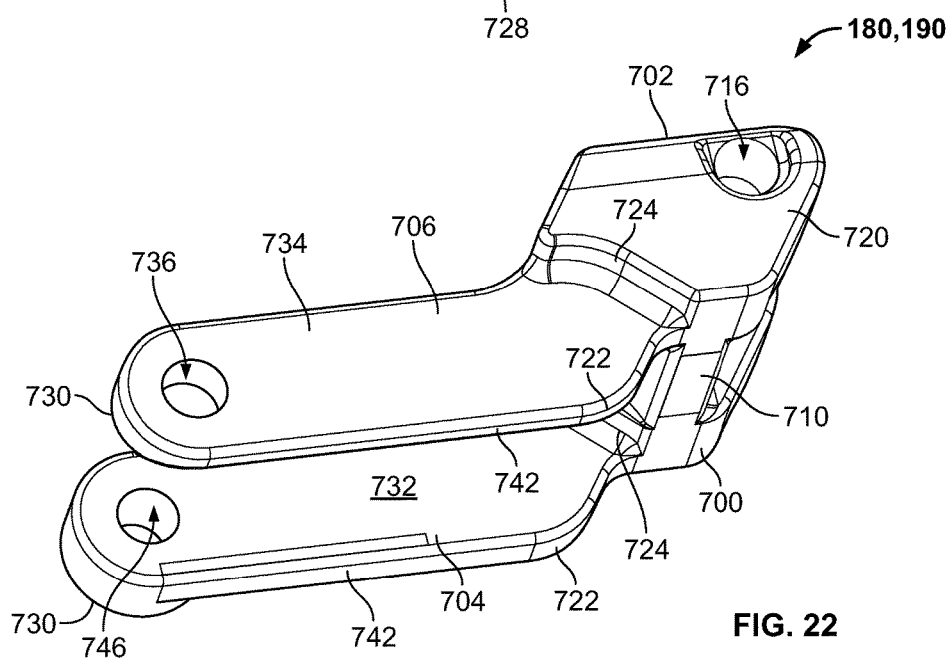
FIG. 22 is an elevated perspective view from a side of the exemplary parallel link of FIG. 21.
Figure 23:
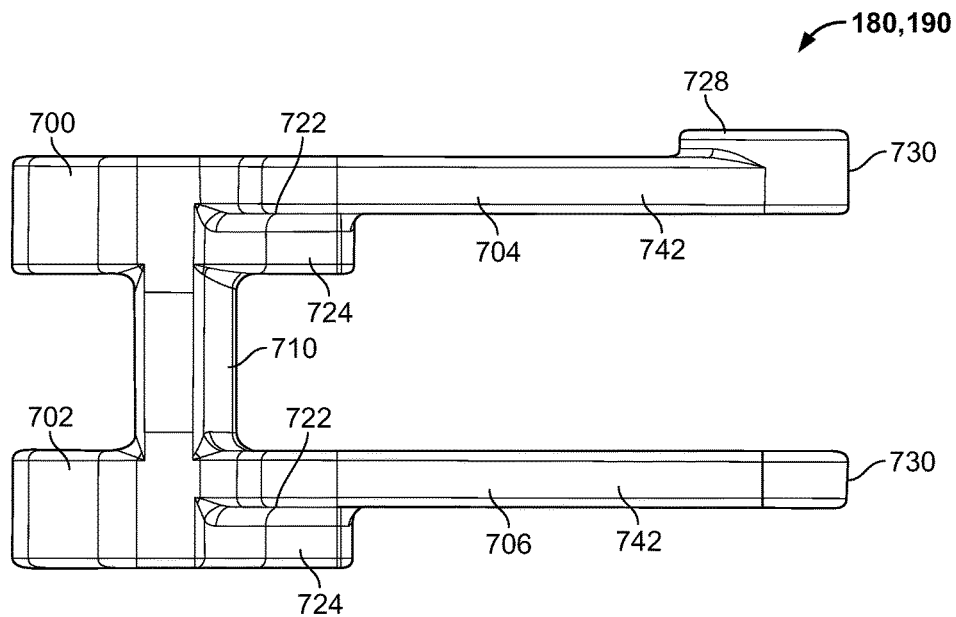
FIG. 23 is a bottom view of the exemplary parallel link of FIG. 21.

As shown in FIGS. 19 and 20, the jaws 240, 250 are structurally mirror images of one another. Consequently, the following discussion of the structure of a jaw is generally applicable to both the first and second jaws 240, 250.

Figure 2:
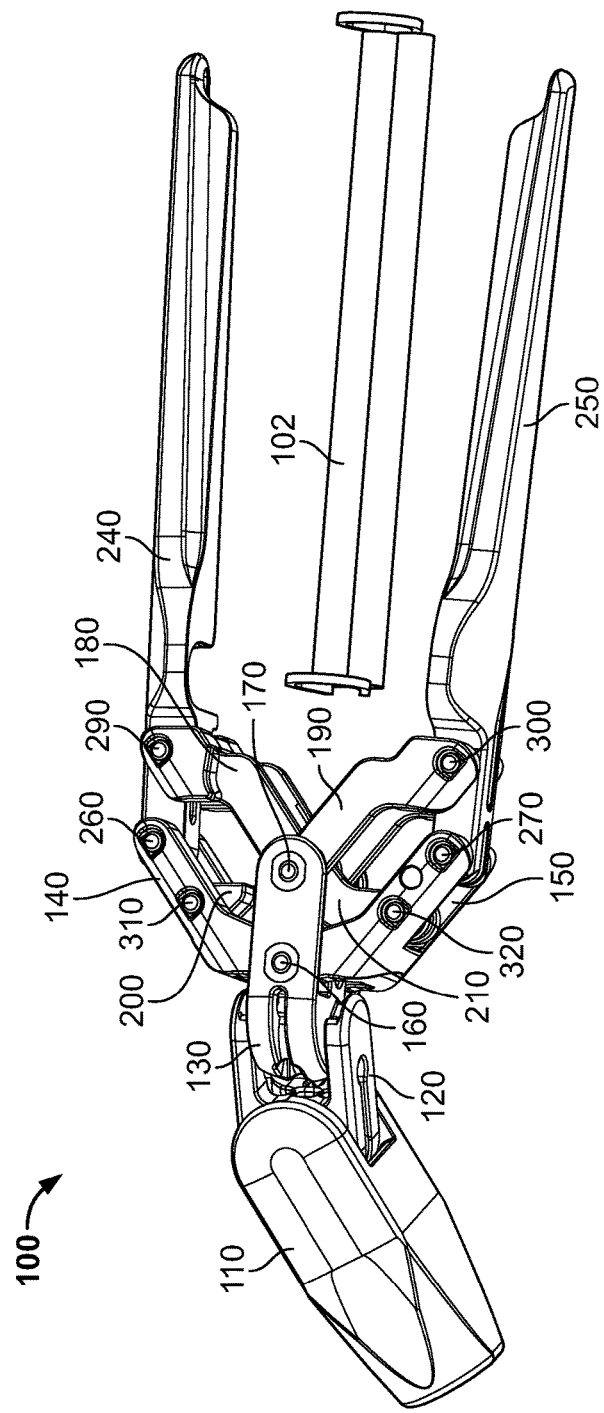
FIG. 2 is an elevated perspective view of the end effector of FIG. 1, shown in the expanded position after having deployed an occlusion clip.
Figure 3:
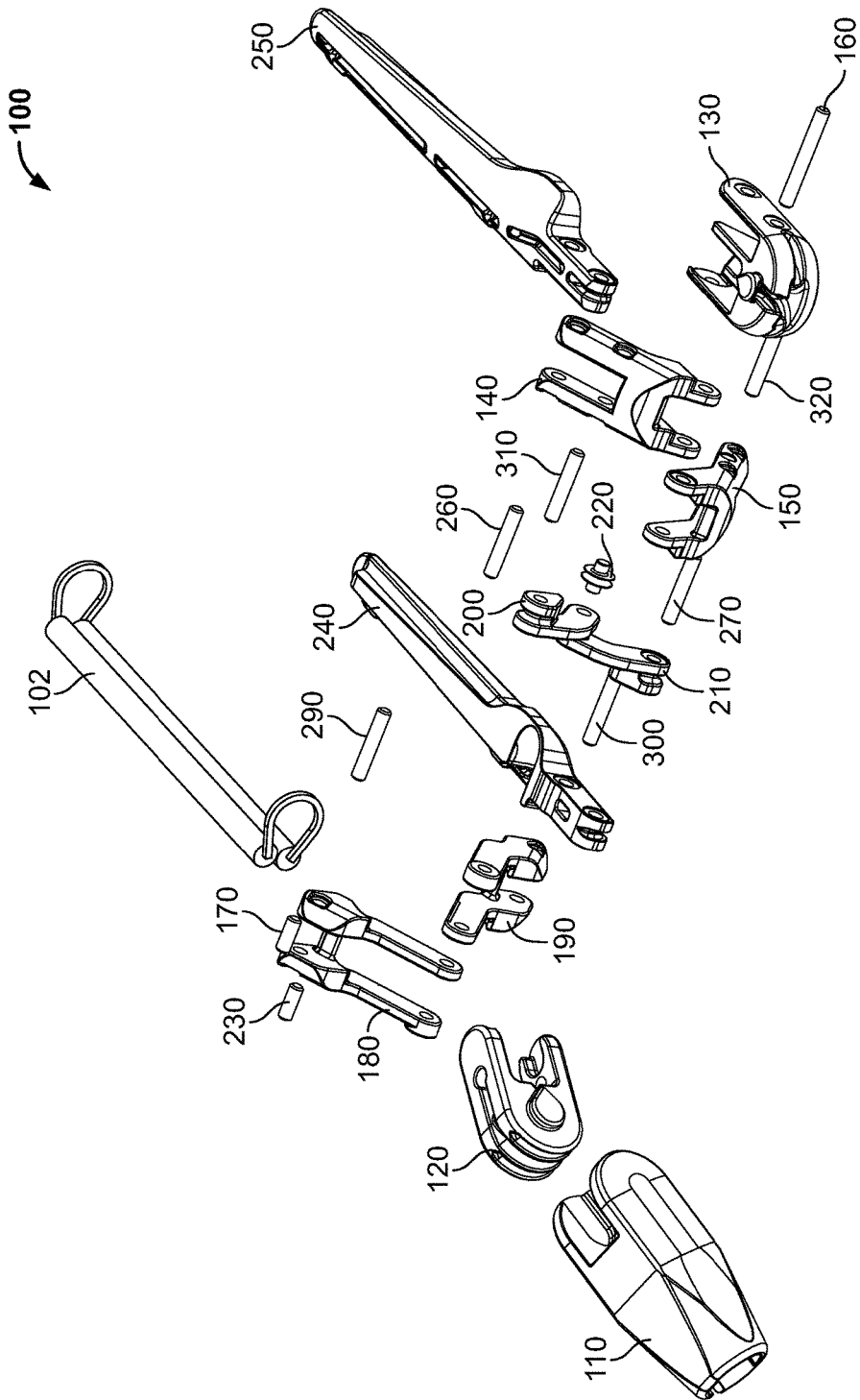
FIG. 3 is an exploded view of the end effector of FIG. 2.
Figure 4:
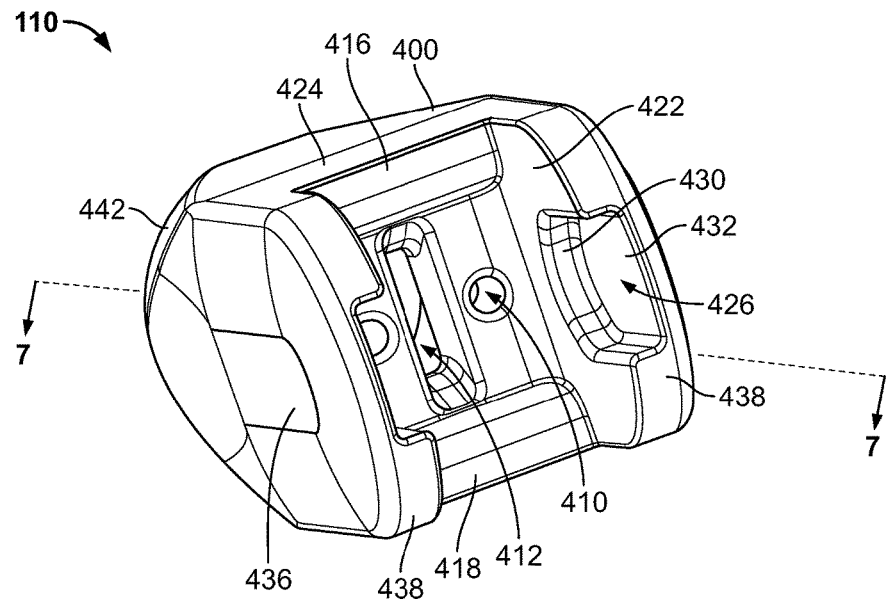
FIG. 4 is an elevated perspective view from a distal end of an exemplary clevis in accordance with the instant disclosure.
Figure 5:
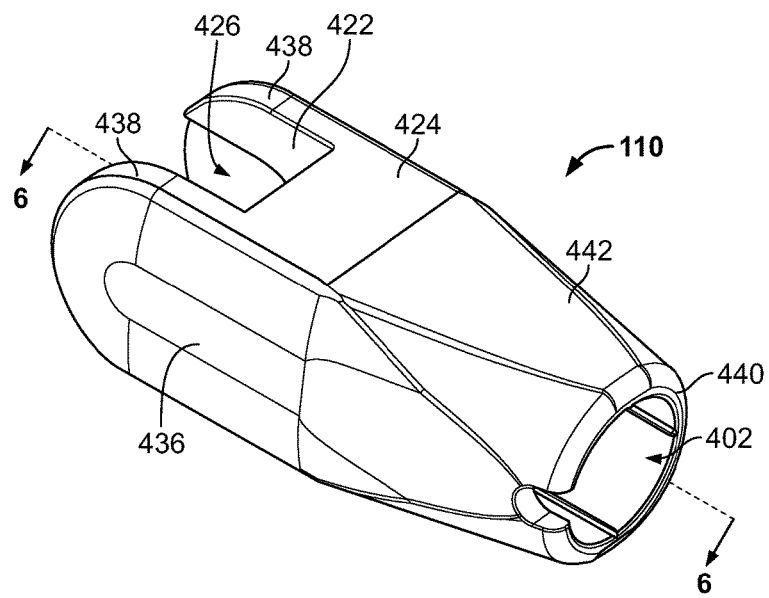
FIG. 5 is an elevated perspective view from a proximal end of the exemplary clevis of FIG. 4.
Figure 6:
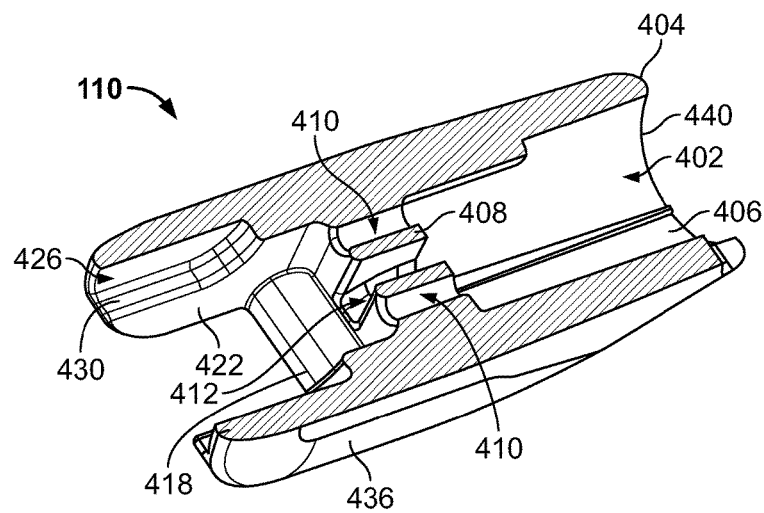
FIG. 6 is a cross-sectional view of the exemplary clevis of FIG. 5 taken along line 6-6.
Figure 7:
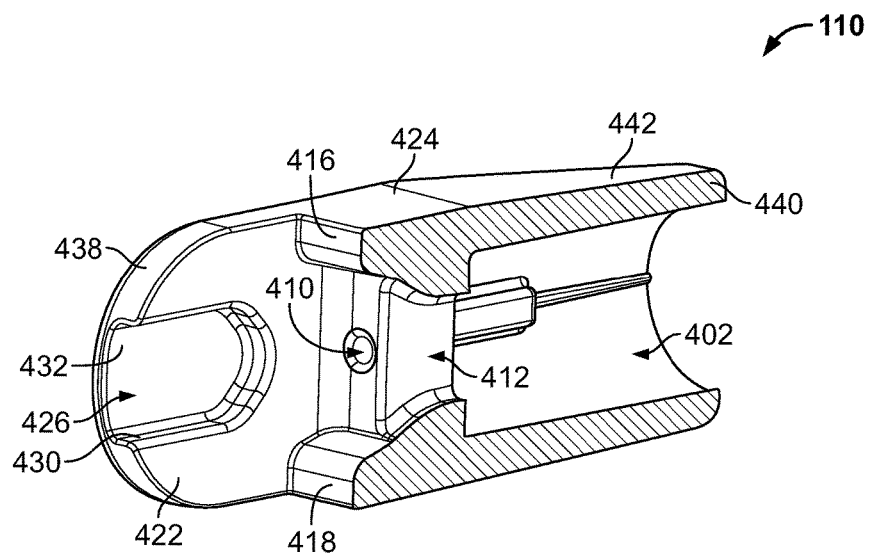
FIG. 7 is a cross-sectional view of the exemplary clevis of FIG. 4 taken along line 7-7.
Figure 8:
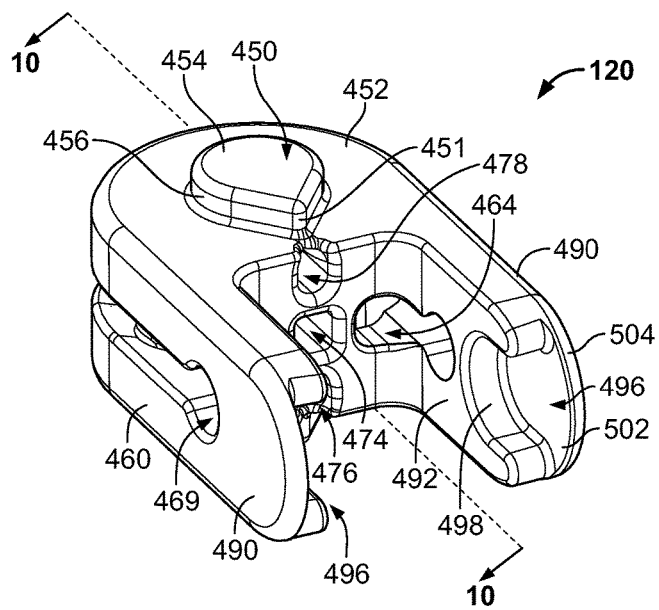
FIG. 8 is an elevated perspective view from a distal end of an exemplary universal in accordance with the instant disclosure.
Figure 9:
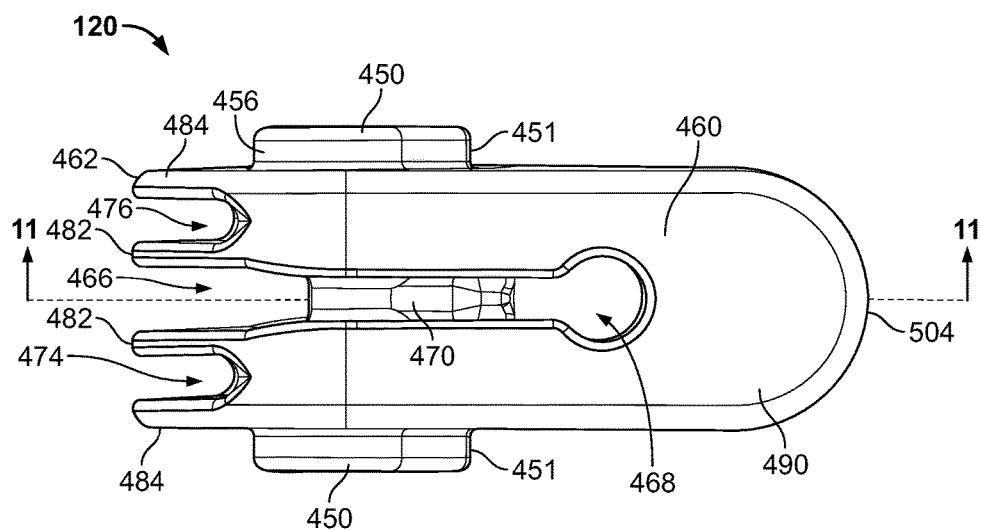
FIG. 9 is a profile view of the exemplary universal of FIG. 8.
Figure 10:
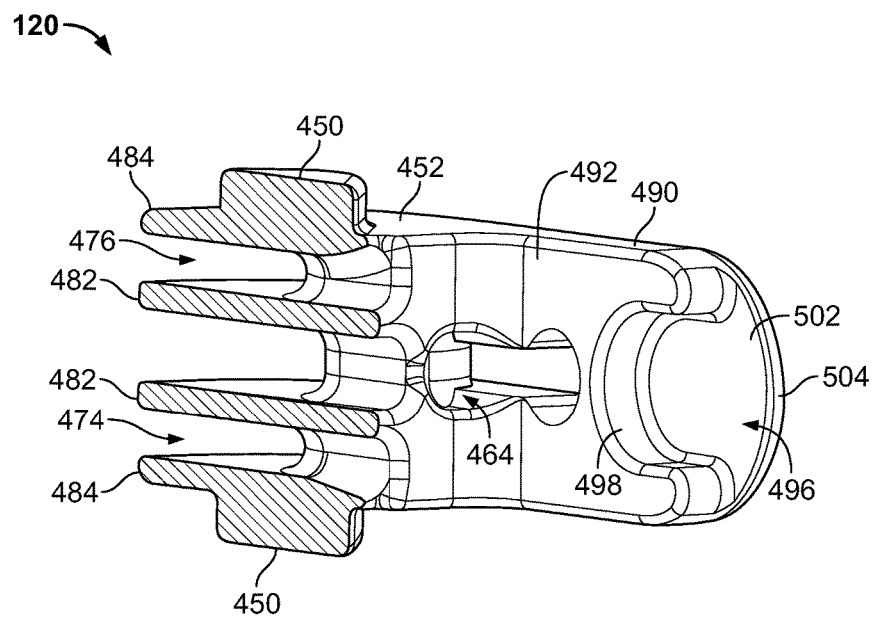
FIG. 10 is a cross-sectional view of the exemplary universal of FIG. 8 taken along line 10-10.
Figure 11:
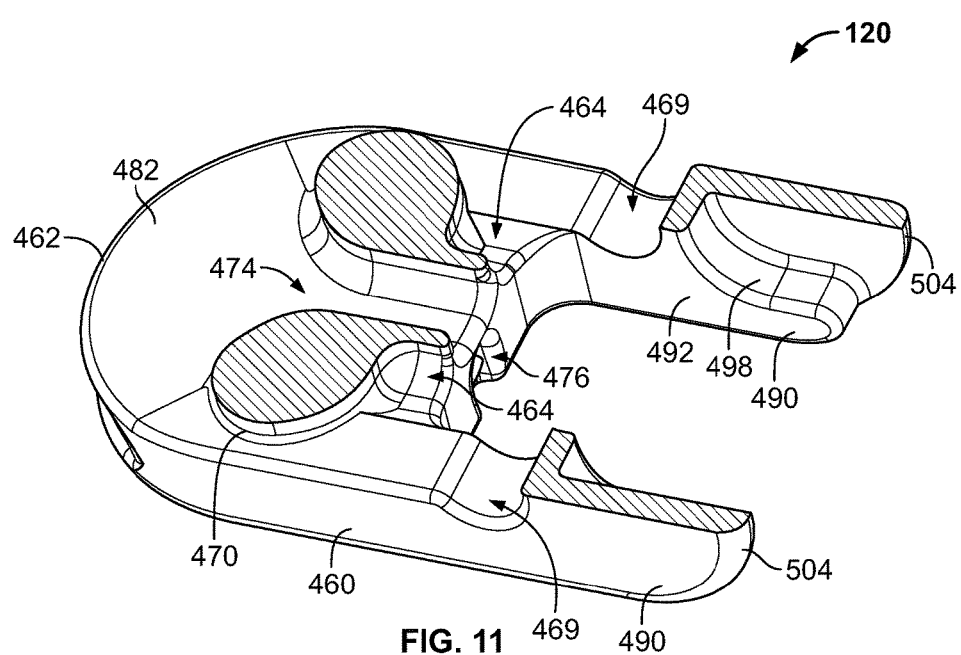
FIG. 11 is a cross-sectional view of the exemplary clevis of FIG. 9 taken along line 11-11.
Figure 12:
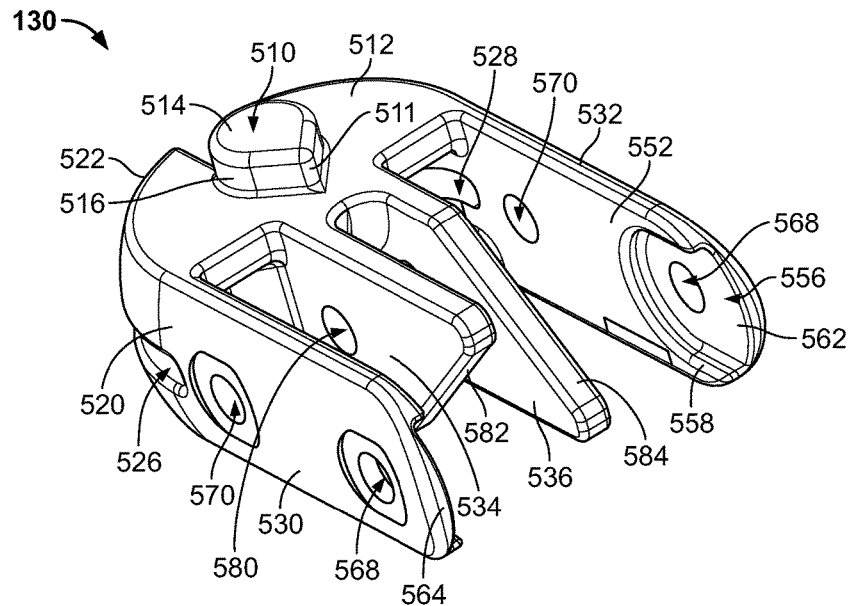
FIG. 12 is an elevated perspective view from a distal end of an exemplary linkage housing in accordance with the instant disclosure.
Figure 13:
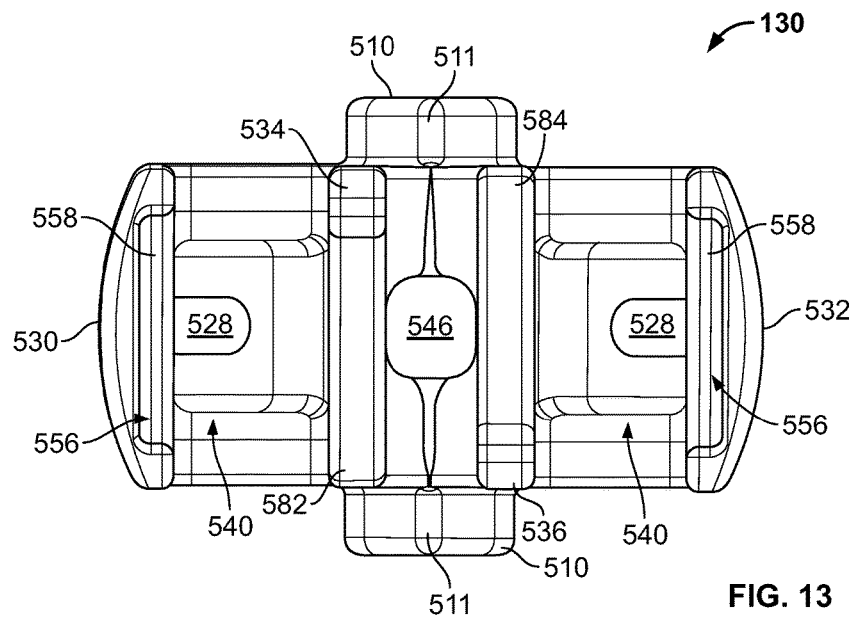
FIG. 13 is a distal end view of the exemplary linkage housing of FIG. 12.
Figure 14:
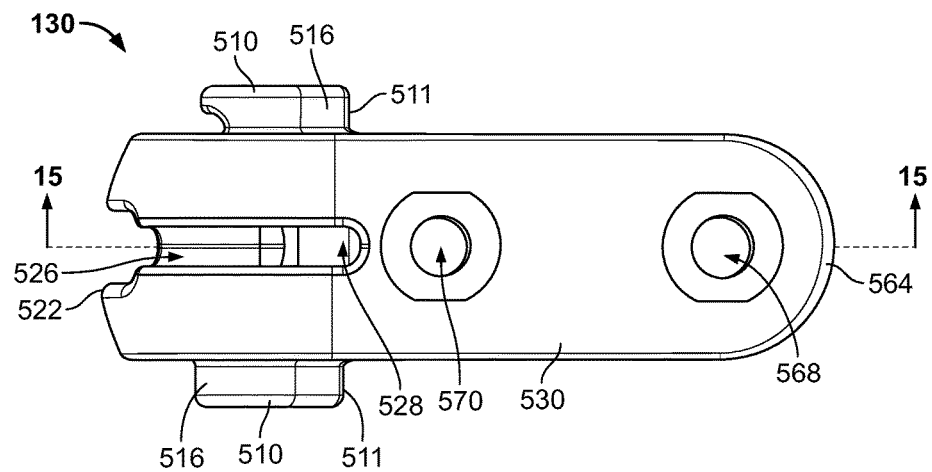
FIG. 14 is a profile view of the exemplary linkage housing of FIG. 12.
Figure 15:
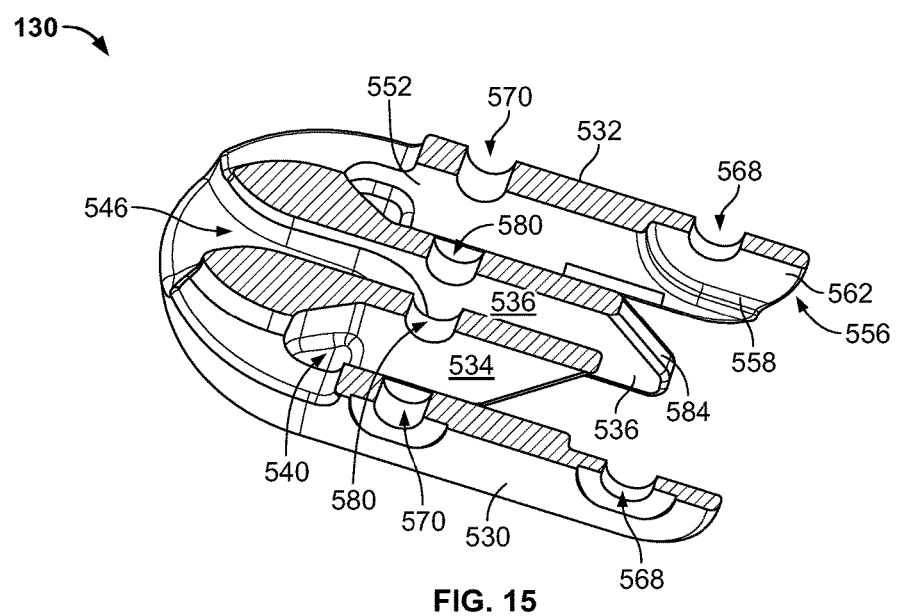
FIG. 15 is a cross-sectional view of the exemplary linkage housing of FIG. 14 taken along line 15-15.
Figure 16:
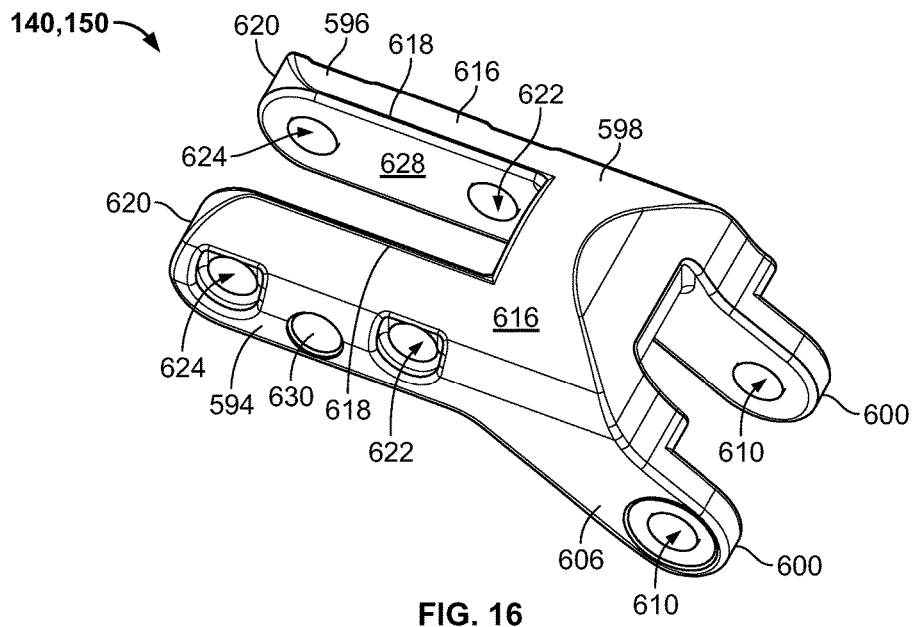
FIG. 16 is an elevated perspective view from a proximal end of an exemplary drive link in accordance with the instant disclosure.
Figure 17:
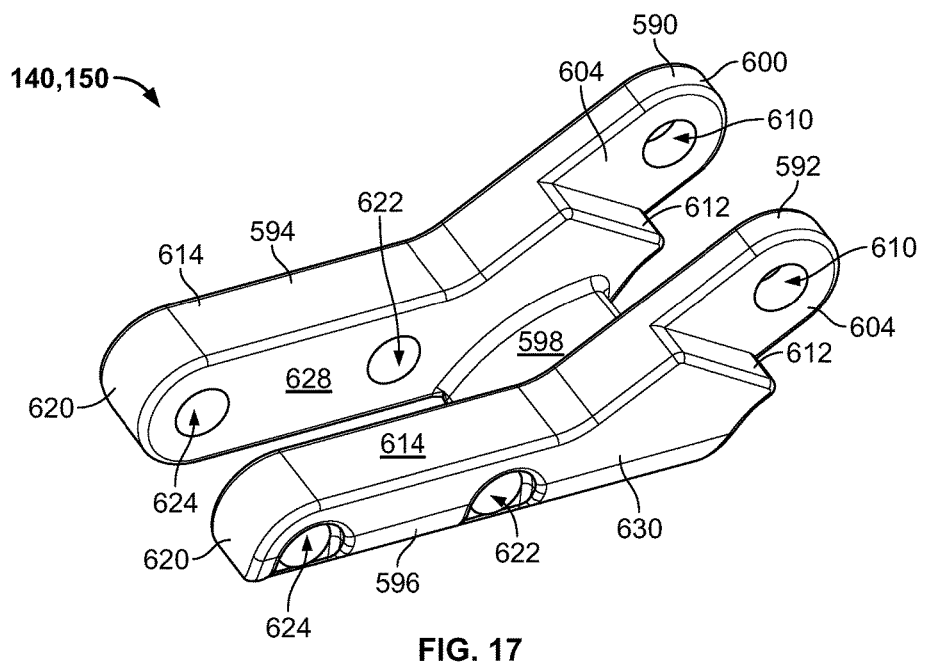
FIG. 17 is an elevated perspective view from a distal end of the exemplary drive link of FIG. 16.
Figure 18:
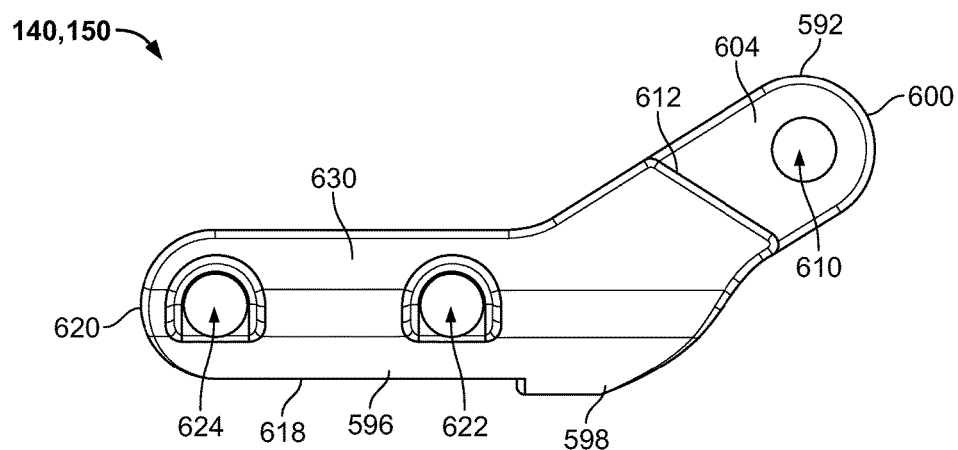
FIG. 18 is a profile view of the exemplary drive link of FIG. 16.

Each jaw 240, 250 includes a rounded proximal end 660 that transitions distally into a rectangular cross-section with a pair of openings 662, 664 extending between opposing top and bottom surfaces 666, 668 each having a cylindrical shape and being configured to receive at least one of the fifth, sixth, seventh, and eighth pins 260, 270, 290, 300 (see FIG. 2). In this fashion, the first and second jaws 240, 250 may be rotationally repositionable with respect to the drive links 140, 150 and the parallel links 180, 190. The rectangular cross-section also includes one of a series of openings 670 on an interior surface 672 in communication with a plurality of openings 674 and channels 676 formed into the opposing exterior surface 678. In this exemplary embodiment, the channels 676 are sized and configured to receive a respective deployment wire 1402, 1404, whereas the openings 670, 674 are sized to accommodate throughput of a suture retainer coupled to the left atrial occlusion clip 102. The interior surface 672 also has formed therein a LAA spring depression 676 sized and configured to receive a biasing spring of the left atrial occlusion clip 102 (see FIG. 52). This LAA spring depression 679 is in communication with a longitudinal depression 677 formed into the interior surface 672 and the bottom surface 668. And this longitudinal depression 677 is sized and configured to receive occlusion bars of the left atrial occlusion clip 102. Each jaw 240, 250 tapers longitudinally from proximal to distal after passing beyond the LAA spring depression 679 to terminate at a rounded distal end 680. As part of repositioning the jaws 240, 250 with respect to one another, the parallel links 180, 190 are also repositioned with respect to one another.

Referring to FIGS. 2 and 21-24, the first and second parallel links 180, 190 are structurally identical, but differ only in operation based upon the components mounted thereto. Consequently, the following discussion of the structure of a parallel link is applicable to both the first and second parallel links 180, 190.

Figure 24:
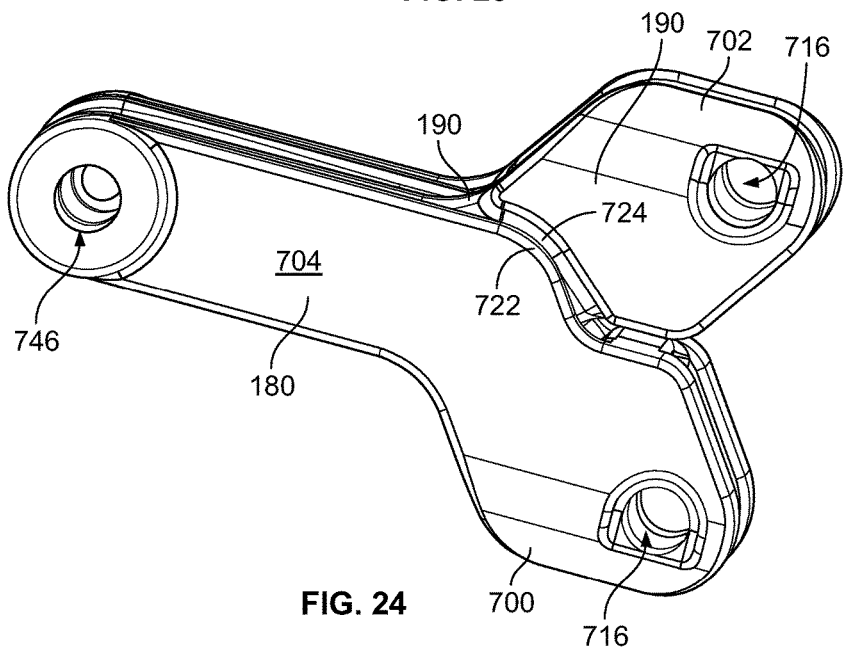
FIG. 24 is an elevated perspective view from a side showing the exemplary parallel links aligned with one another in a compact position.
Figure 25:
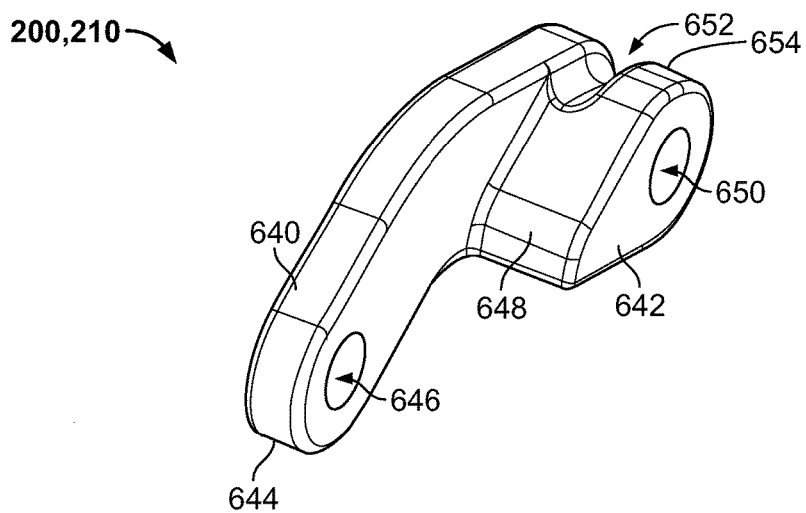
FIG. 25 is an elevated perspective view from a distal end of an exemplary toggle in accordance with the instant disclosure.
Figure 26:
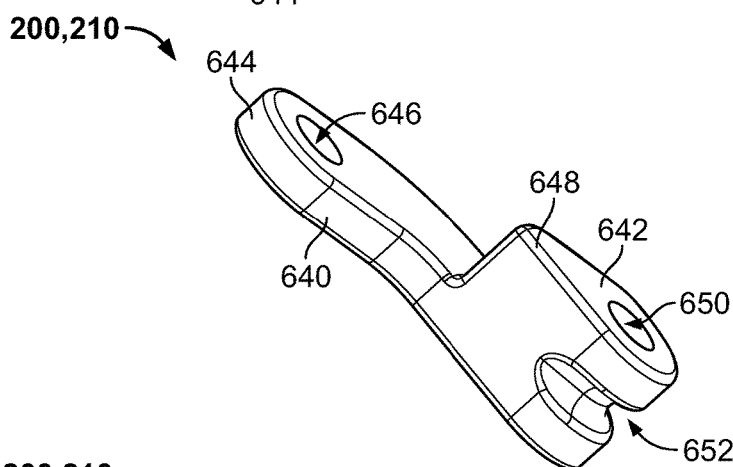
FIG. 26 is an elevated perspective view from a bottom of the exemplary toggle of FIG. 25.
Figure 27:
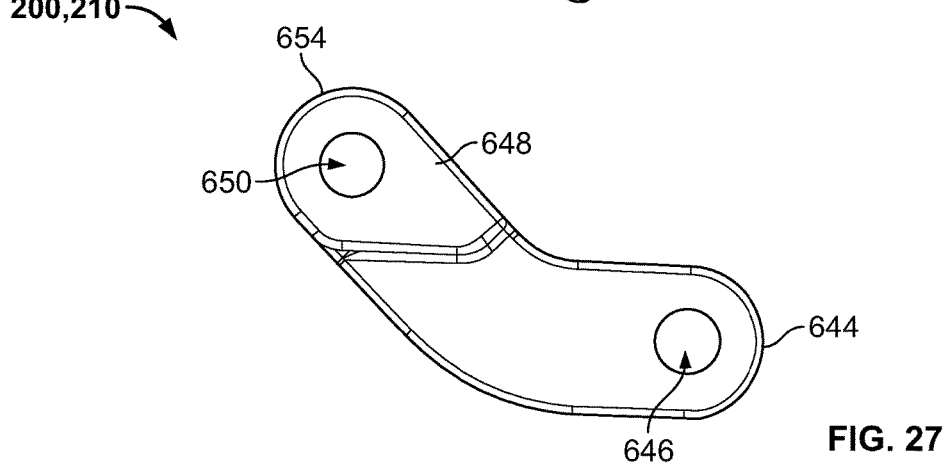
FIG. 27 is a profile view of the exemplary toggle of FIG. 25.
Figure 28:
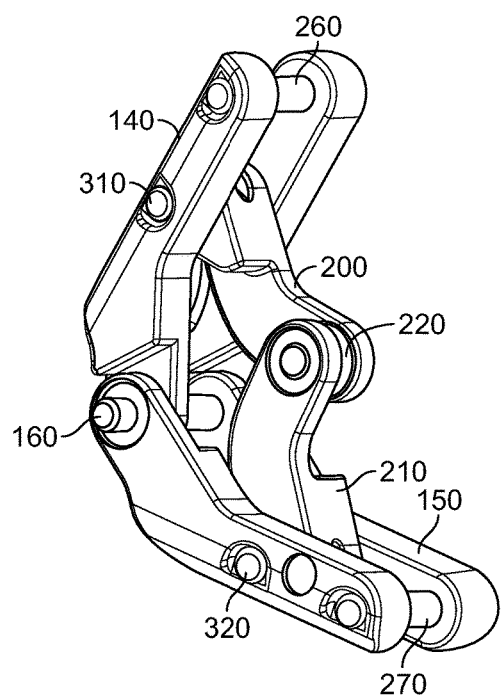
FIG. 28 is an elevated perspective view showing assembly of the toggles and drive links.
Figure 29:
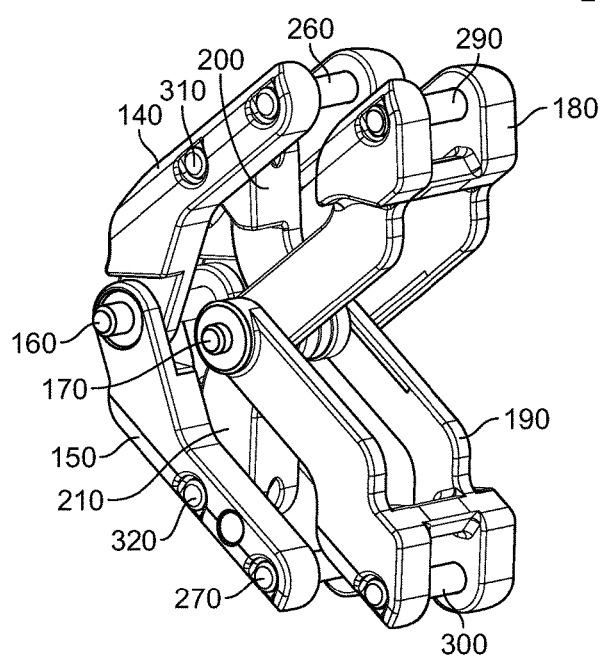
FIG. 29 is an elevated perspective view showing assembly of the toggles, parallel links, and drive links.
Figure 30:
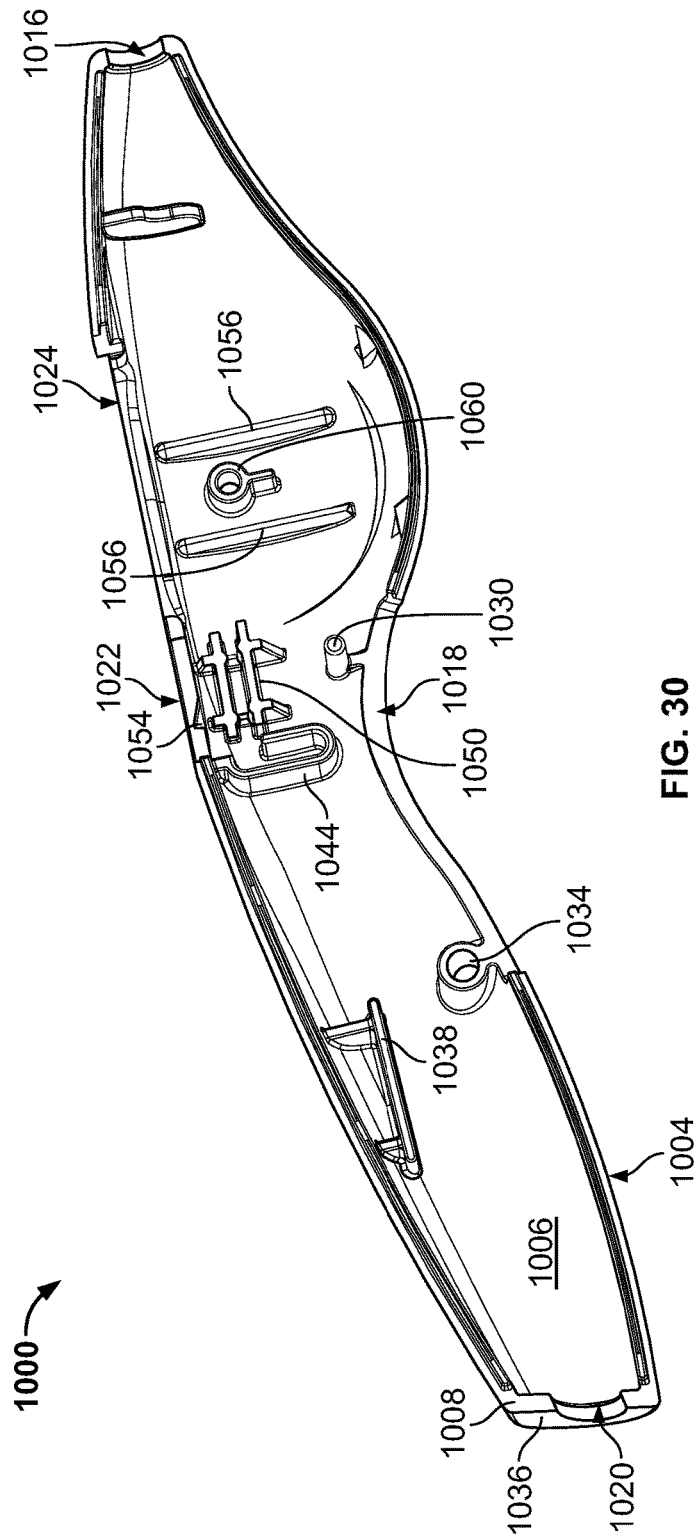
FIG. 30 is a perspective view of the interior of a left side housing in accordance with the instant disclosure.
Figure 31:
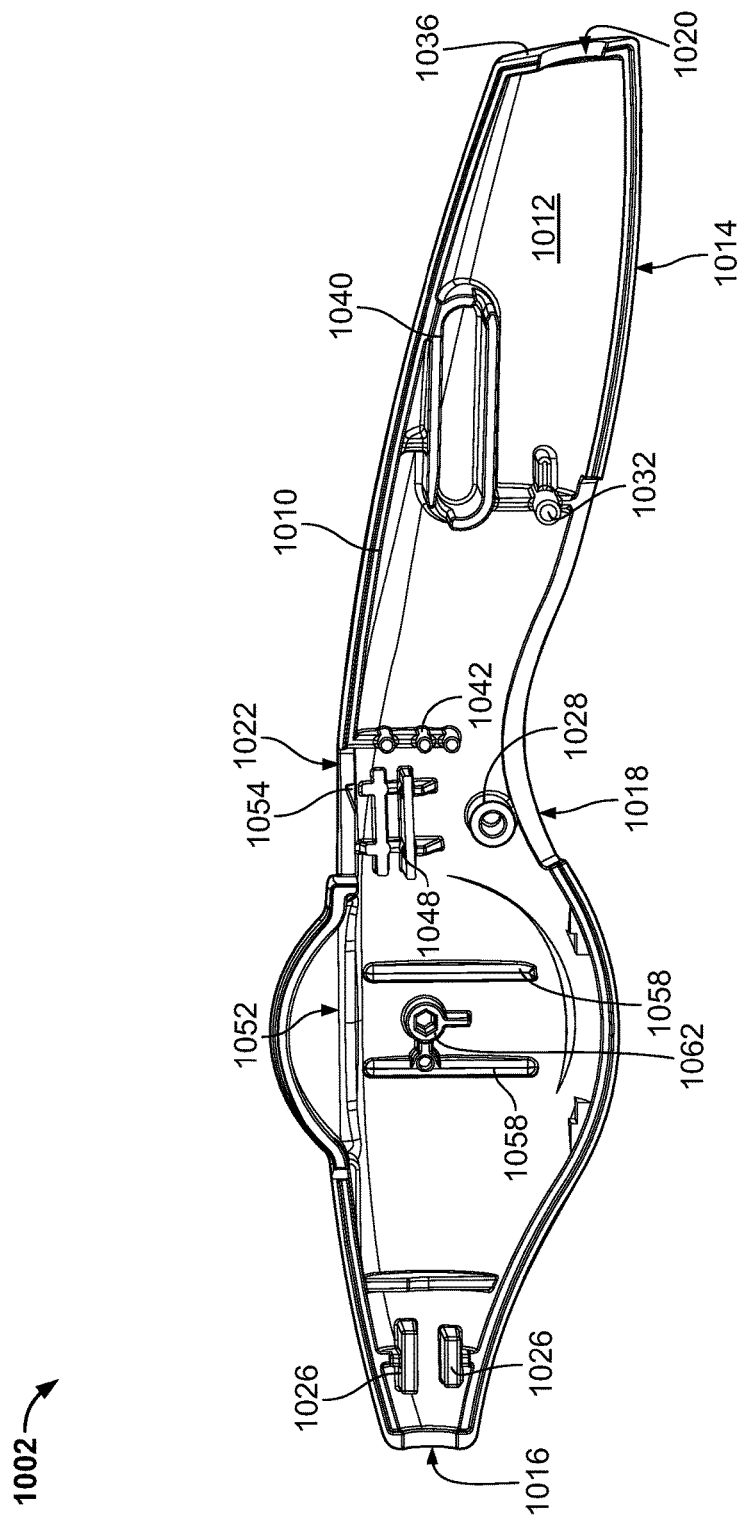
FIG. 31 is a perspective view of the interior of a right side housing in accordance with the instant disclosure.
Figure 32:
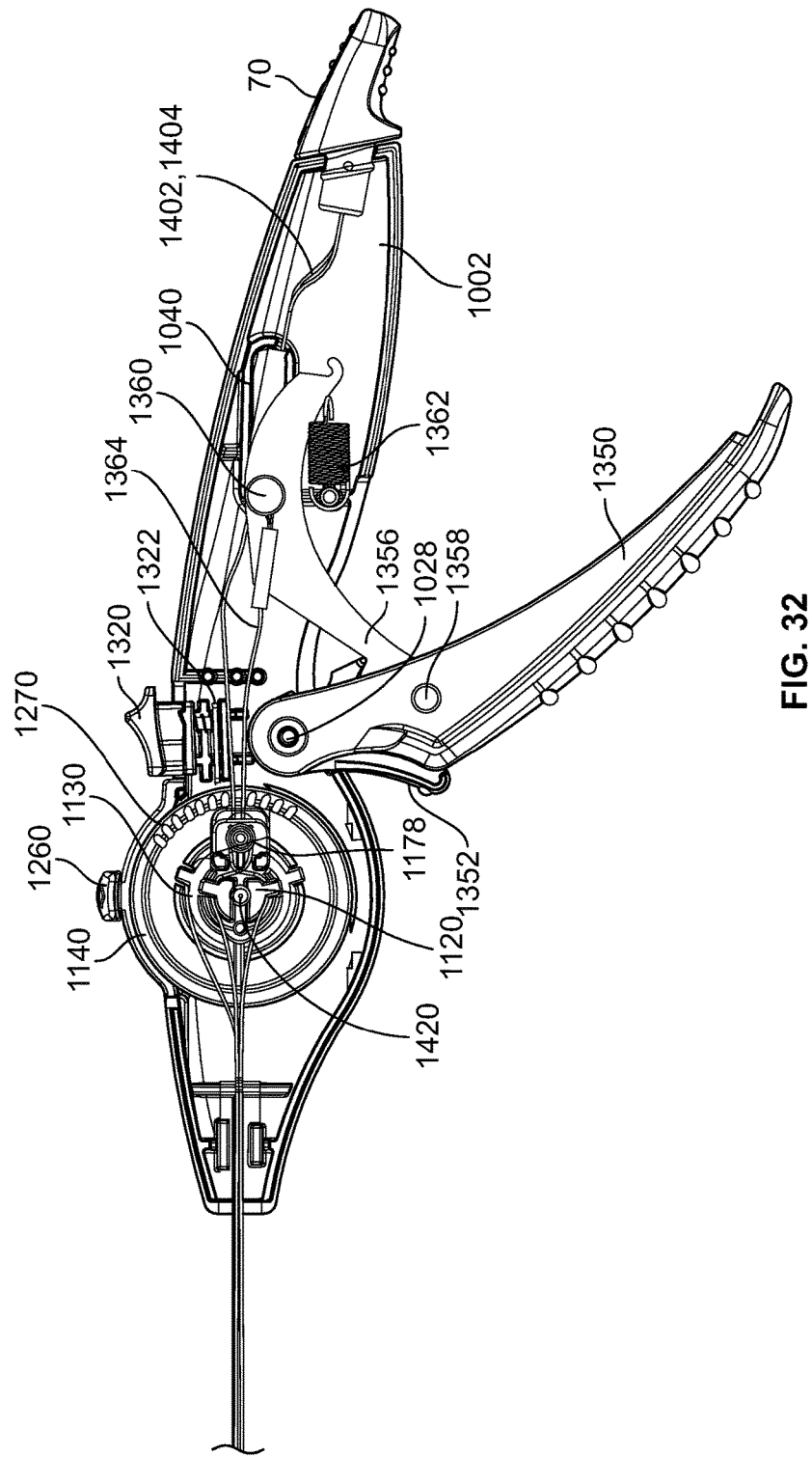
FIG. 32 is a profile view of the interior of the right side housing of FIG. 31 and components housed therein in accordance with the instant disclosure.

Each parallel link 180, 190 comprises a unitary structure including a pair of spaced apart heads 700, 702 that are angled approximately forty-five degrees with respect to corresponding longitudinal legs 704, 706. Near a base, the heads 700, 702 are joined to one another via a link 710. In exemplary form, each head 700, 702 includes a tapered proximal end 714, which is rounded at a far proximal tip, that includes a hole 716 partially bounded by opposing interior and exterior planar surfaces 718, 720, as well as an arcuate exterior surface 722. The hole 716 has a cylindrical shape that is size to accommodate throughput of at least one of the seventh and eighth pin 290, 300 and allow rotational repositioning of a respective parallel link 180, 190 around a respective jaw 240, 250. Each head 700, 702 includes an S-shaped profile 722 on one widthwise side that is configured to track an inverse S-shaped profile 724 associated with an opposite side of the same head 700, 702. In this fashion, as shown in FIG. 24 when the parallel links 180, 190 are positioned adjacent one another and the jaws 240, 250 are least spaced apart, the S-shaped contour 722 of one side of the first head 700 of the first parallel link 180 tracks the inverse S-shaped contour 724 of a second side of the second head 702 of the second parallel link 190. Each head 700, 702 also includes a width that is roughly twice the width of the corresponding longitudinal legs 704, 706. In this fashion, the portion of heads 700, 702 with the inverse S-shaped profile 724 is offset in a widthwise dimension from the corresponding longitudinal leg 704, 706.

The corresponding longitudinal legs 704, 706 extend parallel and spaced apart from one another in the widthwise direction. The only meaningful difference between the corresponding longitudinal legs 704, 706 is that the first longitudinal leg 704 includes a widthwise offset 728 that extends away from the second longitudinal leg 706 proximate the rounded distal tip 730. Each longitudinal leg includes parallel, planar inner and outer surfaces 732, 734. A first hole 736 extends through the second longitudinal leg 706 proximate the distal tip 730, that is generally equidistantly spaced from the distal tip 730 and corresponding upper and lower surfaces 740, 742. The first hole 736 has a cylindrical shape and is configured to receive at least one of the second and third pins 170, 230 in order to allow the parallel links 180, 190 to rotate with respect to the linkage housing 130. A second hole 746 extends through the first longitudinal leg 704 and offset 728 proximate the distal tip 730, that is generally equidistantly spaced from the distal tip 730 and corresponding upper and lower surfaces 740, 742. The second hole 746 has a cylindrical shape and is configured to receive at least one of the second and third pins 170, 230 in order to allow the parallel links 180, 190 to rotate with respect to the linkage housing 130.

Referring to FIGS. 1-29 and 52-57, an exemplary assembly sequence for the exemplary end effector 100 will now be described. Initially, the control and deployment wires 1172, 1174, 1272, 1274, 1364, 1402, 1404 are routed through the clevis 110. Specifically, the longitudinal passage 402 at the proximal end 404 of the clevis receives the wires 1172, 1174, 1272, 1274, 1364, 1402, 1404, which are then redirected so that the control wires 1272, 1274 individually extend through a respective through hole 410 of the clevis, while the other wires 1172, 1174, 1364, 1402, 1404 extend through the elongated through hole 412 of the clevis. After routing the wires through the clevis 110, the universal 120 is mounted to the clevis so that the projections 450 of the universal are received within respective C-shaped depressions 426. In order to retain the universal 120 in an engaged position with respect to the clevis, the control wires 1272, 1274 are individually fed through one of the cylindrical, enlarged openings 469 of the universal 120 and knotted or otherwise processed to enlarge the ends of each control wire sitting within a respective depressions 464. The control wires 1272, 1274 are then tensioned and mounted to the first wheel control 40 so that rotation of the wheel control 40 will cause pivoting motion of the universal 120 with respect to the clevis 110. Likewise, the other control wires 1172, 1174 are fed through a respective channel 476, 478 of the universal 120, while the other wires 1364, 1402, 1404 extend through the opening 474 of the universal.

After routing the wires through the universal 120, the linkage housing 130 is mounted to the universal so that the projections 510 of the linkage housing are received within respective C-shaped depressions 496. In order to retain the linkage housing 130 in an engaged position with respect to the universal 120, the control wires 1172, 1174 are individually fed through one of the openings 528 of the linkage housing and knotted or otherwise processed to enlarge the ends of each control wire sitting on the other side of the U-shaped channel 526. The control wires 1172, 1174 are then tensioned and mounted to the second wheel control 50 so that rotation of the wheel control 50 will cause pivoting motion of the linkage housing 130 with respect to the universal 120. Conversely, the other wires 1364, 1402, 1404 extend through the channel 546 of the linkage housing 130. At this point, the tilted uprights 590, 592 of the drive links 140, 150 are offset and aligned with one another to fit between the linkage housing 130 proximate the orifices 570. More specifically the holes 610 of the tilted uprights 590, 592 are longitudinally aligned with the holes 580 and the orifices 570 of the linkage housing 130 in order to receive the first pin 160, which extends completely through the linkage housing and the drive links 140, 150.

The toggles 200, 210 are also mounted to a respective drive link 140, 150, as well as concurrently to the pulley 220. Specifically, the through opening 650 of the first toggle 200 is oriented between and coaxially aligned with the openings 622 extending through the first drive link 140. When aligned, the ninth pin 310 is inserted through the openings 622, 650 to mount the first toggle 200 to the first drive link 140. Similarly, the through opening 650 of the second toggle 210 is oriented between and coaxially aligned with the openings 622 extending through the second drive link 150. When aligned, the tenth pin 320 is inserted through the openings 622, 650 to mount the second toggle 210 to the second drive link 150. The opposing ends of the toggles 200, 210 are mounted to opposing ends of the pulley 220. More specifically, each toggle through opening 646 receives a respective cylindrical lateral end of the pulley 220 in order to rotationally mount the toggles 200, 210 to the pulley. At this time, the pulley 220 is also mounted to the control wire 1364 so that repositioning of the lever control 80 is operative to reposition the pulley and correspondingly other components in order to move the jaws 240, 250 toward or away from one another in a parallel open/close fashion.

Each jaw 240, 250 is then mounted to a respective drive link 140, 150, and parallel link 180, 190. In exemplary form, a first of the openings 662 of a respective jaw 240, 250 is aligned with a respective opening 624 of a respective drive link 140, 150. After being aligned, a fifth pin 260 and a respective sixth pin 270 are inserted through the openings 624, 662 in order to pivotally mount a jaw 240, 250 to a respective drive link 140, 150. Similarly, a second of the openings 664 of a respective jaw 240, 250 is aligned with a respective hole 716 of a respective parallel link 180, 190. After being aligned, a seventh pin 290 and a respective eighth pin 300 is inserted through the openings 664, 716 in order to pivotally mount a jaw 240, 250 to a respective parallel link 180, 190. Also, the opposing ends of the parallel links 180, 190 are offset and aligned with one another to fit between the linkage housing 130 proximate the orifices 568. When aligned, second and third pins 170, 230 are mounted to individual ends of the parallel links 180, 190 and to the linkage housing 130 to provide for pivotal motion between the parallel links and the linkage housing. Before, during, or after mounting the jaws 240, 250 to the drive links 140, 150 and the parallel links 180, 190, the deployment wires 1402, 1404 are respectively directed through openings 674 of the jaws 240, 250 so that the user control 20 may be manipulated to deploy the LAA occlusion clip 102.

Turning to FIGS. 1, 2, and 30-32, a more detailed discussion of the user control 20, the first wheel control 40, the second wheel control 50, the repositionable lock 60, the repositionable tab 70, the lever control 80, and the grip housing 90 follows.

The grip housing 90 comprises respective left and right side housing halves 1000, 1002. The left side housing 1000 includes a generally convex exterior surface 1004 and an opposite interior concave surface 1006. The interior and exterior surfaces 1004, 1006 join one another at a peripheral surface 1008 that delineates the general outline of the left side housing 1000. This left side peripheral surface 1008 cooperates with a right side peripheral surface 1010 (which bridges opposing interior and exterior surfaces 1012, 1014 of the right side housing 1002) to delineate five openings 1016-1024 that allow through put of various components. It should be noted that the left side housing peripheral surface 1008 includes a lip that is correspondingly received within a recess of the right side housing peripheral surface 1010 to facilitate alignment of the housings when mounted to one another. More specifically, the right side peripheral surface 1010 partially overlaps the left side peripheral surface 1008 when the housings are mounted to one another as shown in FIG. 1.

By way of example, a first opening 1016 occurs at a distal end of the housings 1000, 1002 and is sized and shaped in a circular fashion to circumscribe and retain a proximal portion of the elongated cylindrical shaft 30. As will be discussed in greater detail hereafter, the elongated cylindrical shaft 30 includes longitudinal cut-outs 1392 that receive a pair of retention plates 1026 extending from the interior surface 1012 of the right side housing 1002.

The second opening 1018 occurs on an underside of the housing halves 1000, 1002. This second opening 1018 is sized to accommodate a portion of the lever control 80. Inset from a distal end of the second opening is an integral, hollow axle 1028 extending from the interior surface 1012 of the right side housing 1002. As will be discussed in more detail hereafter, a portion of the lever control 80 rotates about the axle 1028 when the lever control is repositioned. In order to retain this portion of the lever control rotating about the axle 1028, the left side housing 1000 includes a retention pin 1030 that is received by the hollow axle 1028 and operates to mount adjacent portions of the housings 1000, 1002 to one another. Inset from a proximal end of the second opening is an integral spring retainer projection 1032 extending from the interior surface 1012 of the right side housing 1002. As will be discussed in more detail hereafter, a spring of the lever control 80 is mounted to the spring retainer projection 1032. In order to retain the spring mounted to the spring retainer projection 1032, the left side housing 1000 includes a retention cylinder 1034 that is hollow and sized to receive the spring retainer projection 1032 and mount adjacent portions of the housings 1000, 1002 to one another.

Figure 50:
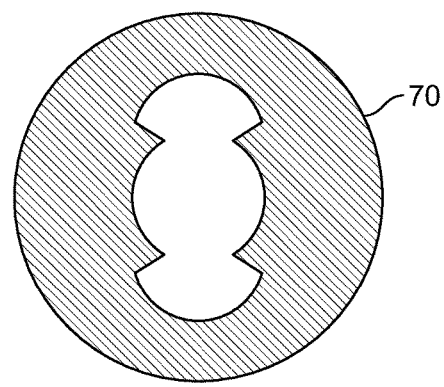
FIG. 50 is an end view taken from a distal end of an exemplary repositionable tab in accordance with the instant disclosure.
Figure 51:
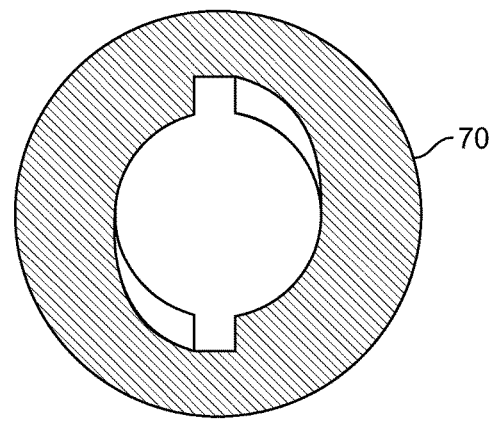
FIG. 51 is an end view taken from a distal end of another exemplary repositionable tab in accordance with the instant disclosure.
Figure 52:
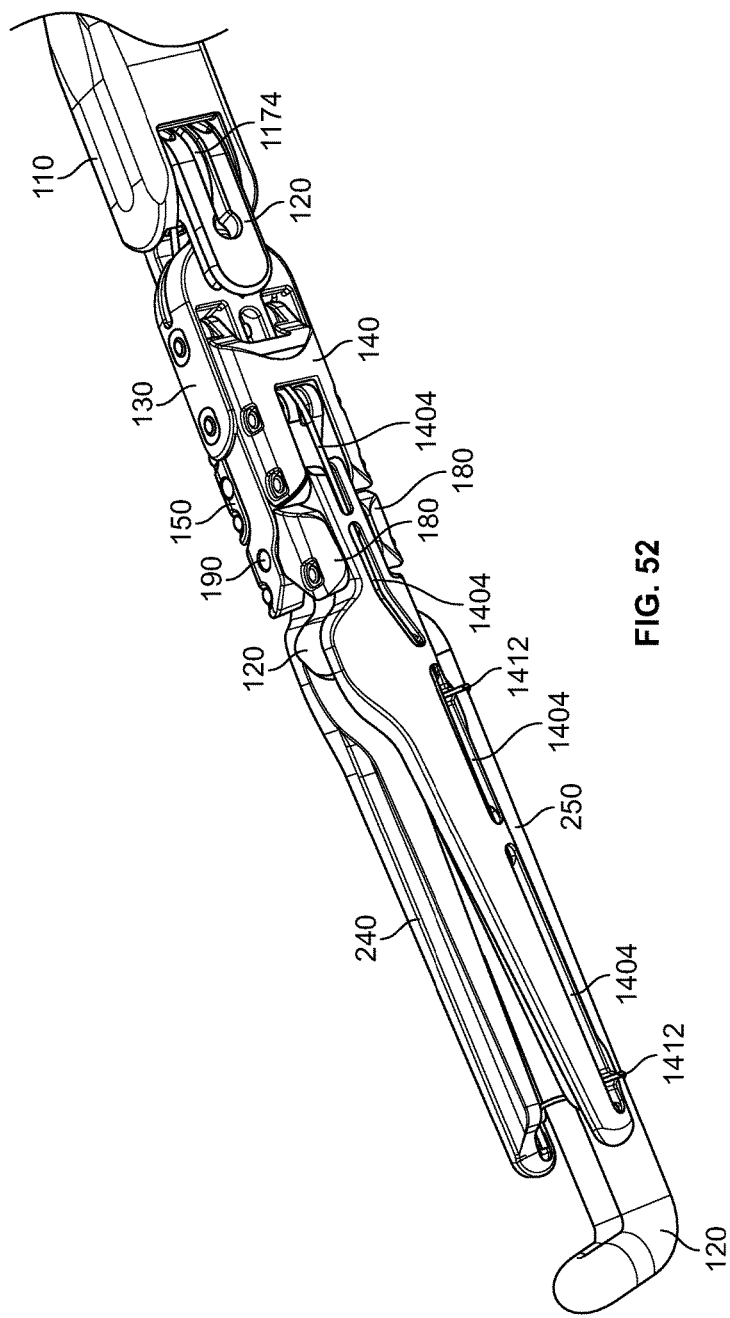
FIG. 52 is an elevated perspective view of an exemplary end effector having mounted thereto an occlusion clip in a closed position.
Figure 53:
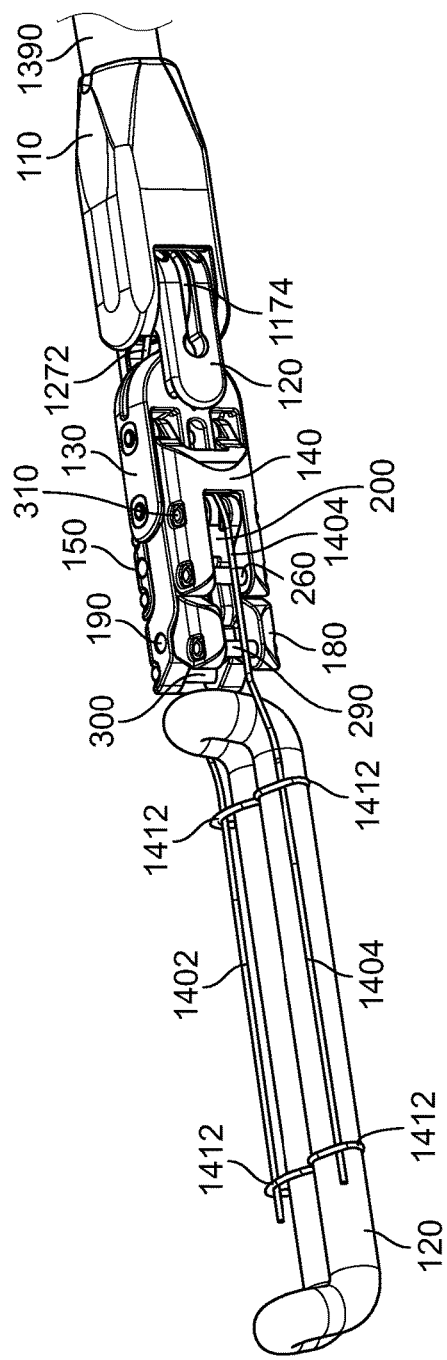
FIG. 53 is an elevated perspective view of the exemplary end effector and occlusion clip of FIG. 52 shown without repositionable jaws.
Figure 54:
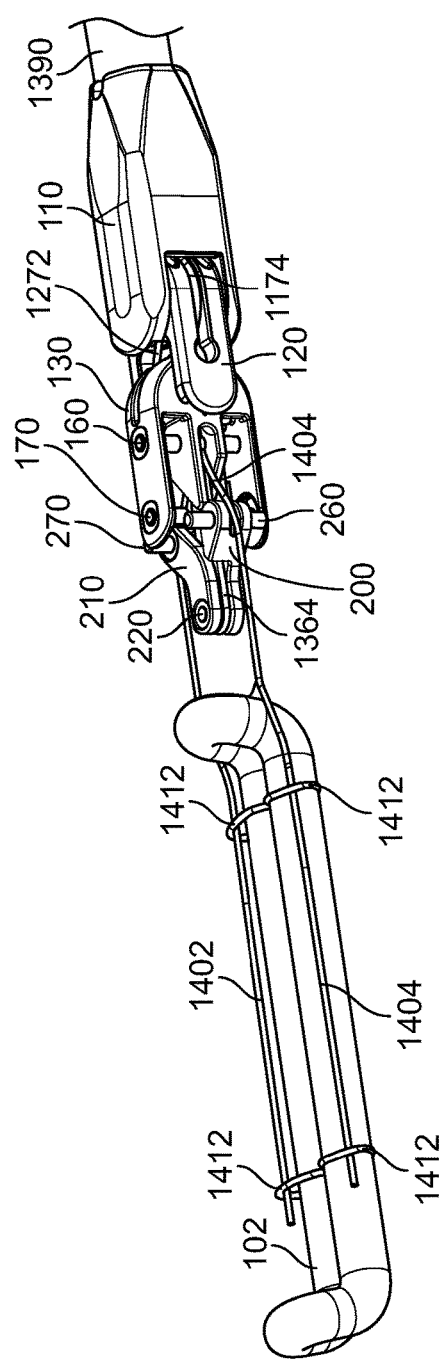
FIG. 54 is an elevated perspective view of the exemplary end effector and occlusion clip of FIG. 52 shown without repositionable jaws, first and second drive links, and first and second parallel links.
Figure 55:
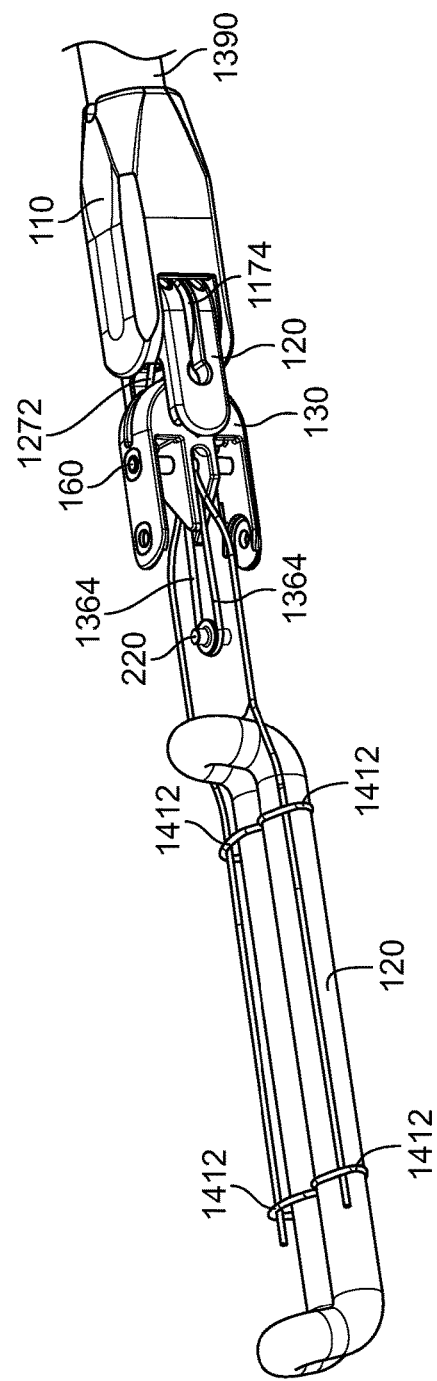
FIG. 55 is an elevated perspective view of the exemplary end effector and occlusion clip of FIG. 52 shown without repositionable jaws, first and second drive links, first and second parallel links, and first and second toggles.
Figure 56:
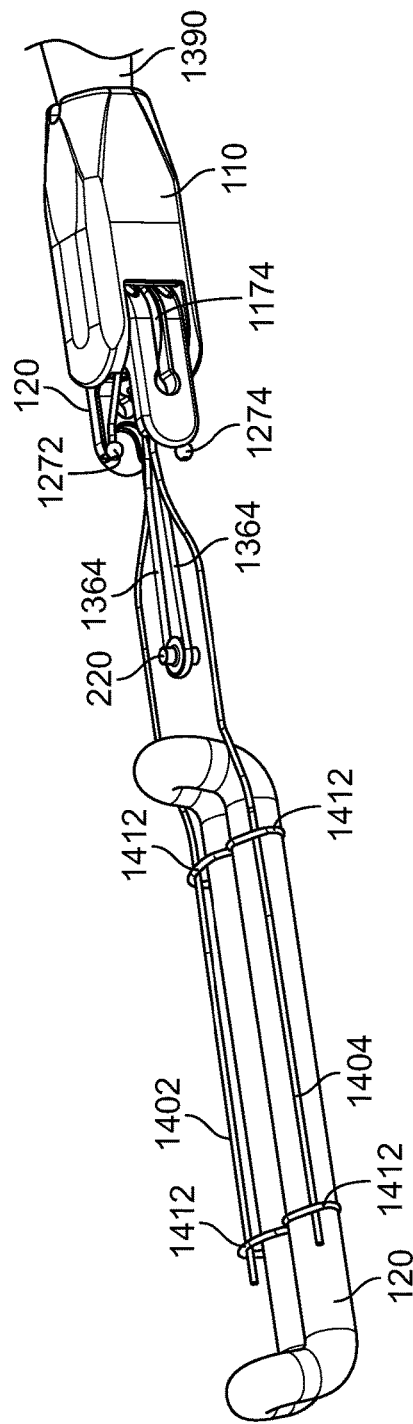
FIG. 56 is an elevated perspective view of the exemplary end effector and occlusion clip of FIG. 52 shown without repositionable jaws, first and second drive links, first and second parallel links, first and second toggles, and linkage housing.

The third opening 1020 occurs at a proximal end 1036 of the housings 1000, 1002 and is sized to receive a portion of the repositionable tab 70. By way of example, the third opening 1020 is circular in nature and sized to retain a cylindrical portion of the repositionable tab 70 as part of a friction fit that may be overcome by a user withdrawing the tab from a cylindrical portion from the grip housing 90. It should be noted, however, that other shapes besides circular openings may be used as part of the third opening 1020. As shown in FIGS. 50 and 51, the repositionable tab 70 may embody any number of shapes including, without limitation, an hourglass shape (see FIG. 50), a helical thread shape (see FIG. 51) and a triangular shape that requires rotation of the repositionable tab 70 with respect to the grip housing 90 in order to insert and extract the repositionable tab from the grip housing.

Extending distally from the third opening 1020, the left side housing 100 includes a linear projection 1038, extending proximal to distal, that is configured to guide motion of a portion of the lever control 80. Generally opposite this linear projection 1038, extending from the interior surface 1012 of the right side housing 1002 is an oblong, hollow ridge 1040 that is sized to receive a portion of the lever control 80, yet allow this portion of the lever control to move therein within a predetermined range of motion.

Above the second opening 1018 and extending proximally from the fourth opening 1022 of the right side housing 1002 interior surface 1012 is a control wire guide 1042 comprising three cylindrical projections spaced apart from one another vertically to allow a first gap between the first and second projections and a second gap between the second and third projections. As will be discussed in more detail hereafter, a control wire coupled to the lever control 80 extends between the second and third projections, while a pair of deployment wires coupled to the repositionable tab 70 extends between the first and second projections. In order to ensure the control wire and deployment wires stay in the aforementioned gaps, the left side housing 1000 includes ring 1044 extending from the interior surface 1006 that circumscribes the control wire guide 1042 to retain the wires within a respective gap.

The fourth opening 1022 occurs on a top side of the housings halves 1000, 1002. This opening 1022 is sized to accommodate a portion of the repositionable lock 60. Positioned underneath the bounds of the fourth opening 1022 are complementary left and right ledges 1048, 1050 upon which the repositionable lock 60 sits. Each of the housing halves 1000, 1002 also includes a triangular cavity 1054 that is configured to receive a portion of the repositionable lock 60.

A fifth opening 1024 also occurs on a top side of the housing halves 1000, 1002 and distal to the fourth opening 1022. This fifth opening 1024 is sized to accommodate a portion of the first wheel control 40. In particular, a portion of the first wheel 1110 and the control knob 1160 extend above the housings 1000, 1002 in order to allow a user to manipulate the control knob and resultantly rotate the first wheel.

Adjacent the fifth opening is a sixth opening 1052 that extends completely though the top surface of the right side housing 1002. Interposing the fifth and sixth openings 1024, 1052 is an arcuate divider comprised exclusively of the right side housing 1002. This sixth opening 1052 is sized to accommodate a portion of the second wheel control 50. In particular, a portion of the second wheel 1140 and the control knob 1260 extend above the housing 1002 in order to allow a user to manipulate the control knob and resultantly rotate the second wheel.

Extending outward from the interior surface 1006 of the left side housing 1000 is a pair of vertical guides 1056 that mirror a pair of vertical guides 1058 extending from the interior surface 1012 of the right side housing 1002. The left side vertical guides 1056 are adapted to contact the exterior track 1152 of the first wheel 1110 and allow the track to rotationally slide against the vertical guides. Similarly, the right side vertical guides 1058 are adapted to contact the exterior track 1252 of the second wheel 1140 and allow the track to rotationally slide against the vertical guides. In this fashion, the vertical guides 1056, 1058 act as lateral boundaries for the wheels 1110, 1140 as well as the pulleys 1120, 1130. Interposing the vertical guides 1056, 1058 are respective hollow cylinders 1060, 1062 extending from respective interior surfaces 1006, 1012. Each hollow cylinder 1060, 1062 is sized to receive a portion of an axle 1420 that extends through the wheels 1110, 1140 and the pulleys 1120, 1130. Though not necessary, the dimensions of each hollow cylinder 1060, 1062 may be such that the axle 1420 is retained therein via a friction fit and the axle is unable to rotate with respect to the hollow cylinders, but still allow the wheel controls 40, 50 to be repositioned.

As discussed previously, the user control 20 includes a first wheel control 40 to vary the yaw of the end effector 100, while the user control 20 further includes a second wheel control 50 to vary the pitch of the end effector. In order to selectively inhibit manipulation of the wheel controls 40, 50, a repositionable lock 60 is also provided. A proximal end of the user control 20 further includes a repositionable tab 70 that may be utilized to, in exemplary form, disengage a left atrial appendage (LAA) occlusion clip 102 from the end effector 100. In addition, the user control 20 includes a lever control 80 that is operative to control repositioning of the jaws 240, 250 of the end effector 100 with respect to one another. Several of the components of the lever control 80, the wheel controls 40, 50, and the repositionable lock 60 at least partially reside within a grip housing 90.

As shown in FIGS. 32-42, the first and second wheel controls 40, 50 rotate about an axle 1420 received within corresponding cylindrical cavities 1024, 1056 formed within the right and left side housing halves 1000, 1002. The axle 1420 is cylindrical in shape and extends through the center of a first wheel 1110, a first pulley 1120, a second pulley 1130, and a second wheel 1140. The first wheel 1110 and the first pulley 1120 are components of the first wheel control 40, whereas the second wheel 1140 and the second pulley 1130 are components of the second wheel control 50.

Figure 33:
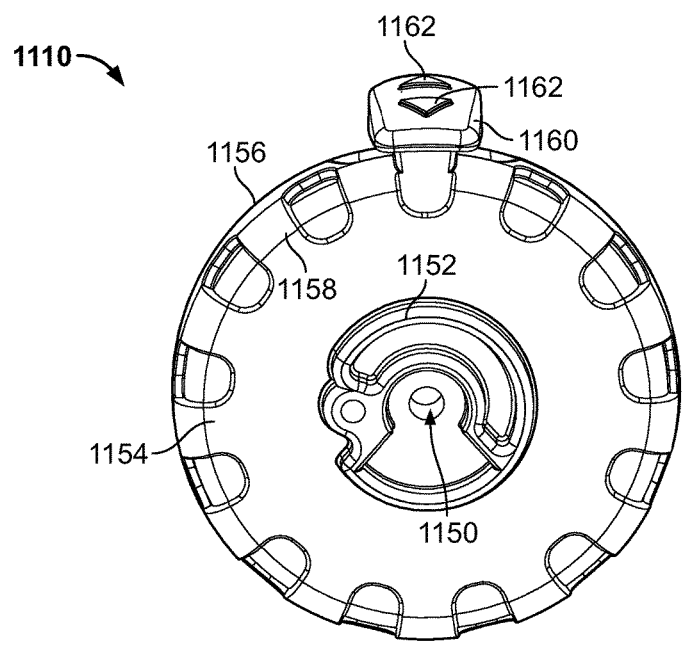
FIG. 33 is an elevated perspective view of an exterior side of a first wheel in accordance with the instant disclosure.
Figure 34:
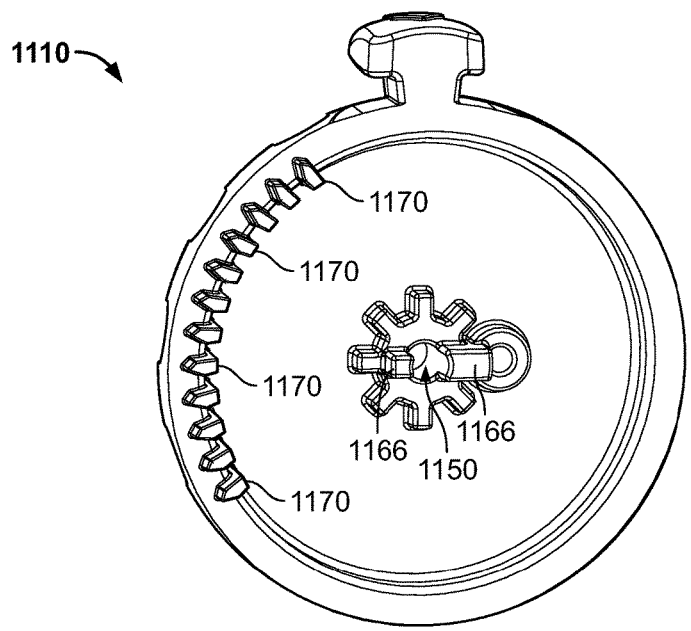
FIG. 34 is an elevated perspective view of an interior side of the first wheel of FIG. 33.

In exemplary form, referring to FIGS. 33 and 34, the first wheel 1110 comprises a unitary structure having a generally circular shape and including a central opening 1150 accommodating throughput of the axle 1420. Radially outward from this opening 1150 and partially circumscribing the opening is a track 1152 extending outward from an exterior, side surface 1154. Adjacent this exterior, side surface 1154 is a peripheral surface 1156, with an arcuate transition surface 1158 interposing the side and circumferential surfaces. Extending radially outward from the peripheral surface 1156 is a control knob 1160 with indicia 1162 on the top of the control knob providing a user with an indication that rotation of the first wheel 1110 is operative to reposition the end effector 100 laterally within an X-Y plane. In order to transfer rotation of the first wheel 1110 into lateral motion of the end effector, the first wheel also includes a pair of protrusions 1166 on opposing radial sides of the opening 1150. As will be discussed in more detail hereafter, these protrusions 1166 are received within corresponding pockets of the first pulley 1120 so that rotational motion of the first wheel 1110 is transferred into rotational motion of the first pulley. Radially outset from the opening 1150 and one of the protrusions 1166 are a plurality of teeth 1170 circumferentially inset and distributed about ninety degrees of the circumference.

Figure 35:
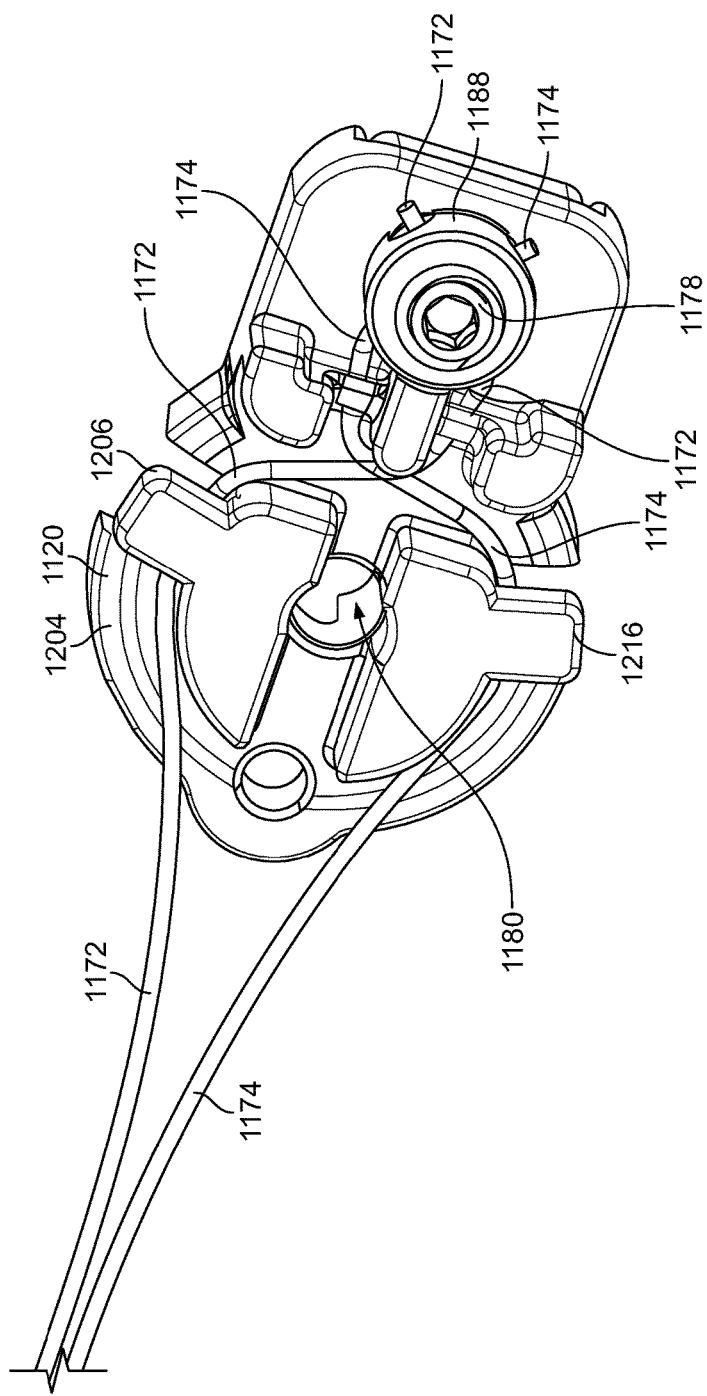
FIG. 35 is an elevated perspective view from an exterior surface of a first pulley and associated wires in accordance with the instant disclosure.
Figure 36:
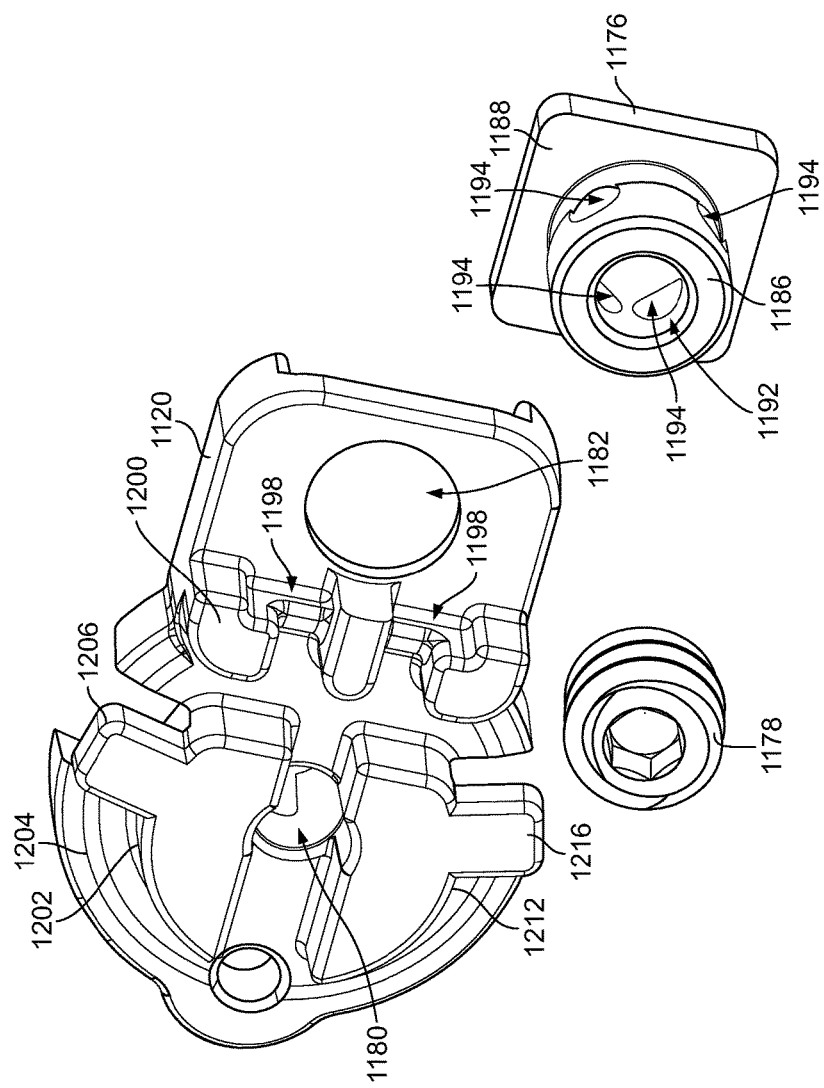
FIG. 36 is an exploded view of the components of FIG. 35, less the wires.
Figure 37:
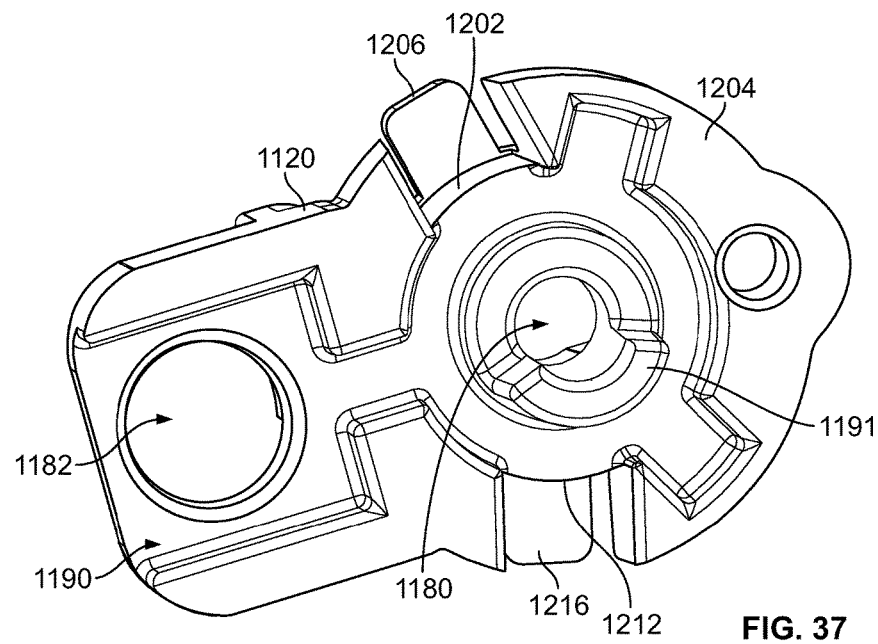
FIG. 37 is an elevated perspective view from an interior surface of the first pulley of FIG. 35.
Figure 38:
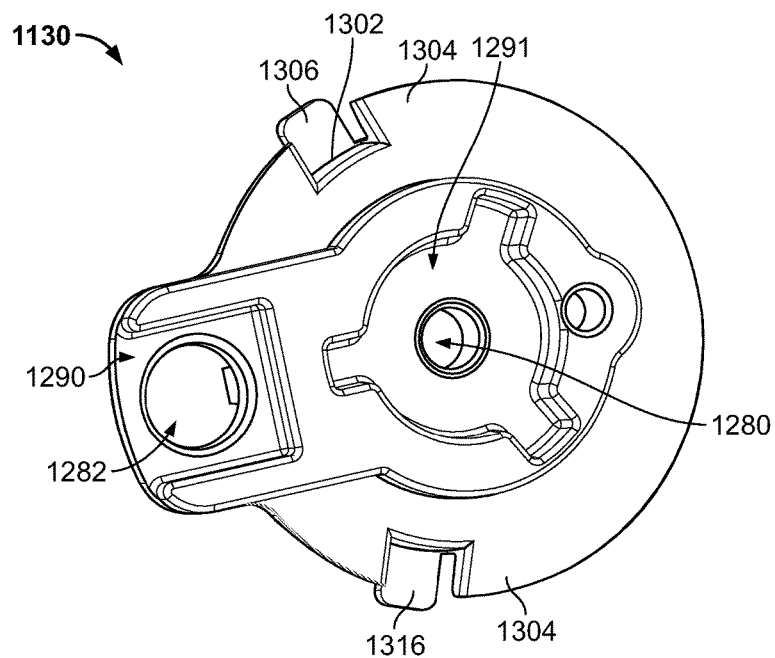
FIG. 38 is an elevated perspective view from an exterior surface of a second pulley in accordance with the instant disclosure.
Figure 39:
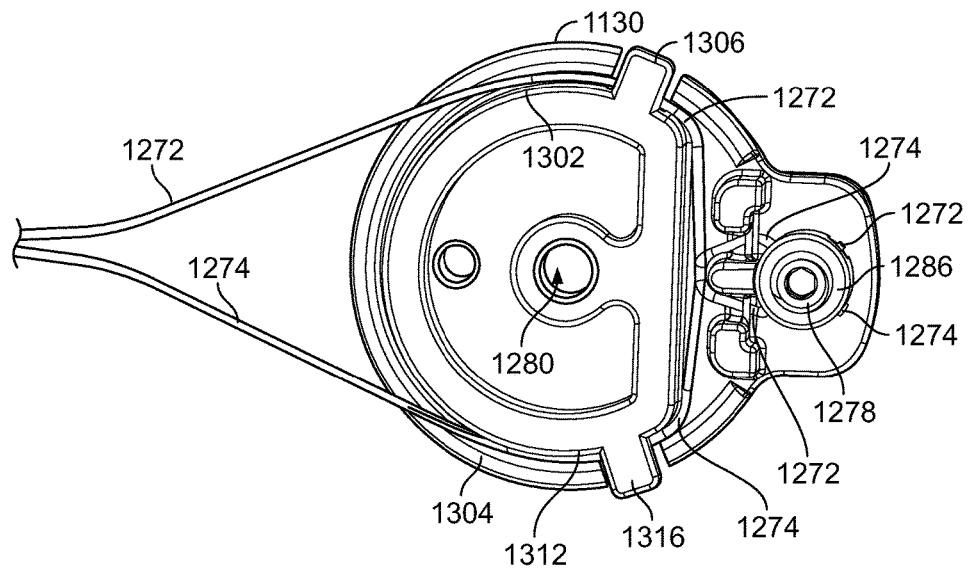
FIG. 39 is an elevated perspective view from an interior surface of a second pulley and associated wires in accordance with the instant disclosure.
Figure 40:
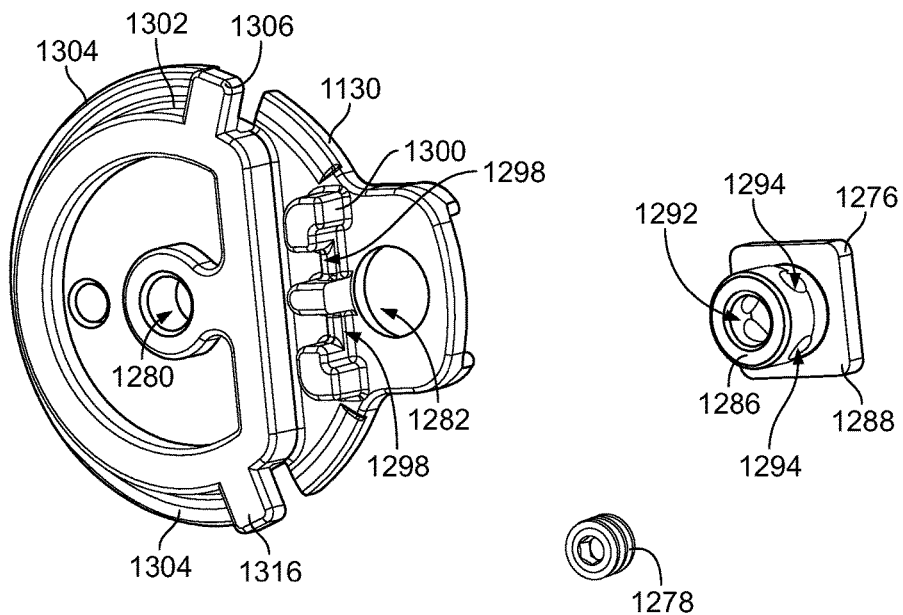
FIG. 40 is an exploded view of the components of FIG. 39, less the wires.
Figure 41:
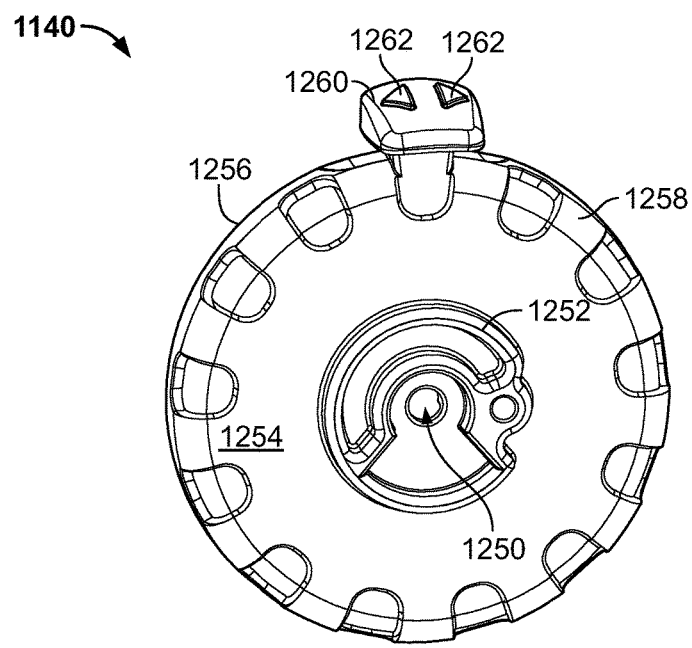
FIG. 41 is an elevated perspective view of an exterior side of a second wheel in accordance with the instant disclosure.
Figure 42:
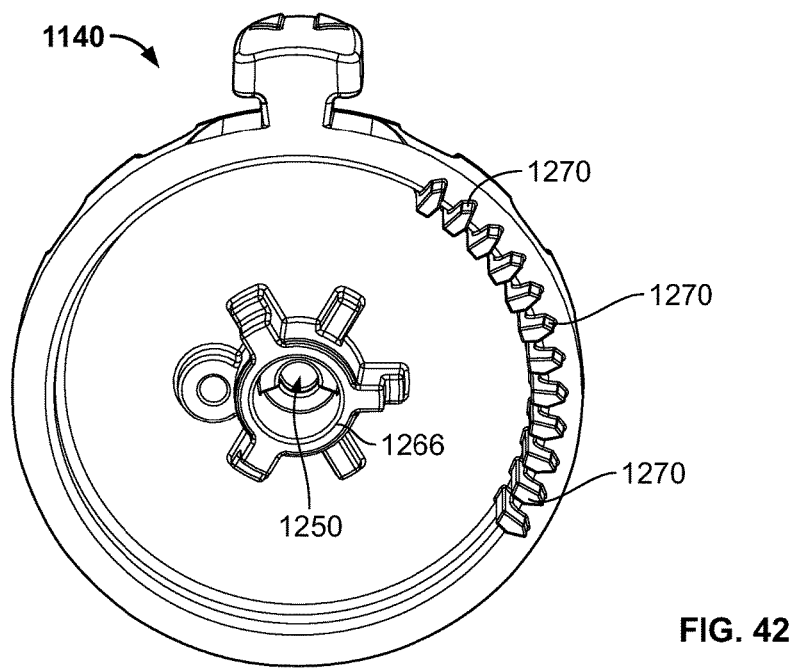
FIG. 42 is an elevated perspective view of an interior side of the second wheel of FIG. 41.

Referring to FIGS. 35-37, a second component of the first wheel control 40, the first pulley 1120, is operative to convert rotational motion of the first wheel 1110 into longitudinal motion of at least one of a first pair of control wires 1172, 1174. The control wires 1172, 1174 are mounted to the first pulley 1120 using a clamp plate 1176 and a set screw 1178. In exemplary form, the first pulley 1120 includes a first through opening 1180 sized and configured to receive throughput of the axle 1420 so that the first pulley may rotate about the axle, in addition to a second through opening 1182 sized and configured to receive an upstanding cylinder 1186 of the clamp plate 1176. But the second through opening 1182 is too small to allow throughput of a backing plate 1188 of the clamp plate 1176. Accordingly, a rear of the first pulley 1120 includes a recess 1190 sized and configured to receive the backing plate 1188 and inhibit rotation of the backing plate with respect to the first pulley 1120. The rear of the first pulley 1120 also includes a semi-circular spacer 1191 partially delineating the first through opening and extending laterally away from a center of the first pulley. The spacer 1191 is operative to provide a gap between the first and second pulleys 1120, 1130.

The upstanding cylinder 1186 includes an axial through opening 1192 that is threaded to engage the threads of the set screw 1178, as well as four radial openings 1194 that are sized and configured to receive at least one of the control wires 1172, 1174. By way of example, the four radial openings 1194 are circular and radially distributed to be equidistantly spaced from one another about the circumference of the upstanding cylinder 1186. A first and second of the radial openings 1194 are located proximate first and second openings 1198 extending through a wall 1200 extending laterally outward and adjacent the second through opening 1182.

In exemplary form, the first control wire 1172 is routed over a first arcuate surface 1202 that extends laterally outward from the first pulley 1120 so that the free end of the first control wire interposes between a radial wall 1204 and a first guide 1206. The free end of the first control wire 1172 is then directed through a bottom opening (second opening) 1198 and directed through the nearest radial opening 1194. After passing beyond the nearest radial opening, the free end of the first control wire 1172 is passed through the radial opening opposite (180 degrees opposed) from the radial opening the first control wire already extends through. Similarly, the second control wire 1174 is routed over a second arcuate surface 1212 that extends laterally outward from the first pulley 1120 so that the free end of the second control wire interposes between the radial wall 1204 and a second guide 1216. The free end of the second control wire 1174 is then directed through a top opening (first opening) 1198 and directed through the nearest radial opening 1194. After passing beyond the nearest radial opening, the free end of the second control wire 1174 is passed through the radial opening opposite (180 degrees opposed) from the radial opening that the first control wire already extends through. After both control wires 1172, 1174 have passed through the radial openings 1194, the set screw 1178 is threaded into the axial through opening 1192 to crimp the control wires in place. This crimping operation is undertaken while both control wires 1172, 1174 are put into a predetermined amount of tension and the end effector 100 is in a neutral position within the X-Y and Y-Z planes.

Turning to FIGS. 38-42, the second wheel 1140 of the second wheel control 50 comprises a unitary structure having a generally circular shape and including a central opening 1250 accommodating throughput of the axle 1420. Radially outward from this opening 1250 and partially circumscribing the opening is a track 1252 extending outward from an exterior, side surface 1254. Adjacent this exterior, side surface 1254 is a peripheral surface 1256, with an arcuate transition surface 1258 interposing the side and circumferential surfaces. Extending radially outward from the peripheral surface 1256 is a control knob 1260 with indicia 1262 on the top of the control knob providing a user with an indication that rotation of the second wheel 1140 is operative to reposition the end effector 100 vertically within a Y-Z plane. In order to transfer rotation of the second wheel 1140 into vertical motion of the end effector 100, on an opposite side of the second wheel is a cylindrical projection 1266 with three spokes equidistantly spaced from one another and radially extending around the opening 1250. As will be discussed in more detail hereafter, the cylindrical projection 1266 and spokes are received within corresponding pockets of the second pulley 1130 so that rotational motion of the second wheel 1140 is transferred into rotational motion of the second pulley. Radially outset from the opening 1250 and the cylindrical projection 1266 are a plurality of teeth 1270 circumferentially inset and distributed about ninety degrees of the circumference.

A second component of the second wheel control 50, the second pulley 1130, is operative to convert rotational motion of the second wheel 1140 into longitudinal motion of at least one of a first pair of control wires 1272, 1274. The control wires 1272, 1274 are mounted to the second pulley 1130 using a clamp plate 1276 and a set screw 1278. In exemplary form, the second pulley 1130 includes a first through opening 1280 sized and configured to receive throughput of the axle 1420 so that the second pulley may rotate about the axle, in addition to a second through opening 1282 sized and configured to receive an upstanding cylinder 1286 of the clamp plate 1276. But the second through opening 1282 is too small to allow throughput of a backing plate 1288 of the clamp plate 1276. Accordingly, a front of the second pulley 1130 includes a recess 1290 sized and configured to receive the backing plate 1288 and inhibit rotation of the backing plate with respect to the second pulley 1130. The front of the second pulley 1130 also includes a depression 1291 that is sized to receive the cylindrical projection 1266 and the spokes of the second wheel 1140.

The upstanding cylinder 1286 of the clamp plate 1276 includes an axial through opening 1292 that is threaded to engage the threads of the set screw 1278, as well as four radial openings 1294 that are sized and configured to receive at least one of the control wires 1272, 1274. By way of example, the four radial openings 1294 are circular and radially distributed to be equidistantly spaced from one another about the circumference of the upstanding cylinder 1286. A first and second of the radial openings 1294 are located proximate first and second openings 1298 extending through a wall 1300 extending laterally outward and adjacent the second through opening 1282.

In exemplary form, the first control wire 1272 is routed over a first arcuate surface 1302 that extends laterally outward from the second pulley 1140 so that the free end of the first control wire interposes between a radial wall 1304 and a first guide 1306. The free end of the first control wire 1272 is then directed through a bottom opening (second opening) 1298 and directed through the nearest radial opening 1294. After passing beyond the nearest radial opening, the free end of the first control wire 1272 is passed through the radial opening opposite (180 degrees opposed) from the radial opening that the first control wire already extends through. Similarly, the second control wire 1274 is routed over a second arcuate surface 1312 that extends laterally outward from the second pulley 1140 so that the free end of the second control wire interposes between the radial wall 1304 and a second guide 1316. The free end of the second control wire 1274 is then directed through a top opening (first opening) 1298 and directed through the nearest radial opening 1294. After passing beyond the nearest radial opening, the free end of the second control wire 1274 is passed through the radial opening opposite (180 degrees opposed) from the radial opening the first control wire already extends through. After both control wires 1272, 1274 have passed through the radial openings 1294, the set screw 1278 is threaded into the axial through opening 1292 to crimp the control wires in place. This crimping operation is undertaken while both control wires 1272, 1274 are put into a predetermined amount of tension and the end effector 100 is in a neutral position within the Y-Z plane. After crimping, rotation of the wheels 1110, 1140 is operative to change the lateral and vertical position of the end effector 100. And these positions when achieved by user manipulation to a predetermined location may be retained using the repositionable lock 60.

Figure 43:
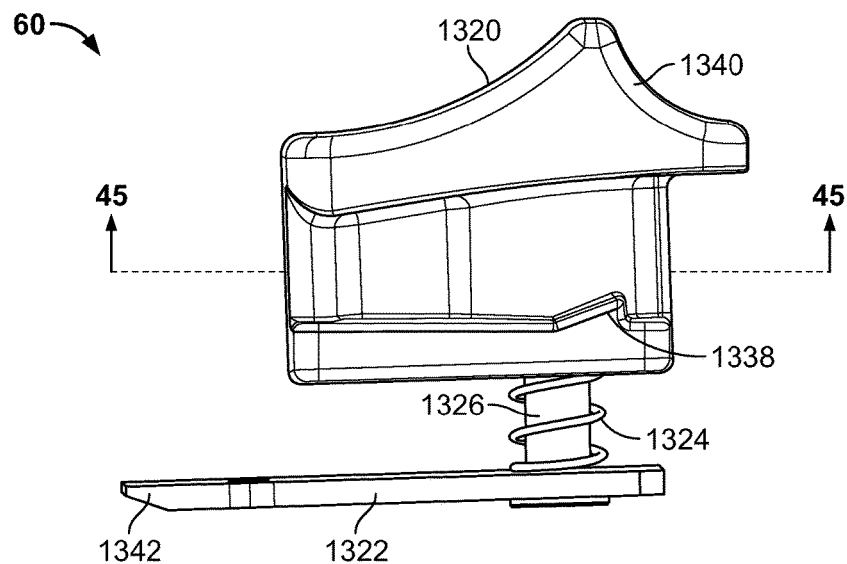
FIG. 43 is a profile view of an exemplary repositionable lock in accordance with the instant disclosure.
Figure 44:
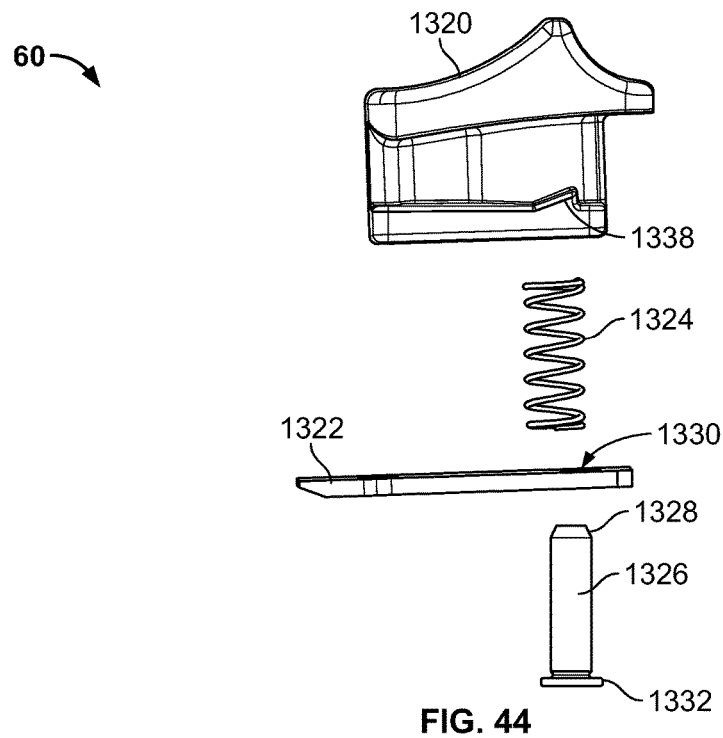
FIG. 44 is an exploded view of the exemplary components of FIG. 43.
Figure 45:
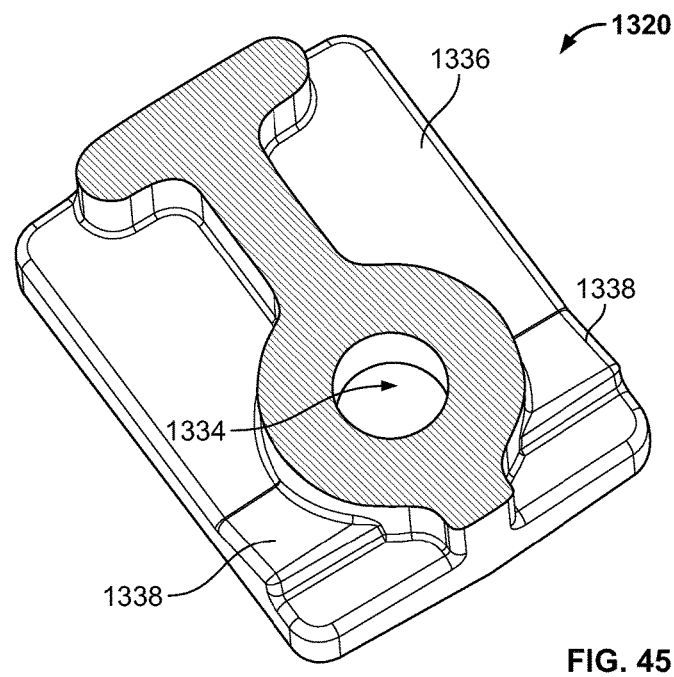
FIG. 45 is a cross-sectional view of the exemplary thumb button of FIG. 43 taken along line 45-45.

Turning to FIGS. 43-45, the repositionable lock 60 includes a thumb button 1320 that is spring biased with respect to a base plate 1322. In exemplary form, the thumb button 1320 includes a hollow cavity 1334 open on an underneath side of the thumb button that is sized to receive a portion of a spring 1324 and a pylon 1326. Assembly of the repositionable lock 60 includes feeding a tapered end 1328 of the pylon 1326 through an opening 1330 extending through the base plate 1322 so that a flange 1332 at an opposing end of the pylon inhibits complete throughput of the pylon. After having the pylon 1326 extend through the base plate 1322, the spring 1324 is positioned to circumscribe the majority of the longitudinal length of the pylon. Thereafter, the tapered end 1328 of the pylon 1326, along with a portion of the spring 1324, is inserted into the hollow cavity 1334 open on an underneath side of thumb button 1320.

When the repositionable lock 60 is mounted to the housings 1000, 1002, a bottom of the base plate 1322 is seated upon the complementary left and right ledges 1048, 1050. In order to maintain the repositionable lock 60 in a biased state, the fourth opening 1022 lateral or widthwise dimension is smaller than the lateral or widthwise dimension of a base 1336 of the thumb button 1320, thereby precluding vertical removal of the thumb button (and repositionable lock 60 internal components) from the interior of the housings 1000, 1002 when the housings are mounted to one another. In other words, the housings 1000, 1002 ledges 1048, 1050 and peripheral surfaces 1008, 1010 operate to sandwich the repositionable lock 60 components therebetween (but for a thump pad 1340 of the thumb button 1320). A portion of each housing 1000, 1002 delineating the fourth opening 1022 operates as overhangs so that the triangular cavity 1054 of each housing is longitudinally aligned with corresponding triangular projections 1338 of the thumb button 1320. In this fashion, the repositionable lock 60 is longitudinally repositionable (in a proximal-distal direction) with respect to the housings 1000, 1002 within a predetermined range of motion. At a proximal end of the range of motion, the triangular projections 1338 of the thumb button 1320 are received within the triangular cavities 1054 of the housings 1000, 1002. When in this position, the repositionable lock 60 is beyond an area of travel of the first and second wheel controls 40, 50. But when the thump pad 1340 of the thumb button 1320 is depressed and moved distally, causing the thumb button to slide on top of the ledges 1048, 1050 and underneath the peripheral surfaces 1008, 1010, the triangular projections 1338 are removed from the triangular cavities 1054 of the housings 1000, 1002. Upon reaching the distal end of the range of motion for the repositionable lock 60, a distal tapered end 1342 of the base plate 1322 interposes two adjacent teeth of each plurality of teeth 1170, 1270, thereby inhibiting rotational motion of both wheels 1110, 1140 and rotational motion of both pulleys 1120, 1130. In this distal position, the repositionable lock 60 is operative to lock the vertical position and the lateral position of the end effector 100. It is envisioned that while in this locked position, the end effector 100 may manipulated using the lever control 80 to reposition the jaws 240, 250 of the end effector 100 to open the occlusion clip 102.

Figure 46:
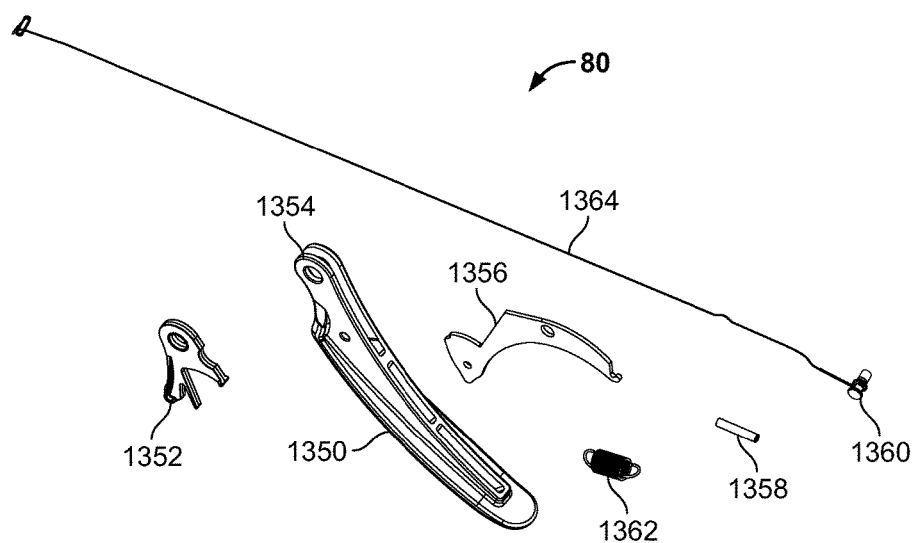
FIG. 46 is an exploded view of an exemplary control for repositioning the end effector jaws in accordance with the instant disclosure.
Figure 47:
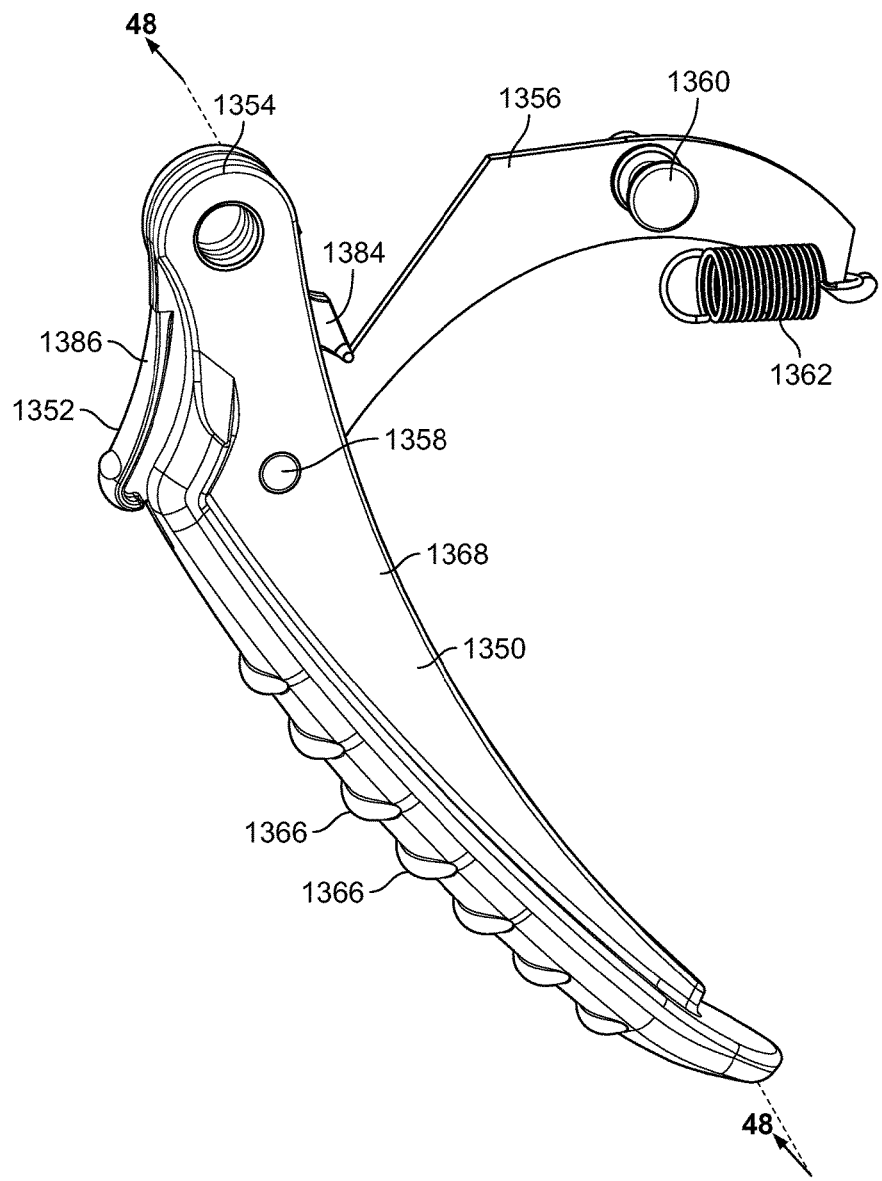
FIG. 47 is an assembled view of the exemplary control of FIG. 46.
Figure 48:
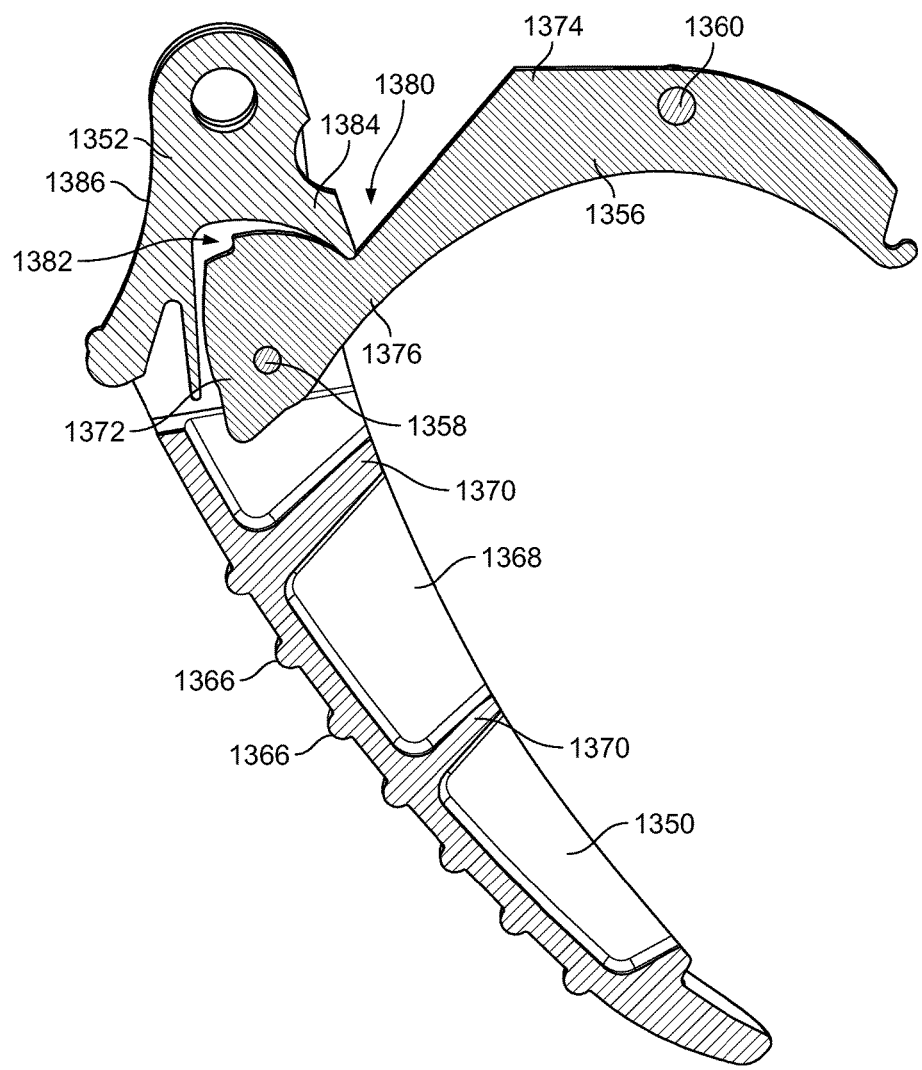
FIG. 48 a cross-sectional view of the exemplary control of FIG. 47 taken along line 47-47.
Figure 49:
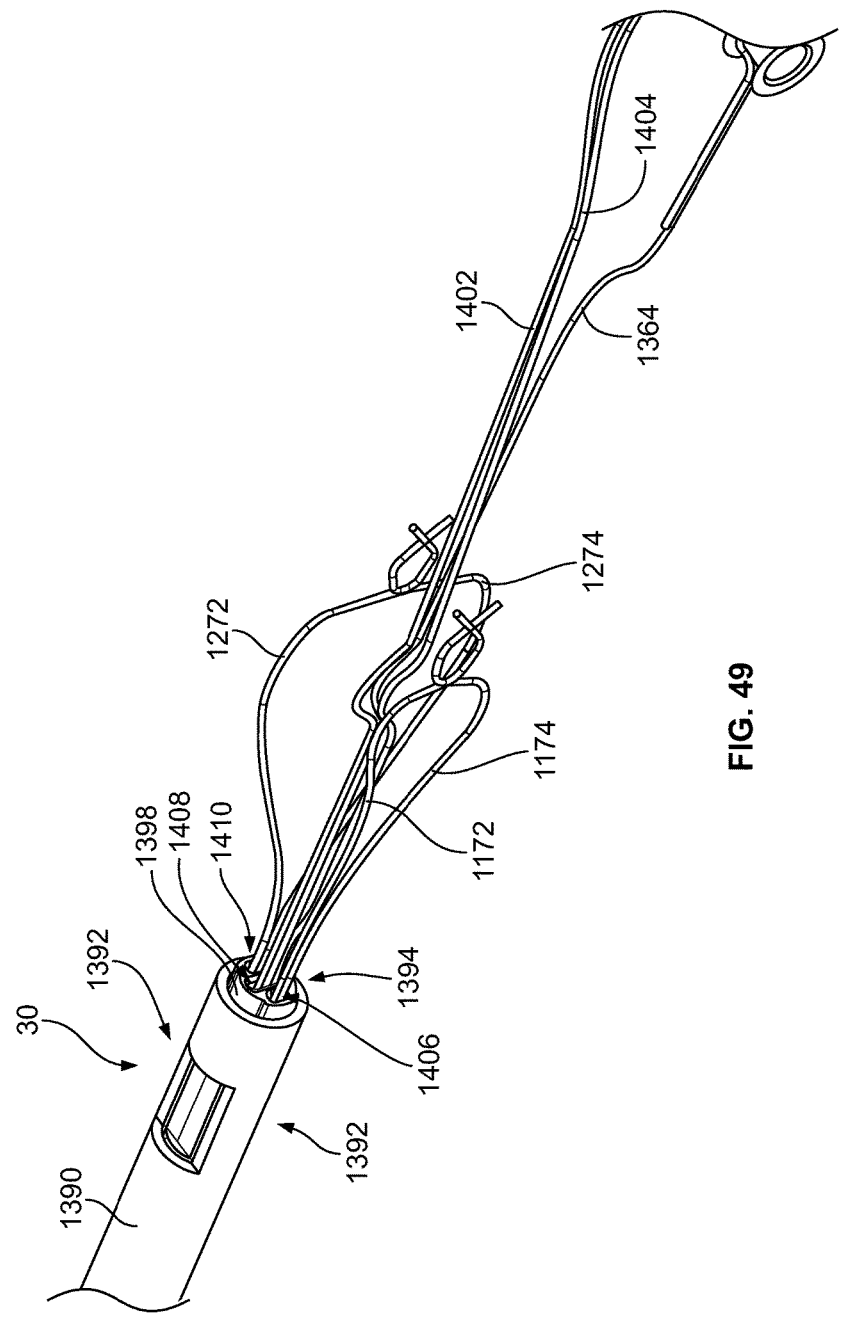
FIG. 49 is an elevated perspective view of an exemplary shaft assembly along with associated control and deployment wires in accordance with the instant disclosure.

Referring to FIGS. 46-48, the lever control 80 comprises a handle 1350 pivotally mounted to the hollow axle 1028 extending from the interior surface 1012 of the right side housing 1002. A trigger 1352 is concurrently and pivotally mounted to the hollow axle 1028 and interposes spaced apart loops 1354 of the handle 1350. The trigger 1352 is repositionable with respect to the handle 1350 in order to lock and selectively unlock a position of the handle with respect to a slide arm 1356. In exemplary form, the slide arm 1356 is pivotally mounted to the handle 1350 using a pin 1358 and is concurrently mounted to a bobbin 1360 that is configured to slide within the oblong, hollow ridge 1040 of the right side housing 1002 in proximal and distal directions. A spring 1362, mounted to the slide arm 1356 and to the spring retainer projection 1032 of the right side housing 1002, operates to bias the slide arm 1356 in its most distal position. But this spring bias may be overcome by a user pulling upward on the handle 1350 (toward the second opening 1018), thereby causing the handle to pivot and reposition the slide arm 1356 proximally. As the slide arm 1356 is repositioned, so too is the bobbin 1360 and a control wire 1364 mounted to the bobbin. More specifically, as the bobbin 1360 is repositioned proximally from the handle 1350 being pulled toward the housings 1000, 1002, the control wire 1364 is repositioned proximally as a result of being placed under greater tension. Upon the bobbin 1360 reaching near or at the most proximal of its range of motion, the trigger 1352 engages the slide arm 1356 to inhibit further motion that would result in the bobbin moving distally. In this fashion, the trigger 1352 operates to lock the position of the slide arm 1356 and the bobbin 1360, which in exemplary form corresponds to the end effector 100 opening the occlusion clip 102 for positioning about a left atrial appendage.

The handle 1350 has a generally arcuate shape, with a concave rear profile and a convex front profile. On this front profile are a series of raised juts 1366 that more readily allow a user to grip the handle 1350. The rear profile is majorly delineated by a pair of spaced apart struts 1368 that are interposed by a series of ribs 1370 that cooperate to form a series of hollows. Each strut 1368 includes a through orifice aligned with the other strut and sized to receive the pin 1358 about which the slide arm 1356 rotates. And each strut 1368 terminates at a spaced apart loop 1354 that facilitates mounting the handle 1350 to the housings 1000, 1002, while concurrently unimpeding rotation of the slide arm 1356.

In exemplary form, the slide arm 1356 includes a head 1372 with an orifice that receives the pin 1358, where the head is connected to a body 1374 of the slide arm via neck 1376. Proximate where the head 1372 and neck 1376 join one another on the top side of the slide arm 1356 is a V-shaped cavity 1380, which is accompanied by a catch 1382 formed into the head. As will be discussed in more detail hereafter, the V-shaped cavity 1380 is intended to receive a portion of a rider 1384 of the trigger 1352 as the handle is in an extended position. But as the handle 1350 is rotated upward, the rider 1384 slides against the top surface of the slide arm 1356 and out of the V-shaped cavity 1380 and becomes seated within the catch cavity 1382 when the handle is fully or almost fully brought adjacent the housings 1000, 1002 (indicative of the slide arm 1356 being positioned proximally to tension the control wire 1364 and, in exemplary form, operative to move the jaws 240, 250 apart from one another to open the occlusion clip 102). In order to release the handle from this rotated position adjacent the housings 1000, 1002, a forward end 1386 of the trigger 1352 is depressed, thereby causing the rider 1384 to move out of the catch cavity 1380 and into the V-shaped cavity 1380. When this occurs (in addition to slacking the control wire 1364 and move the jaws 240, 250 toward one another), presuming the user is not pulling upward on the handle 1350, the spring bias resulting from the spring 1362 being in tension causes the slide arm 1356 to move distally and pivot about the handle 1350, thereby moving the handle away from the housings 1000, 1002. A more detailed discussion of the control and deployment wires and the shaft assembly 30 follows.

Referring to FIGS. 1, 49, and 51-56, the shaft assembly 30 couples the end effector 100 to the user control 20. In exemplary form, the shaft assembly includes an elongated shaft 1390 having a pair of longitudinal cut-outs 1392 sized to receive the pair of retention plates 1026 extending from the interior surface 1012 of the right side housing 1002. The retention plates 1026 mount the shaft assembly 30 to the user control 20 and also operate to inhibit proximal-distal repositioning of the shaft assembly independent of the user control. The elongated shaft 1390 is cylindrical in shape and extends in a generally linear direction. An interior of the elongated shaft 1390 is hollow and includes opposing proximal and distal circular openings 1394 at each end. The proximal opening 1394 is sized to allow insertion of a wire alignment guide 1398 (which also has corresponding cut-outs to receive the retention plates 1026) having three dedicated through channels 1406, 1408, and 1410. Each through channel is configured to receive at least two wires and operates to inhibit tangling of adjacent wires. More specifically, the first channel 1406 receives the control wires 1172, 1174 mounted to the first pulley 1120. A second channel 1408 receives the deployment wires 1402, 1404 mounted to the repositionable tab 70, as well as receiving control wire 1364 mounted to the bobbin 1360. Finally, the third channel 1410 receives the control wires 1272, 1274 mounted to the second pulley 1130. The wire alignment guide 1398 need not extend the entire length of the elongated shaft 1390 so that the distal end opening provides for throughput of all of the wires 1172, 1174, 1272, 1274, 1364, 1402, 1404 where the wires are segregated using the clevis 110, which circumscribes and mounts to the elongated shaft via friction fit. More specifically, the longitudinal passage 402 at the proximal end 404 of the clevis is sized to receive the distal end of the elongated shaft 1390. In this manner, the control wires 1272, 1274 individually extend through a respective through hole 410 of the clevis, while the other wires 1172, 1174, 1364, 1402, 1404 extend through the elongated through hole 412 of the clevis. Downstream from the clevis 110, the control wires 1272, 1274 are individually fed through one of the cylindrical, enlarged openings 469 of the universal 120 and correspondingly mounted to the universal. Likewise, the control wires 1172, 1174 individually extend through a respective channel 476, 478 of the universal 120, while the other wires 1364, 1402, 1404 extend through the opening 474 of the universal. Downstream from the universal 120, the control wires 1172, 1174 are individually fed through one of the openings 528 of the linkage housing and correspondingly mounted to the linkage housing. Conversely, the other wires 1364, 1402, 1404 extend through the channel 546 of the linkage housing 130.

Downstream from the linkage housing 130, the control wire 1364 is mounted to the pulley 220, while the deployment wires 1402, 1404 are respectively directed through openings 674 of the jaws 240, 250.

Turning back to FIGS. 30-57, assembly of the exemplary user control 20 will be described in more detail. In exemplary form, the wires 1172, 1174, 1272, 1274, 1364, 1402, 1404 are routed through the elongated shaft 1390 and the wire alignment guide 1398 and into the interior of the housings 1000, 1002. In particular, the deployment wires 1402, 1404 are routed to the proximal end of the user control 20 and attached to the repositionable tab 70. In exemplary fashion, the repositionable tab 70 may be frictionally seated within the proximal opening 1020 or may be otherwise attached so that removal of the repositionable tab requires rotational motion. In addition to the deployment wires 1402, 1404 being routed, so too is the deployment wire 1364. By way of example, the trigger 1352 and the handle 1350 are aligned so that the hollow axle 1028 of the right side housing 1002 extends through both components. Likewise, the slide arm 1356 is pivotally mounted to the handle 1350 via the pin 1358. An opposing portion of the slide arm 1356 is mounted to the bobbin 1360 so that a portion of the bobbin is seated within a cavity within the right side housing 1002 delineated by the hollow ridge 1040. The deployment wire 1364 is mounted to the bobbin 1360, while the slide arm 1356 and bobbin are spring biased by way of engagement between the spring 1362, which is also mounted to the right side housing 1002. In this fashion, the lever control 80 is spring biased and operative to open and close the jaws 240, 250.

Four of the control wires 1172, 1174, 1272, 1274 are associated with the first and second wheel controls 40, 50. Specifically, assembly of the wheel controls 40, 50 includes positioning the second wheel 1140 to extend through the sixth opening 1052 extending through the right side housing. The axle 1420 is positioned to extend through the center of the second wheel 1140 and be received within the hollow cylinder 1062 of the housings 1000, 1002. Before assembling the housings 1000, 1002, however, the axle 1420 receives in succession the second pulley 1130, the first pulley 1120, and the first wheel 1110. After the pulleys 1120, 1130 are received on the axle 1420, the control wires 1172, 1174, 1272, 1274 are mounted thereto while ensuring the end effector 100 is in a yaw and pitch neutral position. As discussed previously, two control wires 1172, 1272 go over top of a respective pulley 1120, 1130, while the other two control wires 1174, 1274 go under a respective pulley and are secured thereto via a clamp plate 1176, 1276 and a set screw 1178, 1278. In this fashion, when a user decides to change the yaw of the end effector 100, the user engages the control knob 1160 of the first wheel 1110 to rotate the first wheel clockwise or counterclockwise. In exemplary fashion, clockwise rotation of the first wheel 1110 (moving the control knob proximally) operates to pivot the universal 120 with respect to the clevis 110 to the right, whereas counterclockwise rotation of the first wheel (moving the control knob distally) operates to pivot the universal with respect to the clevis to the left. Moreover, when a user decides to change the pitch of the end effector 100, the user engages the control knob 1260 of the second wheel 1140 to rotate the second wheel clockwise or counterclockwise. In exemplary fashion, clockwise rotation of the second wheel 1140 (moving the control knob proximally) operates to pivot the linkage housing 130 upward with respect to the universal 120, whereas counterclockwise rotation of the second wheel (moving the control knob distally) operates to pivot the linkage housing 130 downward with respect to the universal 120.

In order to retard unwanted rotation of the first and second wheel 1110, 1140, installation of the repositionable lock 60 includes seating the base plate 1336 upon the corresponding ledges 1048, 1050 (initially upon the right side ledge 1048) after already having assembled the repositionable lock as discussed above. When installed properly, only the thumb pad 1340 of the thumb button 1320 extends above the housings 1000, 1002. And proximal and distal motion of the repositionable lock 60 are available, where a most distal position of the repositionable lock places the base plate 1342 to interpose corresponding teeth 1170, 1270 of the wheels 1110, 1140, thereby inhibiting further rotation of the wheels. The repositionable lock 60 may be disengaged simply by moving the thumb pad 1340 proximally until the base plate 1342 no longer engages corresponding teeth 1170, 1270 of the wheels 1110, 1140.

After the associated components have been installed and mounted to the right side housing 1002, the left side housing 100 may be repositioned to close the interior and contain the desired portions of the components. In order to ensure continued closure of the housings 1000, 1002, it is within the scope of the invention to weld or otherwise fasten the peripheral surfaces of the housings using any number of options such as, without limitation, press fit, screws/fasteners adhesives, ultrasonic welding, heat welding, and laser welding.

The following comprises a description of exemplary processes for utilizing the exemplary surgical tool 10. Initially, an incision is made on either the left or right side of the chest wall in an intercostal space that is appropriate for the desired angle of approach to a left atrial appendage (LAA). The incision may be made through the chest wall or through the abdomen (or through the back) as part of various procedures that include, without limitation, an open sternotomy, a left thoracotomy, a right thoracotomy, a left port, a right port, a subxiphoid approach, and a transdiaphragmatic approach. Post incision, a trocar (e.g., 10 mm or larger) may be inserted through the incision to extend into the thoracic cavity. In certain instances, it may be preferred to insufflate the thoracic space subsequent to trocar insertion using known techniques. Using at least one of the incision and trocar, surgical instruments are introduced into the thoracic space in order to perform a series of dissections, including dissection of the pericardium, to provide egress to the LAA. After having access to the LAA, the end effector 100 of the surgical tool 10 may be inserted into the thoracic cavity by way of the incision or trocar.

The end effector 100 is passed through the trocar or incision and the user manipulates the user controls 20 to navigate the end effector proximate the LAA. By way of example, the first wheel control 40 is operative to vary the yaw of the end effector 100 within an X-Y plane (e.g., depending upon the frame of reference, the first wheel control 40 provide lateral adjustability of the end effector 100 with respect to the housings 1000, 1002), as well as the second wheel control 50 being operative to vary the pitch of the end effector within an Y-Z plane (e.g., depending upon the frame of reference, the second wheel control 50 provides up and down adjustability of the end effector with respect to the housings). Specifically, a user grasping the user control 20 is able to rotate the first wheel 1110 to change the lateral position of the end effector 100, to which the LAA occlusion clip 102 is mounted, by tensioning a control wire 1172, 1174 extending though the clevis 110 and mounted to the universal 120. Likewise, the user grasping the user control 20 is able to rotate the second wheel 1140 to change the vertical position of the end effector 100 by tensioning a control wire 1272, 1274 extending though the clevis 110 and universal 120 that is mounted to the linkage housing 130. If desired, the user of the surgical tool 10 may use the thumb button 1320 of the repositionable lock 60 to lock the end effector 100 in place (to fix the X-Y and Y-Z orientations) to create a single position, rigid surgical tool 10. After navigating the LAA occlusion clip 102 proximate the LAA, the occlusion clip is opened prior to deployment on the LAA.

Opening the LAA occlusion clip 102 is carried out by actuating the lever control 80. In particular, the handle 1350 is pivotally repositioned toward the housings 1000, 1002, which is operative to tension the control wire 1364 and cause the end effector 100 to further separate its jaws 240, 250 from one another and open the clip 102. More specifically, tensioning the control wire 1364 is operative to reposition the pulley 220 proximally. Because a respective cylindrical lateral end of the pulley 220 is received in a through opening 646 of a respective toggle 200, 210, when the pulley 220 is repositioned proximally, so too are the toggles repositioned proximally (toward the universal 120) as well as rotating about an axis extending through the opening 646. In particular, the proximal motion and rotation of the toggles 200, 210 operates to push against the first and second drive links 140, 150 via the ninth and tenth pins 310, 320 causing the drive links to move away from one another. But the connection between the first and second drive links 140, 150 and the linkage housing 130, via the first pin 160, causes the drive links to pivot with respect to the linkage housing about the first pin when the drive links are attempted to be moved away from one another via the motion of the toggles 200, 210.

The pivoting motion of the drive links 140, 150 is transferred to the jaws 240, 250 via the connection therebetween, facilitated by the fifth and sixth pins 260, 270. More specifically, the pivoting of the drive links 140, 150 away from one another causes the jaws 240, 250 to move away from one another. But the movement of the jaws 240, 250 away from one another is constrained by the connection of the jaws to the first and second parallel links 180, 190, which are themselves pivotally mounted to the linkage housing 130. The additional constraint offered by the parallel links 180 results in motion of the jaws 240, 250 that maintains the jaws in a generally parallel relationship as the jaws are moved from a closed position (adjacent one another with spacing to accommodate the clip 102) to a fully open position (spaced away from one another to open the clip to a predetermined maximum extent necessary to position the clip on a LAA). This fully open position of the jaws 240, 250 coincides with the surface of the toggle connector portions 640 contacting the first and second surfaces 582, 584 of the inner arms 534, 536, thus stopping further proximal and pivoting motion of the toggles 200, 210. In other words, the inner arms 534, 536 of the linkage housing 130 operate to limit the travel of the toggles 200, 210, thereby setting the maximum spacing between the jaws 240, 250 in a fully open position (see FIG. 2).

As long as the jaws 240, 250 are attached to the occlusion clip 102, the motion of the jaws results in corresponding motion of the occlusion clip. More specifically, when the jaws are in a closed position (see FIG. 1) and mounted to the occlusion clip 102, the bias of the occlusion clip retains the jaws in the closed position. But when one wants to open the occlusion clip 102 in anticipation of positioning the clip around a LAA, the user of the device 10 must overcome the bias of the occlusion clip. In order to do this, the device 10 incorporates structures that provide a mechanical advantage allowing the user to pivot the handle 1350 toward the housings 1000 and tension the control wire 1364, which as discussed in greater detail previously, ultimately causing the jaws 240, 250 to separate from one another and correspondingly separate the parallel beams of the occlusion clip 102 from one another.

Post opening of the LAA occlusion clip 102, the clip is advanced over the distal tip of the LAA with the LAA passing between corresponding occlusion beams of the clip, stopping only upon reaching the base of the LAA. It should be noted that forceps may be used to grasp a portion of the LAA when positioning the LAA occlusion clip 102. After the clip 102 has been positioned at the base of the LAA, with the LAA interposing corresponding occlusion beam surfaces of the clip, the user of the surgical tool 10 may close the clip 102 to sandwich the LAA between the occlusion surfaces.

Closing the LAA occlusion clip 102 is also carried out by actuating the lever control 80. Specifically, the user depresses the trigger 1352 to allow the handle 1352 (which is biased to move away from the housings 1000, 1002) to reposition away from the housings 1000, 1002 and thereafter guide the handle away from the housings. By repositioning the handle 1352 away from the housings 1000, 1002, the control wire 1364 is repositioned and facilitates the jaws 240, 250 of the end effector 100 moving closer to one another (from the bias of the clip 102 while the clip is mounted to the end effector 100), thereby sandwiching the clip around the LAA. More specifically, by repositioning the handle 1352 away from the housings 1000, 1002, the tension on the control wire 1364 is lessened.

Lessening the tension of the control wire 1364 causes the end effector 100 to reposition its jaws 240, 250 toward one another, which coincides with closing the occlusion clip 102. More specifically, lessening the tension of the control wire 1364 allows the bias of the occlusion clip 102 to become the dominant force and reposition the jaws 240, 250 toward one another. In exemplary form, the dominant biasing force of the occlusion clip 102 is operative to reposition the jaws 240, 250, which in turn causes the first and second drive links 140, 150 to pivot toward one another, coinciding with the parallel links 180, 190 pivoting toward one another. Likewise, the toggles 200, 210 are pivoted and repositioned distally, as is the pulley 220, ultimately leading to the component positions shown in FIG. 1.

After the occlusion clip 102 is positioned about the LAA, various steps may be undertaken to ensure the entire periphery of a portion of LAA is sandwiched by the clip 102 such as, without limitation, direct visual verification and utilization of a transesophageal echocardiogram. If any problems are determined with respect to the clip 102 placement, the opening and closing clip sequence may be repeated to adjust the positioning of the clip with respect to the LAA. Upon closing the LAA occlusion clip 102 around a periphery of a portion of the LAA, proximate the LAA base, as well as confirming the placement of the closed clip being operative to occlude the LAA, the surgeon may release the occlusion clip from the end effector 100.

To release the clip 102 from the end effector 100, the user removes the repositionable tab 70 from the proximal end of the user control 20. This removal of the repositionable tab 70 causes the deployment wires 1402, 1404 to be repositioned proximally and discontinue engagement with the suture loops 1412. When the engagement with the suture loops 1412 is discontinued, the occlusion clip 102 is no longer fastened to the jaws 240, 250 (i.e., the jaws can be opened and closed without repositioning the clip). As discussed previously, the repositionable tab 70 may be withdrawn from the user control 20 in a straight pull fashion by overcoming a friction fit force or may be withdrawn via other movements including, without limitation, rotation and a combination of rotation and a straight pull that may make use of threads or detents. After disengagement between the occlusion clip 102 and the end effector 100, the end effector is removed from the cardiac space.

Removal of the end effector 100 from the patient's body is controlled by the user. Because the end effector 100 is open-ended, there is no need to reposition the end effector upward along the LAA because the end effector can be withdrawn laterally, thus reducing the potential for contact between the end effector and the LAA. In other words, the end effector 100 may be removed from around the LAA without having a tip of the LAA passing between the jaws 240, 250. As part of removing the end effector 100 from the cardiac and thoracic space, the user manipulates the user control 20 and causes repositioning of the end effector 100 to allow withdrawal from the patient's body cavity via the incision or trocar. By way of example, it is envisioned that the user repositions the first and second wheel controls 40, 50 in order to longitudinally align the end effector 100 with the shaft assembly 30 prior to removing the end effector through the trocar or incision.

Following from the above description and invention summaries, it should be apparent to those of ordinary skill in the art that, while the methods and apparatuses herein described constitute exemplary embodiments of the present invention, it is to be understood that the inventions contained herein are not limited to the above precise embodiment and that changes may be made without departing from the scope of the invention as defined by the following proposed points of novelty. Likewise, it is to be understood that it is not necessary to meet any or all of the identified advantages or objects of the invention disclosed herein in order to fall within the scope of the invention, since inherent and/or unforeseen advantages of the present invention may exist even though they may not have been explicitly discussed herein.

What is claimed is:

1. A medical instrument comprising:
    a first joint comprising a first member and a second member, the first member configured to be repositionable with respect to the second member in a first degree of freedom;
    a second joint operatively coupled to the first joint, the second joint comprising a third member and a fourth member, the third member configured to be repositionable with respect to the fourth member in a second degree of freedom;
    a pair of repositionable jaws operatively coupled to the first joint and the second joint, the pair of repositionable jaws coupled to a repositionable support that interposes the pair of repositionable jaws and the second joint, the repositionable support maintaining the pair of jaws in a parallel orientation across a range of motion;
    an occlusion clip detachably mounted to the pair of repositionable jaws; and,
    a controller operatively coupled to the first joint, the second joint, and the pair of repositionable jaws, the controller including a first control configured to direct repositioning of at least one of the first member and the second member, and a second control configured to direct repositioning of at least one of the third member and the fourth member, and a third control operatively coupled to the repositionable support and configured to direct repositioning of the pair of repositionable jaws in the parallel orientation.

2. The medical instrument of claim 1, wherein:
the first control comprises a first active control configured to be repositionable among an infinite number of positions, where each of the infinite number of positions orients the first member with respect to the second member within the first degree of freedom; and,
the second control comprises a second active control configured to be repositionable among an infinite number of positions, where each of the infinite number of positions orients the third member with respect to the fourth member within the second degree of freedom.

3. The medical instrument of claim 2, wherein:
the first active control includes a first wheel around which is partially wound a first wire operatively coupled to at least one of the first member and the second member so that rotation of the first wheel translates into movement of at least one of the first member and the second member; and,
the second active control includes a second wheel around which is partially wound a second wire operatively coupled to at least one of the third member and the fourth member so that rotation of the second wheel translates into movement of at least one of the third member and the fourth member.

4. The medical instrument of claim 1, further comprising:
a repositionable lock in selective communication with at least one of the first control and the second control to retard movement in at least one of the first degree of freedom and the second degree of freedom.

5. The medical instrument of claim 4, wherein:
the first control is operatively coupled to a hand-held housing and includes at least one of a pivoting, a sliding, and a rotating first projection extending from the hand-held housing;
the second control is operatively coupled to the hand-held housing and includes at least one of a pivoting, a sliding, and a rotating second projection extending from the hand-held housing; and,
the repositionable lock is operatively coupled to the hand-held housing and includes at least one of a pivoting, a sliding, and a rotating third projection extending from the hand-held housing.

6. The medical instrument of claim 5, wherein:
the first control includes a rotating first projection that comprises a first wheel;
the second control includes a rotating second projection that comprises a second wheel;
the repositionable lock includes a sliding third projection.

7. The medical instrument of claim 1, wherein the controller further includes a fourth control configured to detachably mount the occlusion clip to the pair of repositionable jaws.

8. The medical instrument of claim 7, wherein the fourth control includes a wire concurrently mounted to the occlusion clip and the pair of repositionable jaws.

9. The medical instrument of claim 8, wherein:
the wire comprises at least a first wire and a second wire;
the first wire is concurrently mounted to the occlusion clip and a first of the pair of repositionable jaws;
the second wire is concurrently mounted to the occlusion clip and a second of the pair of repositionable jaws;
the fourth control is repositionable to selectively dismount the first wire from at least one of the occlusion clip and the first of the pair of repositionable jaws, and is repositionable to selectively dismount the second from at least one of the occlusion clip and the second of the pair of repositionable jaws.

10. The medical instrument of claim 1, further comprising a first connection extending along a longitudinal conduit and operatively coupling the third control to the repositionable support.

11. The medical instrument of claim 1, wherein the repositionable support comprises a scissor support that is concurrently mounted to the pair of repositionable jaws and the fourth member of the second joint, the scissor support repositionable between a folded position and an unfolded position, where the folded position has the pair of repositionable jaws in closer proximity to one another than in the unfolded position.

12. The medical instrument of claim 11, wherein the scissor support is operatively coupled to a pulley and the first link.

13. The medical instrument of claim 11, wherein the scissor support includes:
a first link concurrently repositionably and operatively coupled to a first of the pair of repositionable jaws;
a second link concurrently repositionably and operatively coupled to a second of the pair of repositionable jaws;
a third link concurrently repositionably and operatively coupled to the first of the pair of repositionable jaws and the second link; and,
a fourth link concurrently repositionably and operatively coupled to the second of the pair of repositionable jaws and the first link;
wherein the third link is repositionably and operatively coupled to the fourth link.

14. The medical instrument of claim 13, wherein the scissor support includes a fifth link concurrently repositionably and operatively coupled to a sixth link and to the first link, wherein the sixth link is concurrently repositionably and operatively coupled to the fifth link and to the second link.

15. The medical instrument of claim 14, wherein the fifth and sixth links are both mounted to and repositionable with respect to a pulley.

16. The medical instrument of claim 14, wherein:
the second joint includes a first camming surface to facilitate repositioning of the fifth link; and,
the second joint includes a second camming surface to facilitate repositioning of the sixth link.

17. The medical instrument of claim 16, wherein the first connection is operatively coupled to the fifth and sixth links.

18. The medical instrument of claim 17, wherein the first connection includes a pulley operatively coupled to the fifth and sixth links.

19. The medical instrument of claim 17, wherein the third control comprises a repositionable handle operatively coupled to a hand-held housing of the controller.

20. The medical instrument of claim 19, wherein the third control includes a slide arm concurrently mounted to the repositionable handle and the first connection.

21. The medical instrument of claim 20, wherein:
the third control includes a spring to bias at least one of the slide arm and the handle; and,
the third control includes a trigger to selectively unlock the orientation of the handle with respect to the slide arm.

22. The medical instrument of claim 1, wherein the repositionable support comprises a folding pantograph support.

* * * * *